(12) United States Patent
Boylan et al.

(10) Patent No.: US 7,504,513 B2
(45) Date of Patent: Mar. 17, 2009

(54) THIAZOLYL-BENZIMIDAZOLES

(75) Inventors: John Frederick Boylan, Bedminster, NJ (US); Jianping Cai, West Caldwell, NJ (US); Nader Fotouhi, Basking Ridge, NJ (US); Paul Gillespie, Westfield, NJ (US); Robert Alan Goodnow, Jr., Gillette, NJ (US); Kang Le, Green Brook, NJ (US); Christophe Michoud, New York, NY (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/703,306

(22) Filed: Feb. 7, 2007

(65) Prior Publication Data

US 2007/0203210 A1    Aug. 30, 2007

Related U.S. Application Data

(60) Provisional application No. 60/776,964, filed on Feb. 27, 2006.

(51) Int. Cl.
*A61K 31/427* (2006.01)
*C07D 417/04* (2006.01)
*C07D 417/14* (2006.01)

(52) U.S. Cl. .................................. 548/181; 514/365
(58) Field of Classification Search .................. None
See application file for complete search history.

(56) References Cited

U.S. PATENT DOCUMENTS

| 4,322,429 | A  | 3/1982 | Burow |
| 4,818,270 | A  | 4/1989 | Grabiak et al. |
| 6,380,180 | B1 | 4/2002 | Jensen et al. |

FOREIGN PATENT DOCUMENTS

| EP | 1486490 A1 * | 12/2004 |
| WO | WO 02/12242 | 2/2002 |
| WO | WO 02/062804 | 8/2002 |
| WO | WO 03/070283 | 8/2003 |
| WO | WO 03/072062 | 9/2003 |
| WO | WO 03/093249 | 11/2003 |
| WO | WO 2004/011610 | 2/2004 |
| WO | WO 2004/014899 | 2/2004 |
| WO | WO 2004/043936 | 5/2004 |
| WO | WO 2004/046317 | 6/2004 |
| WO | WO 2004/054186 | 6/2004 |
| WO | WO 2004/067000 | 8/2004 |
| WO | WO 2004/074244 | 9/2004 |
| WO | WO 2004/087652 | 10/2004 |
| WO | WO 2004/113322 | 12/2004 |
| WO | WO 2005/019193 | 3/2005 |
| WO | WO 2005/042505 | 5/2005 |
| WO | WO 2005/042525 | 5/2005 |
| WO | WO 2005/075470 | 8/2005 |

OTHER PUBLICATIONS

CA Registry No. 595596-84-2, indexed in the Registry file on STN Sep. 30, 2003.*

* cited by examiner

*Primary Examiner*—Laura L. Stockton
(74) *Attorney, Agent, or Firm*—George W. Johnston; Patricia S. Rocha-Tramaloni; David E. Wildman

(57) ABSTRACT

The invention is directed to compounds of formula (1)

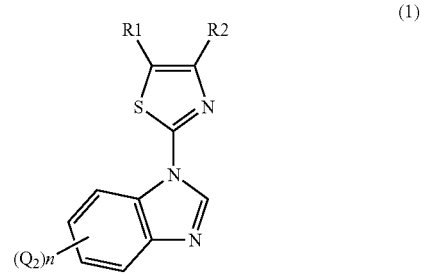

and pharmaceutically acceptable salts thereof, methods for the preparation thereof, and methods of use thereof.

11 Claims, No Drawings

THIAZOLYL-BENZIMIDAZOLES

PRIORITY TO RELATED APPLICATIONS

This application claims the benefit of U.S. Provisional Application No. 60/776,964, filed Feb. 27, 2006, which is hereby incorporated by reference in its entirety.

The present invention is concerned with thiazolyl-benzimidazole derivatives and their pharmaceutically acceptable salts, the manufacture of the aforesaid and their use as therapeutic agents.

PLK1 is a member of the Polo-like kinase family. Polo-like kinases are highly conserved from yeast to humans and play a variety of roles in the G2/M phase transition and in the passage through mitotic phase of the cell cycle. Four Polo-like kinases, PLK1, PLK2 (Snk), PLK3 (Fnk), and PLK4 have been identified in humans. These proteins share extensive homologies across their kinase domains, in C-terminal "Polo" boxes. Using neutralizing antibodies, anti-sense oligos, and dominant-negative protein, PLK1 was shown to be essential for mitosis in vitro cultured cells. Furthermore, down regulation of PLK1 appears to have differential effects in tumor versus "normal" cells in that ablation of PLK1 induced mitotic catastrophe and eventual cell death but G2 arrest in "normal" cells. One plausible explanation is that tumor cells are defective in checkpoint controls and unable to arrest and thus undergo mitotic catastrophe. The roles of PLK2, PLK3, and PLK4 remain elusive.

The expression of PLK1 is restricted to proliferative tissues. Overexpression of PLK1 was detected in solid tumors of various origins (breast, lung, colon, stomach, ovary, smooth muscle, and esophagus) and in non-Hodgkin lymphomas. Furthermore PLK1 has transforming activity; constitutive expression of PLK1 in NIH3T3 cells causes oncogenic focus formation, transformed cells grow in soft agar and form tumors in nude mice.

Therefore, blocking PLK1 kinase activity by a small molecule inhibitor represents a novel approach to target mitosis and may be clearly differentiated from other mitosis-targeting agents on the market such as tubulin binders.

Other therapies which involve the disruption of microtubule formation and degradation through the use of taxanes and vinca alkaloids have become successful ways of treating cancer. Some cancerous cells are able to evade the G2/M cell cycle arrest effect of taxanes and vinca alkaloids. PLK1 inhibition provides a means to target those cells which are able to evade the G2/M cell cycle arresting effect of taxanes and vinca alkaloids.

U.S. Pat. No. 4,818,270 discloses structurally unrelated benzimidazole-thiazole compounds for use as herbicides.

WO200212242 discloses bicyclo-pyrazole compounds that are inhibitors of PLK1. WO200262804 discloses oxazolyl-pyrazole derivatives that are inhibitors of PLK1. WO2003070283 discloses duplex RNAs antisense oligonucleotides that are inhibitors of PLK1. WO2003072062 discloses (E)-2,6-dialkoxystyryl-4-substituted benzylsulfones that are inhibitors of PLK1. WO2003093249 discloses thiazolidinone compounds that are inhibitors of PLK1. WO2004011610 discloses antisense compounds that are inhibitors of PLK1. WO2004014899 discloses thiophene compounds that are inhibitors of PLK1. WO2004043936 discloses pyrimidine compounds that are inhibitors of PLK1. WO2004046317 discloses products and processes for modulating peptide-peptide binding domain interactions including an invention for providing 3-D structures of PLK. WO2004067000 discloses benzothiazole-3-oxides that are inhibitors of PLK1. WO2004074244 discloses pyrimidine compounds that are inhibitors of PLK1. WO2004087652 discloses imidazotriazine compounds that are inhibitors of PLK1. WO2005019193 discloses phenylurea compounds that are inhibitors of PLK1. WO2005042505 discloses thiazolidinones that are inhibitors of PLK1. WO2005042525 discloses pyrimidin-4-yl-3,4-thione compounds that are inhibitors of PLK1. WO2005075470 discloses thiazole compounds that are inhibitors of PLK1.

SUMMARY OF THE INVENTION

According to a first aspect of the invention, there is provided a compound of formula (1):

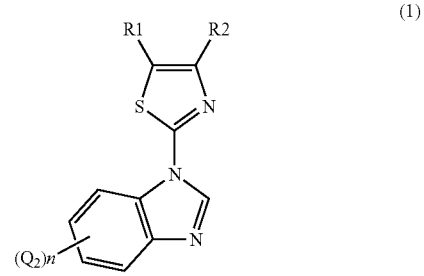

wherein:
n is an integer from 0 to 2;
each $Q_2$ is independently selected from the group consisting of hydroxyl, lower alkoxy, lower alkyl, carboxyl, halogen, —O(CH$_2$)$_m$O(CH$_2$)$_m$CH$_3$, —O(CH$_2$)$_m$OH, —O(CH$_2$)$_m$NR8R9, wherein R8 and R9 are each independently selected from the group consisting of hydrogen and lower alkyl, and —O(CH$_2$)$_m$-heterocyclyl, and wherein each m is, independently, an integer from 2 to 4;
or n is 2 and the $Q_2$ groups are at the 5 and 6 or 6 and 7 positions on the benzimidazole ring and, together with the carbon atoms to which they are bound, form a four to six-membered heterocyclic ring containing at least one atom independently selected from the group consisting of oxygen, nitrogen, and sulfur;
R1 is a member selected from the group consisting of —CH$_2$C(O)R4, —CH(OH)CF$_3$, —C(O)R5 and heterocyclyl, wherein R4 is selected from the group consisting of hydroxyl and —NH$_2$ and R5 is selected from the group consisting of hydroxyl and —NR6R7, wherein R6 and R7 are independently selected from the group consisting of hydrogen, hydroxyl, cyano, lower alkyl, lower cycloalkyl, optionally substituted heterocyclyl, optionally substituted aryl, and —NH—C(O)-optionally substituted aryl; and
R2 is aryl optionally substituted with one or more substituents independently selected from the group consisting of halogen, lower alkoxy, lower alkyl, hydroxyl, lower alkenyl, halo-loweralkyl, hydroxy-loweralkyl, and —C(O)NR8R9 wherein R8 and R9 are each independently selected from the group consisting of hydrogen and lower alkyl, wherein two of said optional substituents can, together with the atoms to which they are bound, form a four to six-membered heterocyclic ring containing at least one atom independently selected from the group consisting of oxygen, nitrogen, and sulfur; or a pharmaceutically acceptable salt thereof.

In another aspect of the invention relates to pharmaceutical compositions comprising of a compound of formula (1). In one embodiment, the pharmaceutical composition further comprises a pharmaceutically acceptable carrier, diluent, or excipient.

In a third aspect of the invention, there is provided a method for treating a subject afflicted with a disease or condition that responds to modulation of PLK1 activity, comprising administering to the subject an amount of a compound of formula (1) or a pharmaceutically acceptable salt, solvate or physiologically functional derivative thereof, or a composition comprising an amount of a compound of formula (1) or a pharmaceutically acceptable salt, solvate or physiologically functional derivative thereof and one or more pharmaceutically acceptable excipients or adjuvants effective to modulate the activity of PLK1 activity in the subject, wherein the modulation ameliorates the disease or condition.

In a fourth aspect of this invention, there is provided a method of treating a neoplasm which is susceptible to inhibition or modulation of PLK activity in an animal.

In a fifth aspect of this invention, there is described a method for treating a PLK-mediated condition characterized by inappropriate cellular proliferation.

In a sixth aspect of this invention, there is described a method for inhibiting proliferation of cells. The method involves incubation of cells with an amount of a compound of formula (1) or a pharmaceutically acceptable salt, solvate, or physiologically functional derivative thereof sufficient to inhibit proliferation of such treated cells whereby such cellular treatment inhibits PLK. In another aspect of the present invention, there is described the means to inhibit cells in the stage of mitosis by treating cells with sufficient quantity of a compound of formula (1) or a pharmaceutically acceptable salt, solvate, or physiologically function derivative thereof thereby inhibiting PLK.

In another aspect, there is provided a process for preparing compounds of formula (1) comprising the steps of:

a) reacting a compound of formula (2)

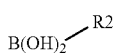

(2)

with a compound of formula (3)

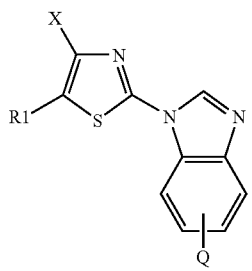

(III)

wherein:
X is Cl, Br, I, O-triflate, or another leaving group, Q is as defined for Q2 above and may be present from 0 to 2 times on the carbocyclic portion of the benzimidazole ring, and R1 and R2 are as set forth above, to yield a compound of formula (1); and b) optionally converting a compound of formula (1) to a pharmaceutically acceptable salt, solvate, or physiologically functional derivative thereof; or c) optionally converting a compound of formula (1) or a pharmaceutically acceptable salt, solvate, or physiologically functional derivative thereof to a different compound of formula (1) or a pharmaceutically acceptable salt, solvate or physiologically functional derivative thereof.

In another aspect, the invention provides a radiolabeled compound of formula (1) or a pharmaceutically acceptable salt, solvate, or physiologically functional derivative thereof.

DETAILED DESCRIPTION OF THE INVENTION

All patents, patent applications and publications mentioned in the present specification are hereby incorporated by reference in their entirety. In case of a conflict in terminology, the present specification is controlling.

DEFINITIONS

Unless otherwise indicated, the following definitions are set forth to illustrate and define the meaning and scope of the various terms used to describe the invention herein.

The term "halogen" refers to one or more members selected from fluorine, chlorine, bromine, and iodine, preferably to fluorine and chlorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

Alkyl groups can optionally be substituted singly or multiply, e.g. with halogen, hydroxy, lower-alkoxy, lower-alkoxy-carbonyl, $NH_2$, NH(lower-alkyl) and/or N(lower-alkyl)$_2$. Unsubstituted alkyl groups are preferred.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may optionally have a substitution pattern as described earlier in connection with the term "alkyl". Unsubstituted lower-alkyl groups are preferred.

The term "alkylene" alone or in combination with other groups, refers to a branched or straight-chain divalent saturated aliphatic hydrocarbon radical of one to twenty carbon atoms, or one to sixteen carbon atoms, or one to ten carbon atoms, or one to seven carbon atoms, or one to four carbon atoms.

Alkylene groups can optionally be substituted, singly or multiply, e.g. with halogen, hydroxy, lower-alkoxy, lower-alkoxy-carbonyl, $NH_2$, NH(lower-alkyl) and/or N(lower-alkyl)$_2$. Unsubstituted alkylene groups are preferred.

The term "lower-alkylene", alone or in combination with other groups, refers to a branched or straight-chain divalent alkyl radical of one to seven carbon atoms, preferably one to four carbon atoms. This term is further exemplified by such radicals as methylene, ethylene, propylene, butylene and the like. A lower-alkylene group may optionally have a substitution pattern as described earlier in connection with the term "alkyl". Unsubstituted lower-alkylene groups are preferred.

The term "alkoxy" refers to the group R'—O—, wherein R' is alkyl. The term "lower-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Alkoxy and lower-alkoxy groups may optionally have a substitution pattern as described earlier in connection with the term "alkyl". Unsubstituted alkoxy and lower-alkoxy groups are preferred.

The term "alkyleneoxy" refers to the group —R'—O—, wherein R' is alkylene. The term "lower-alkyleneoxy" refers to the group —R'—O—, wherein R' is lower-alkylene.

The term "aryl" refers to an aromatic carbocyclic or heterocyclic ring or ring system. Examples of aryl groups include phenyl, furanyl, thiophenyl, pyridinyl, thiazolyl and oxazolyl, which can optionally be mono- or multiply-substituted by lower-alkyl, lower-alkoxy, halogen, CN, $CF_3$, hydroxy, $NO_2$, $NH_2$, NH(lower-alkyl) and/or N(lower-alkyl)$_2$. Preferred substituents are lower-alkyl, lower-alkoxy and halogen. Aryl may also signify fused bicyclic aromatic systems such as naphthalene and benzimidazole.

The term "carbocyclic ring" refers to a substituted or unsubstituted monocyclic or bicyclic hydrocarbon ring system of 5 to 10 members, preferably 5 or 6 members. Preferred groups include phenyl, naphthyl, tolyl, xylyl, etc.

The term "heterocyclic ring" or "heterocyclyl" refers to a 5- or 6-membered ring which can comprise 1 to 4 atoms selected from nitrogen, oxygen and/or sulfur such as tetrahydropyridine, dihydrofuran, dihydropyran, furyl, pyrrolyl, pyridyl, 1,2-, 1,3- and 1,4-diazinyl, thienyl, oxazolyl, oxadiazolyl, isoxazolyl, thiazolyl, isothiazolyl, tetrazolyl, or imidazolyl. The heterocyclic ring may be optionally substituted with an aryl group or may be optionally substituted as described earlier in connection with the term "aryl". Heterocylic aryl, also referred to herein as heteroaryl, includes fused bicyclic aromatic systems such as quinoline, isoquinoline, benzo[b]thiophene, and benzimidazole.

The term "lower alkenyl", alone or in combination with other groups, refers to a branched or straight-chain monovalent radical of one to seven carbon atoms, preferably one to four carbon atoms, that contains at least one carbon to carbon double bond. This term is further exemplified by such radicals as vinyl, propenyl, and butenyl.

The term "pharmaceutically acceptable salts" embraces salts of the compounds of formula (I) with inorganic or organic acids such as hydrochloric acid, hydrobromic acid, nitric acid, sulfuric acid, phosphoric acid, citric acid, formic acid, maleic acid, acetic acid, fumaric acid, succinic acid, tartaric acid, methanesulfonic acid, p-toluenesulfonic acid and the like, which are non-toxic to living organisms.

This term also encompasses carboxylate salts having inorganic cations, such as alkali and alkaline earth metal cations (for example, lithium, sodium, potassium, magnesium, barium and calcium); ammonium cations; or organic cations, for example, dibenzylammonium, benzylammonium, 2-hydroxyethylammonium, bis(2-hydroxyethyl)ammonium, phenylethylbenzylammonium, and the like. Other cations encompassed by the above term include the protonated form of procaine, quinine and N-methylglucosamine, and the protonated forms of basic amino acids such as glycine, ornithine, histidine, phenylglycine, lysine, and arginine.

The term "leaving group" is a chemical group which is removed or replaced during a reaction. Examples of leaving groups are halogen, mesylate and tosylate.

Thus, the invention provides a compound of formula (1)

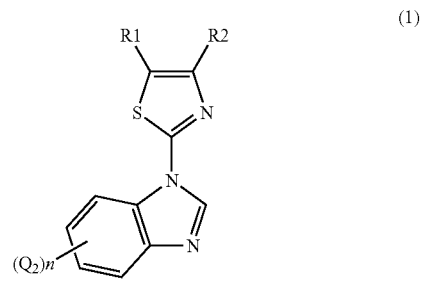

(1)

wherein:

n is an integer from 0 to 2;

each $Q_2$ is independently selected from the group consisting of hydroxyl, lower alkoxy, lower alkyl, carboxyl, halogen, —O(CH$_2$)$_m$O(CH$_2$)$_m$CH$_3$, —O(CH$_2$)$_m$OH, —O(CH$_2$)$_m$NR8R9, wherein R8 and R9 are each independently selected from the group consisting of hydrogen and lower alkyl, and —O(CH$_2$)$_m$-heterocyclyl, and wherein each m is, independently, an integer from 2 to 4;

or n is 2 and the $Q_2$ groups are at the 5 and 6 or 6 and 7 positions on the benzimidazole ring and, together with the carbon atoms to which they are bound, form a four to six-membered heterocyclic ring containing at least one atom independently selected from the group consisting of oxygen, nitrogen, and sulfur;

R1 is a member selected from the group consisting of —CH$_2$C(O)R4, —CH(OH)CF$_3$, —C(O)R5 and heterocyclyl, wherein R4 is selected from the group consisting of hydroxyl and —NH$_2$ and R5 is selected from the group consisting of hydroxyl and —NR6R7, wherein R6 and R7 are independently selected from the group consisting of hydrogen, hydroxyl, cyano, lower alkyl, lower cycloalkyl, optionally substituted heterocyclyl, optionally substituted aryl, and —NH—C(O)-optionally substituted aryl; and R2 is aryl optionally substituted with one or more substituents independently selected from the group consisting of halogen, lower alkoxy, lower alkyl, hydroxyl, lower alkenyl, halo-loweralkyl, hydroxy-loweralkyl, and —C(O)NR8R9 wherein R8 and R9 are each independently selected from the group consisting of hydrogen and lower alkyl, wherein two of said optional substituents can, together with the atoms to which they are bound, form a four to six-membered heterocyclic ring containing at least one atom independently selected from the group consisting of oxygen, nitrogen, and sulfur; or a pharmaceutically acceptable salt thereof.

Another embodiment is directed to compounds of formula 1 where R2 is optionally substituted aryl.

Another embodiment is directed to compounds of formula 1 where R2 is optionally substituted aryl and where R1 is —C(O)R5.

Another embodiment is directed to compounds of formula 1 where R2 is optionally substituted aryl and where R1 is —C(O)R5 and where R5 is —OH.

Another embodiment is directed to compounds of formula 1 where R2 is optionally substituted heteroaryl.

Another embodiment is directed to compounds of formula 1 where R2 is optionally substituted heteroaryl where R1 is C(O)R5 and R5 is —OH.

Another embodiment is directed to compounds of formula 1 where R2 is optionally substituted phenyl where R1 is —C(O)R5 and R5 is —OH.

Another embodiment is directed to compounds of formula 1 where R2 is phenyl substituted with at least one member selected from the group consisting of hydroxyl and halogen, where R1 is —C(O)R5 and R5 is —OH, preferably where R2 is phenyl substituted with halogen, preferably where R2 is phenyl substituted in the 3-position with halogen.

Another embodiment is directed to compounds of formula 1 where R2 is optionally substituted aryl and where R1 is —C(O)R5 and R5 is —NR6R7, preferably where R6 and R7 are independently selected from the group consisting of hydrogen, lower alkyl, and optionally substituted aryl.

Another embodiment is directed to compounds of formula 1 where n is 1 or 2 and $Q_2$ is independently selected from the group consisting of halogen, lower alkoxy, lower alkoxy-loweralkyleneoxy, and lower alkyl.

Another embodiment is directed to compounds of formula 1 where R2 is optionally substituted aryl and R1 is heterocyclyl, preferably a heterocyclyl group containing at least one nitrogen atom.

The compounds of general formula I in this invention may be derivatized at groups to provide derivatives which are capable of conversion back to the parent compound in vivo.

The invention also relates to pharmaceutical compositions comprising a compound as defined above and a pharmaceutically acceptable carrier and/or adjuvant.

The compounds of formula I may be manufactured by the methods given below, by the methods given in the examples or by analogous methods. Based on the present disclosure, appropriate reaction conditions for the individual reaction steps would be apparent to the person skilled in the art. Starting materials are either commercially available or may be prepared by methods analogous to the methods given below or in the examples or by methods known in the art.

The compounds of formula I and/or their pharmaceutically acceptable salts may be used as medicaments, e.g. in the form of pharmaceutical compositions for enteral, parenteral or topical administration. They may be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical compositions may be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts may be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 750 mg, or 1 to 500 mg, or 1 to 250 mg, or 1 to 200 mg, or 1 to 150 mg, or 1 to 100 mg, or 1 to 75 mg, or 1 to 50 mg, or 1 to 25 mg, or 1 to 10 mg, may be administered. Depending on severity of the disease and the precise pharmacokinetic profile the compound could be administered with one or several daily dosage units, e.g. in 1 to 4 dosage units.

The pharmaceutical preparations conveniently contain about 1 to 500 mg, 1 to 250 mg, 1 to 200 mg, 1 to 150 mg, 1 to 100 mg, 1 to 75 mg, 1 to 50 mg, 1 to 25 mg, or 1 to 10 mg of a compound of formula 1.

Compounds of formula (1) may be conveniently prepared by the methods outlined in Scheme 1 below.

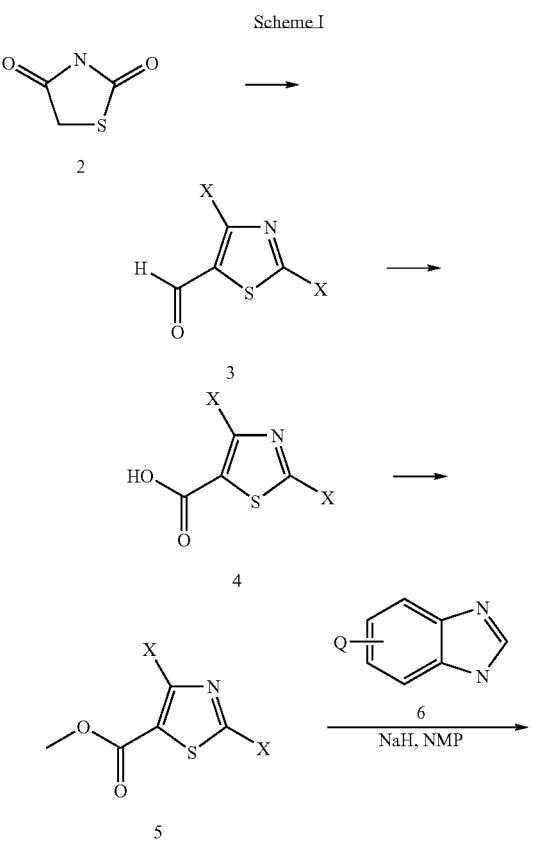

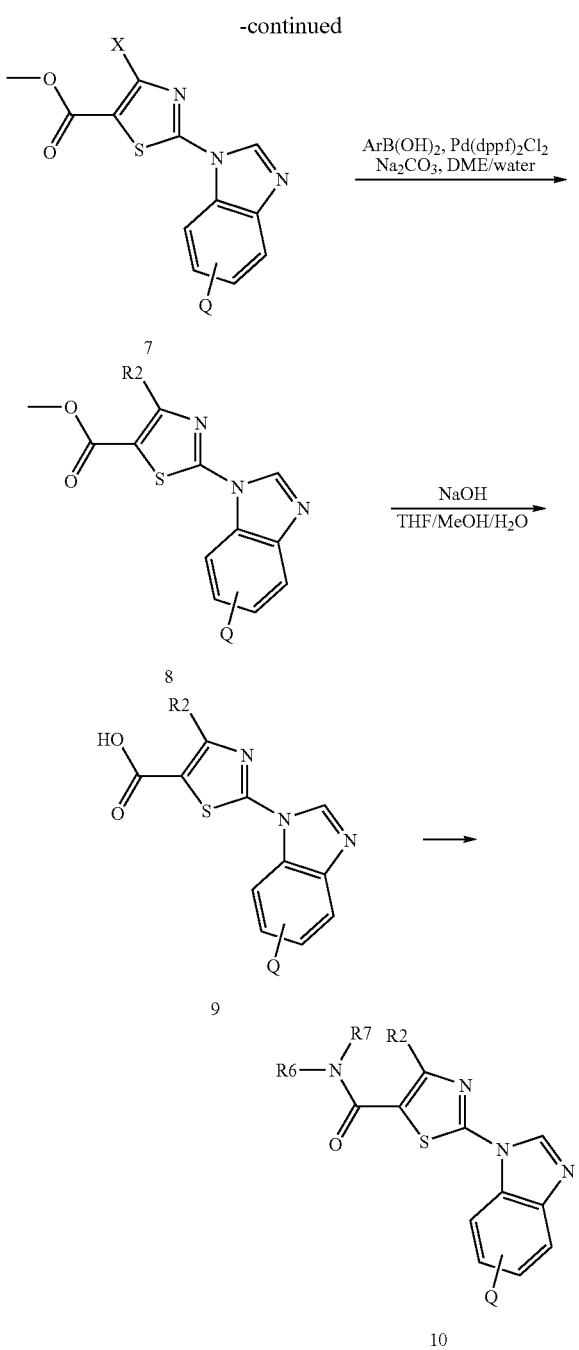

Description of Core Synthesis

A compound of formula 3 may be prepared by halogenation of commercially available starting material 2.

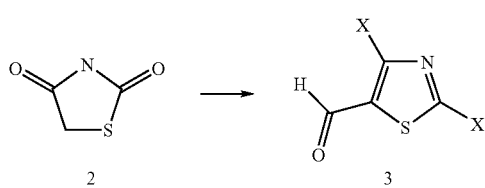

The halogenation reaction may be effected by treatment of a compound of formula 2 (2,4-thiazolidinedione) with phosphorus oxybromide in the presence of DMF. Alternatively, the halogenation reaction may also be effected by treatment of a compound of formula 2 with phosphorus oxychloride in the presence of DMF to form the analogous dichloride.

A compound of formula 5 may be formed by two steps of chemistry as indicated below. A compound of formula 3 may be oxidized to carboxylic acid in presence of an oxidant such as, but not limited to, potassium permanganate in water. Other methods for oxidation of aldehydes known to those skilled in the art may be successfully applied to the oxidation of a compound of formula 3 to produce a compound of formula 4.

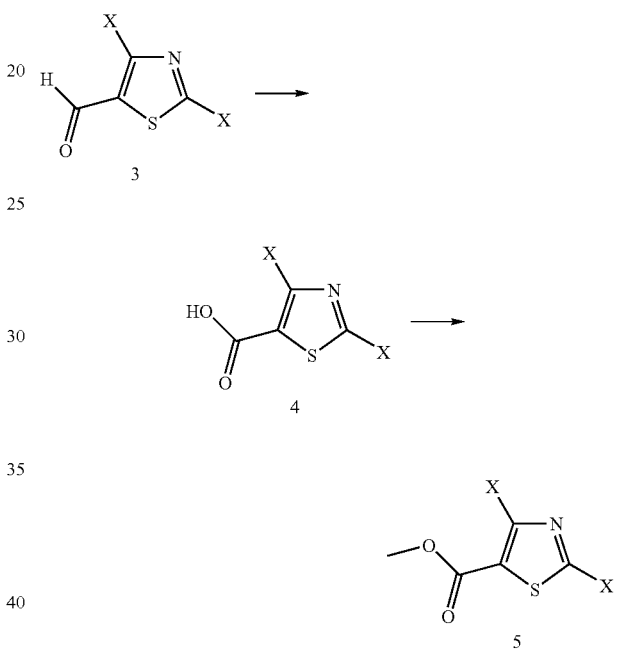

A compound of formula 5 may be produced by esterification of a compound of formula 4. This transformation may be effected by application of reaction conditions such as, but not limited to, reaction with [N-(3-dimethylaminopropyl)-N'-ethylcarbodiimide in methanol. Other methods for formation of lower alkyl esters are available and well known to those skilled in the art.

Description of Chemistry for Benzimidazole Introduction

A compound of formula 7 may be obtained by treatment of a compound of formula 5 with a benzimidazole of formula 6 under basic conditions. A strong base, such as but not limited to, sodium hydride may be used to treat a benzimidazole derivative of formula 6 prior to addition of a compound of formula 5. This reaction may be performed in a solvent and at temperatures such as, but not limited to, N-methylpyrrolidine at 0° Celsius, respectively. Other reaction temperatures may also be useful. The coupling reaction of thiazole 5 and benzimidazole 6 can also be performed by reaction with potassium carbonate in N-methylpyrrolidine or by reaction with lithium hexamethyldisilazide in tetrahydrofuran.

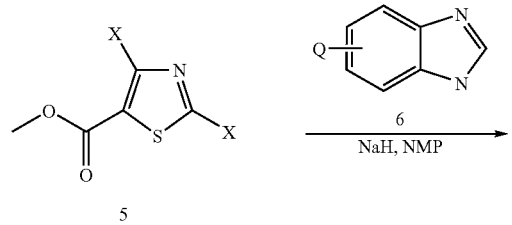
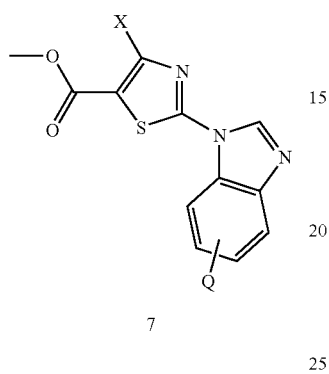
Description of Chemistry for Benzimidazole Formation
The following compounds of formula 6 are commercially available according to the MDL® Available Chemicals Directory and may be useful to this invention.
| STRUCTURE | MDLNUMBER |
|---|---|
| 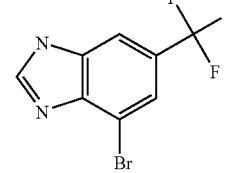 | MFCD00005585 |
| 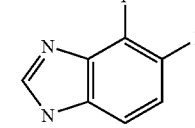 | MFCD00005603 |
| 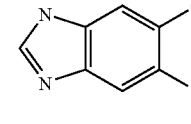 | MFCD00010740 |
| 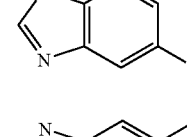 | MFCD00011555 |
| 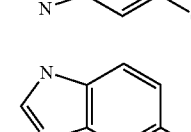 | MFCD00059698 |
| 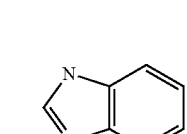 | MFCD00067733 |
-continued
| STRUCTURE | MDLNUMBER |
|---|---|
| 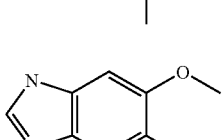 | MFCD00067734 |
| 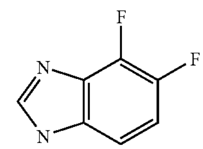 | MFCD00153122 |
| 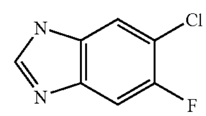 | MFCD00156132 |
| 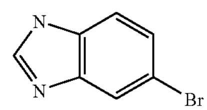 | MFCD00160001 |
| 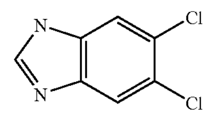 | MFCD00211325 |
| 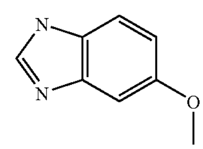 | MFCD00272526 |
| 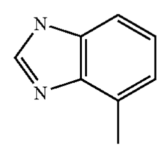 | MFCD00272527 |
| 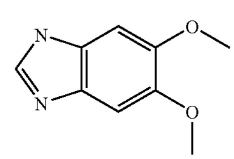 | MFCD00612461 |
| 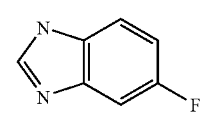 | MFCD00792438 |
| 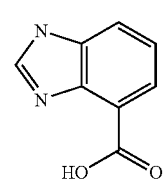 | MFCD01823426 |

| STRUCTURE | MDLNUMBER |
|---|---|
| 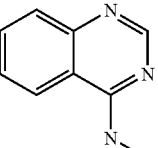 | MFCD02031530 |
| 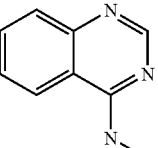 | MFCD02179193 |
| 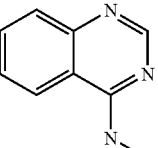 | MFCD02181079 |
| 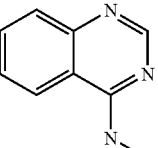 | MFCD02181085 |
| 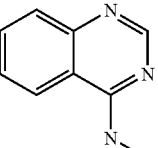 | MFCD03093058 |
| 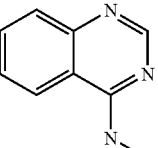 | MFCD03225617 |
| 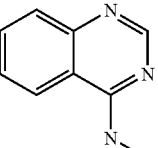 | MFCD03425145 |
| 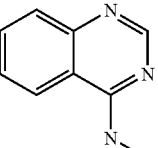 | MFCD04116202 |
| 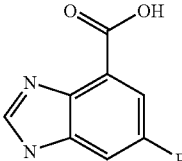 | MFCD06411034 |

| STRUCTURE | MDLNUMBER |
|---|---|
| 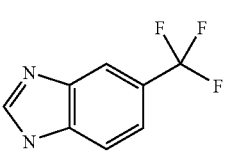 | MFCD06411035 |
| 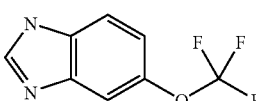 | MFCD06659629 |
| 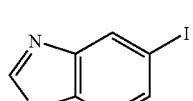 | MFCD06659630 |
| 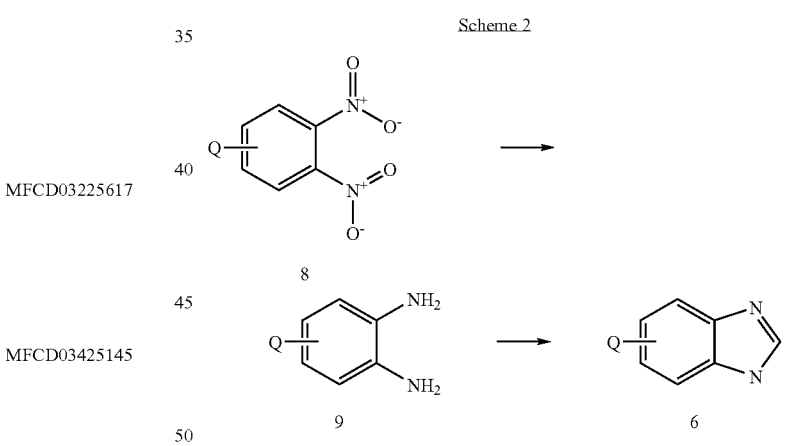 | MFCD06659631 |

Compounds of formula 6 may also be conveniently prepared by conventional reagents and reported synthesis methods. A compound of formula 6 may be synthesized according to the scheme below.

Scheme 2

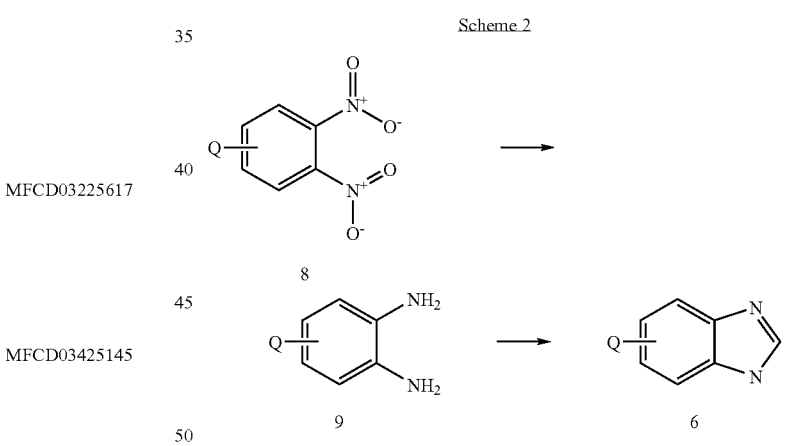

Substituted dinitrobenzene (formula 8) may be reduced to the dianiline (formula 9) in presence of a reductant such as zinc metal in acetic acid. Alternatively, the di-aniline may be obtained by reduction using hydrogen gas in an appropriate solvent, such as methanol, in the presence of an appropriate catalyst, preferably 5% palladium on carbon or platinum oxide. The di-aniline may be reacted with a ring forming reagent, preferably formic acid, to prepare a compound of the formula 6. This method has been reported in the chemical literature using formaldehyde as a ring forming reagent: Synthesis of 2-arylbenzothiazoles and imidazoles using scandium triflate as a catalyst for both a ring closing and an oxidation steps. Itoh, Takashi; Nagata, Kazuhiro; Ishikawa, Hiroyuki; Ohsawa, Akio. School of Pharmaceutical Sciences, Showa University, Tokyo, Japan. Heterocycles (2004), 63(12), 2769-2783. Alternatively, the use of the ring forming reagent of triethylformate has been reported: An efficient procedure for the synthesis of benzimidazole derivatives using Yb(OTf)$_3$ as catalyst under solvent-free conditions. Wang, Limin; Sheng, Jia; Tian, He; Qian, Changtao. Institute of Fine Chemicals, East China University of Science and Technology, Shanghai, Peop. Rep. China. Synthetic Communications (2004), 34(23), 4265-4272.

Appropriately substituted compounds of formula 6 may also be prepared according to the following chemistry scheme 3.

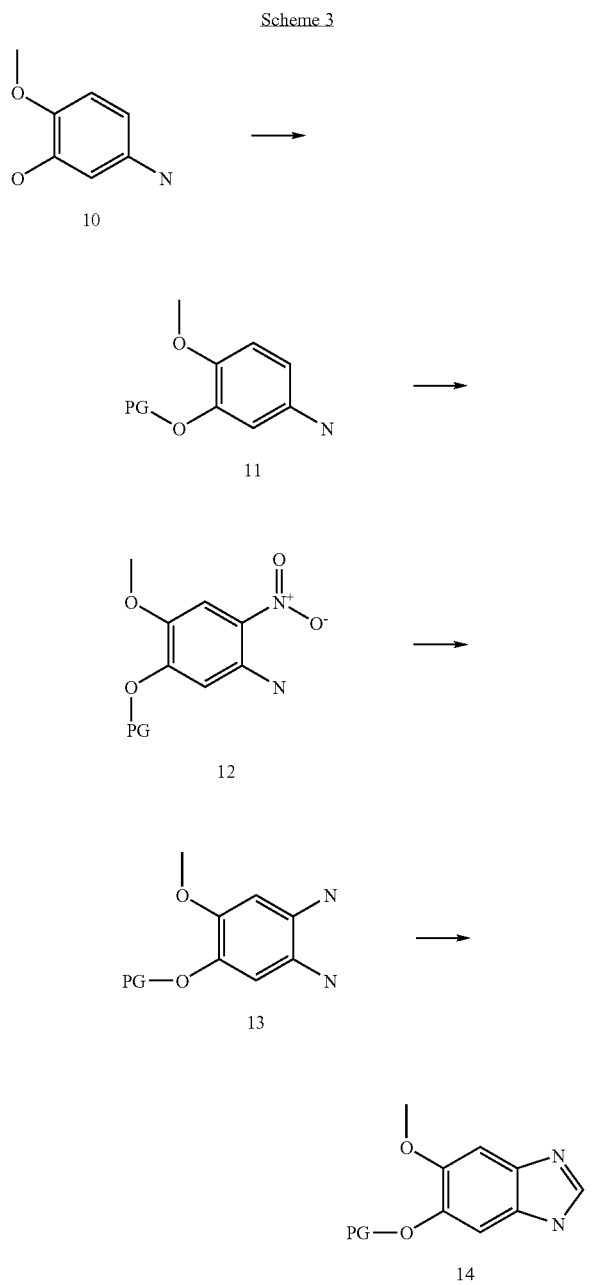

In this method, 3-hydroxy-4-methoxy-aniline (CAS 1687-53-2) may be reacted with a protecting group, preferably but not limited to tert-butyldimethylsilyl chloride generating a compound of formula 11. A compound of formula 11 may be nitrated by treatment with nitric acid, followed by reduction as described above. The resulting di-aniline product may be reacted with a ring forming reagent, as described above, preferably formic acid or a chemically equivalent reagent.

Description of Aryl Coupling Reactions

Compounds of formula 8 may be prepared from compounds of formula 7 by reaction with substituted boronic acids or esters under palladium catalysis conditions.

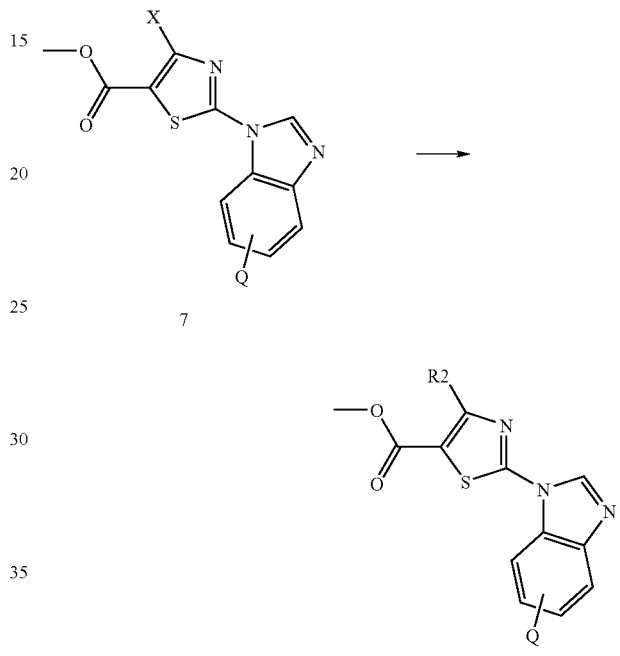

The conditions of this method are disclosed in many publications which have been reviewed by A. Suzuki in an article entitled "The Suzuki reaction with arylboron compounds in arene chemistry" in *Modern Arene Chemistry* 2002, 53-106. In carrying out this reaction any of the conditions conventional in a Suzuki reaction may be utilized.

Generally these reactions are carried out in the presence of a metal catalyst such as a palladium catalyst utilizing any conventional organic solvent and a weak inorganic base. Among the preferred organic solvents are the polar aprotic solvents. Any conventional polar aprotic solvents may be utilized in preparing compounds of the invention. Suitable solvents are customary, especially higher-boiling, solvents, e.g. dimethoxyethane. The weak inorganic base may be a carbonate or bicarbonate, such as potassium carbonate, cesium carbonate.

Commercially Available Boronic Acids Used in This Procedure are Listed Below.

The MDL® Available Chemicals Database (ACD) indicates the availability of greater than seven hundred commercially available aryl boronic acids. Some boronic acids useful for the preparation of compounds of the invention are listed below.

Phenyl boronic acids and boronic esters useful in the preparation of compounds of formula 8 may be commercially available as set out above or they may be made by reactions that are well known in the field of organic synthesis, such as those outlined below. Aryl boronic acids and aryl boronic esters may be formed as set out below in Scheme 5 by treatment of aryl halides (13) with an organometallic reagent such as n-butyl lithium followed by treatment with boron triisopropoxide or 4,4,4',4',5,5,5',5'-octamethyl-2,2'-bi-1,3,2-dioxaborolane followed by acidic work-up as would be well known to those skilled in the art.

| Boronic acid |
|---|
| 3-CHLORO-PHENYLBORONIC ACID |
| 3-CHLORO-5-METHYLPHENYLBORONIC ACID |
| 3-CHLORO-6-METHOXYPHENYLBORONIC ACID |
| 3-CHLORO-4-FLUOROPHENYLBORONIC ACID |
| 3-CHLORO-4-METHYLPHENYLBORONIC ACID |
| 3-CHLORO-2-METHYLPHENYLBORONIC ACID |
| 4-CHLORO-3-METHYLPHENYLBORONIC ACID |
| 2,4-DI-CHLOROPHENYLBORONIC ACID |
| 4-CHLORO-2-METHYLPHENYLBORONIC ACID |
| 4-CHLORO-2-METHOXYLPHENYLBORONIC ACID |
| 4-CHLORO-2-ETHOXYLPHENYLBORONIC ACID |
| 4-CHLORO-3-AMINOPHENYLBORONIC ACID |
| 3-ISOPROPYLPHENYLBORONIC ACID |
| 2,5-DICHLOROPHENYLBORONIC ACID |
| THIOPHENE-3-BORONIC ACID |
| 2-METHYLPHENYLBORONIC ACID |
| 3-METHYLPHENYLBORONIC ACID |
| (2-HYDROXYMETHYLPHENYL)BORONIC ACID DEHYDRATE |
| (3-HYDROXYMETHYLPHENYL)BORONIC ACID DEHYDRATE |
| 4-HYDROXYPHENYL)BORONIC ACID DEHYDRATE |
| 2-METHOXYPHENYLBORONIC ACID |
| 3-METHOXYPHENYLBORONIC ACID |
| 2-TRIFLUOROMETHOXYPHENYLBORONIC ACID |
| 3-TRIFLUOROMETHOXYPHENYLBORONIC ACID |
| 6-FLUORO-2-METHOXYPHENYLBORONIC ACID |
| 2-FLUORO-3-METHOXYPHENYLBORONIC ACID |
| 5-FLUORO-2-METHOXYPHENYLBORONIC ACID |
| 3,4-DIMETHOXYPHENYLBORONIC ACID |
| 2,5-DIMETHOXYPHENYLBORONIC ACID |
| 5-BENZO[1,3]DIOXOLEBORONIC ACID |
| 2,3,4-TRIMETHOXYPHENYLBORONIC ACID |
| 1H-INDOLE-5-BORONIC ACID |
| QUINOLINE-8-BORONIC ACID |

These boronic acids are also available from other suppliers that may not necessarily be listed in the ACD.

Scheme 5

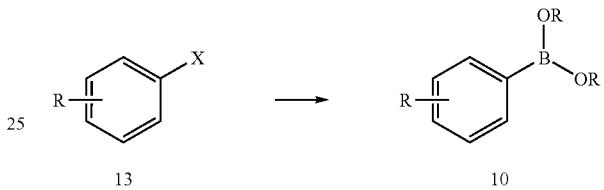

Ester Hydrolysis

Compounds of formula 8 may be hydrolyzed to compounds of formula 9 where X represents hydrogen by treatment with hydrolysis conditions, as set out in Scheme 6.

| 3-Fluoro-6-(4,4,5-tetramethyl-[1,3,2]dioxaborolan-2-yl)pyridine | ATLANTIC SCIENTIFIC CO., INC., JERSEY CITY, NJ, | 791819-04-0 |
| --- | --- | --- |
| Quinoline-2-boronic acid | LANCASTER | 745784-12-7 |
| 3-Chloro-6-(4,4,5-tetramethyl-[1,3,2]dioxaborolan-2-yl)pyridine | ATLANTIC SCIENTIFIC CO., INC., JERSEY CITY, NJ, | 652148-93-1 |
| 6-Chloropyridine-2-boronic acid pinacol ester | INTERCHIM, MONTLUCON, FRANCE | 652148-92-0 |
| Boronic acid, (2-methyl-4-pyrimidinyl)- | CHEMSTEP, TALENCE, FRANCE | 647853-31-4 |
| Boronic acid, (3-methoxy-2-pyridinyl)- | CHEMSTEP, TALENCE, FRANCE | 500707-34-6 |
| Boronic acid, (6-methoxy-2-pyridinyl)- | CHEMSTEP, TALENCE, FRANCE | 372963-51-4 |
| Boronic acid, (6-methyl-2-pyridinyl)- | CHEMSTEP, TALENCE, FRANCE | 372963-50-3 |
| Boronic acid, (5-methyl-2-pyridinyl)- | CHEMSTEP, TALENCE, FRANCE | 372963-49-0 |
| Boronic acid, (4-methyl-2-pyridinyl)- | CHEMSTEP, TALENCE, FRANCE | 372963-48-9 |
| Boronic acid, 2-pyridinyl- | CHEMSTEP, TALENCE, FRANCE | 197958-29-5 |

Scheme 6

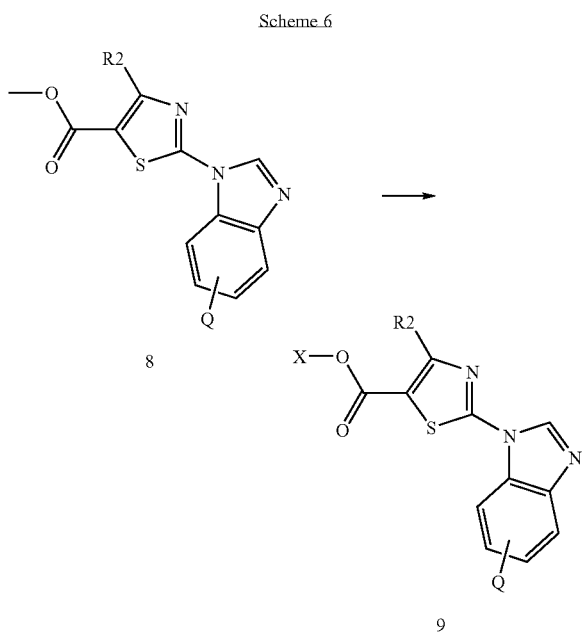

The reaction may be carried out under basic conditions in mixed solvents. Examples of suitable reagents include but are not limited to sodium hydroxide or lithium hydroxide dissolved in solvent such as tetrahydrofuran or methanol either of which contains some quantity of water. The preferable condition is reaction with sodium hydroxide in a solvent mixture of tetrahydrofuran or methanol, and water. The reaction may be carried at various temperatures; it is preferable to conduct the reaction at room temperature.

Amide Formation

Scheme 7

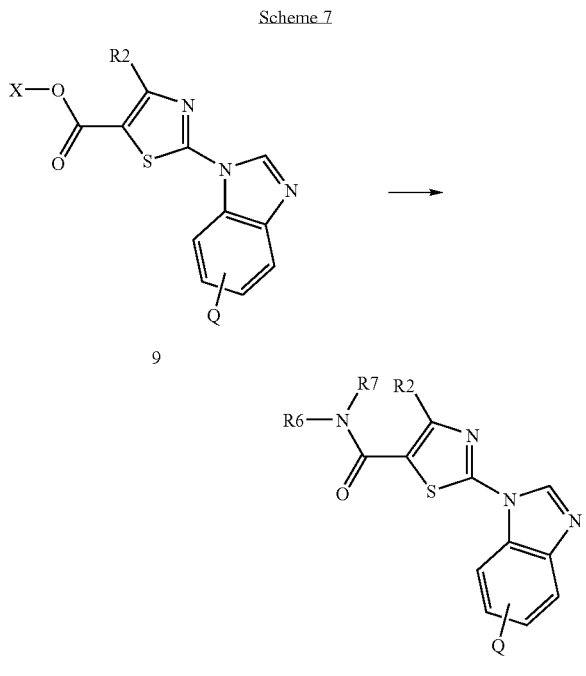

Compounds of formula 10 may be prepared by the coupling of carboxylic acids of structure 9 where X is proton with amines or aryl-hydrazides of structure HNR6R7, according to Scheme 7, may be achieved using methods well known to one of ordinary skill in the art. For example, the transformation may be carried out by reaction of carboxylic acids of structure 9 or of appropriate derivatives thereof such as activated esters, with amines of diverse structure or their corresponding acid addition salts (e.g., the hydrochloride salts) or with aryl-hydrazides in the presence, if necessary, of a coupling agent, many examples of which are well known per se in peptide chemistry. The reaction may be conveniently carried out by treating the carboxylic acid of structure 9 with the hydrochloride of the reacting amine or hydrazide in the presence of an appropriate base, such as diisopropylethylamine, a coupling agent such as O-(benzotriazol-1-yl)-1,1,3,3-tetramethyluronium hexafluorophosphate, and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about 0 degrees and about room temperature, preferably at about room temperature. Alternatively, the reaction may be carried out by converting the carboxylic acid of formula 9 to an activated ester derivative, such as the N-hydroxysuccinimide ester, and subsequently reacting this with an aryl-hydrazide or amine or its corresponding acid addition salt. This reaction sequence can also be carried out by reacting the carboxylic acid of formula 9 with reagents to form its cognate acyl halide, preferably acyl chloride in the presence of base, preferable di-isopropylethyl amine. Acyl chlorides may be conveniently formed by reaction of carboxylic acids of structure 9 with chlorinating reagents, such as thionyl chloride or oxalyl chloride, preferably the latter in dry dichloromethane at a temperature between about 0 degrees and about room temperature.

Compounds of formula 10 may be prepared by coupling the 2,5-dioxo-pyrrolidin-1-yl ester of commercially available 2-aryl-thiazole-5-carboxylic acids with a large number of amines or hydrazides. 5-Dioxo-pyrrolidin-1-yl esters are prepared by reaction of commercially available 2-aryl-thiazole-5-carboxylic acids 1 with TSTU (ethanaminium, N-[(dimethylamino)[(2,5-dioxo-1-pyrrolidinyl)oxy]methylene]-N-methyl-, tetrafluoroborate). The reaction may be conveniently carried out in the presence of an organic base such as triethylamine or diisopropylethylamine. The reaction may be carried out in polar solvents such as mixtures of dimethylformamide and dioxane according to the solubility of the carboxylic acid. The reaction may be carried out at a temperature between about 0 degrees Celsius and about room temperature, preferably at around room temperature. This chemistry may be carried out either in the synthesis of a single compound or in the synthesis of libraries of compounds using automated parallel synthesis methods.

Compounds of formula 10 may also be prepared by the coupling of carboxylate esters of structure 9 where X is lower alkyl such as methyl or ethyl with amines or hydrazides of structure HNR6R7, according to Scheme 7, may be achieved using methods well known to one of ordinary skill in the art. For example, the transformation may be carried out by reaction of carboxylic acid esters of structure 9 with amines or hydrazides of diverse structure or their corresponding acid addition salts (e.g., the hydrochloride salts) in polar solvents such as water or methanol or alkyl at elevated temperature such as 60° C. in the presence of basic catalysis, if necessary.

Many examples of which are well known for ester to amide transformation to those skilled in the art.
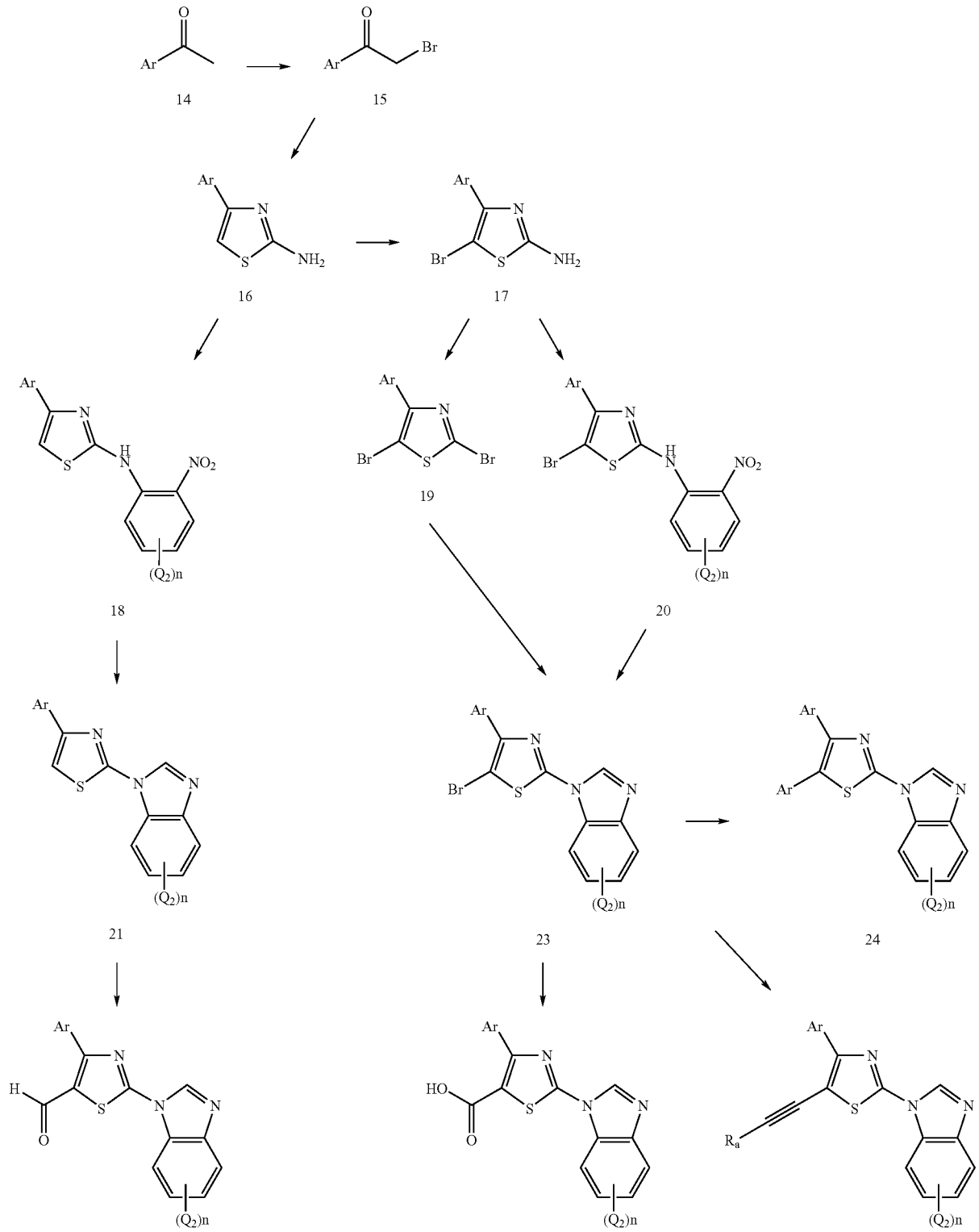

An alternative synthesis of compounds of the invention is shown in Scheme 8. According to this process, an aryl-methyl-ketone of formula 14 may be converted to the bromomethyl ketone of formula 15. This reaction may be carried out by any conventional means, and appropriate methods are well known to one of average skill in the art of organic synthesis. For examples, several methods are enumerated in "Comprehensive Organic Transformations: A Guide to Functional Group Preparations" [R. C. Larock, VCH Publishers, Inc., N.Y. 1989, pages 370-371] and in "Advanced Organic Chemistry" [J. March, 3rd Edition, Wiley Interscience, NY, 1985, pages 529-531]. For example, the reaction may be conveniently carried out by treating the methyl ketone of formula 14 with bromine in a suitable inert solvent such as a halogenated hydrocarbon (e.g., carbon tetrachloride) in the optional presence of other agents that facilitate the reaction, such as a Bronsted or Lewis acid catalyst (e.g., aluminum chloride or acetic acid). The optimal reaction temperature depends on whether or not a catalyst is used. In the case where aluminum chloride is used, the reaction may be conveniently carried out at about 0° C. In the cases where acetic acid is added, or where no catalyst is used, the reaction may be conveniently carried out at a temperature between about room temperature and about 80° C., preferably at about room temperature. Alternatively, methyl ketone of formula 14 may be converted to bromomethylketone of formula 15 by treatment with copper (II) bromide in a suitable unreactive solvent such as ethyl acetate, preferably at the reflux temperature. Suitable reaction conditions may be found in the literature, for example in R. A. Glennon et al. *J. Med. Chem.* 2004, 47, 6034-6041; in C. Ma et al. *J. Am. Chem. Soc.* 2005, 127, 1463-1472; in B. A. Bakke et al. *J. Org. Chem.* 2005, 70, 4338-4345; and in D. L. J. Clive et al. *J. Org. Chem.* 2003, 68, 9247-9254. The aryl-bromomethyl ketone of formula 15 can also be conveniently prepared from the corresponding aryl ketone using polymer-supported pyridinium bromide perbromide. Reactions conditions may be found in the literature, for example in J. Habermann et al. *J. Chem. Soc. Perkin Trans. I* 1999, 2425-2427. As will be clear to one of average skill, there are alternative methods available to prepare the bromomethylketone of formula 15, including but not limited to Friedel-Crafts reactions of an arene with bromoacetyl bromide or bromoacetyl chloride; oxidation of a 2-bromo-1-hydroxyethyl-arene; reaction of a diazomethyl ketone with HBr; treatment of an aryl-lithium with the Weinreb amide derived from acetic acid; and reduction of a dibromomethyl ketone.

The aryl-bromomethyl ketone of formula 15 reacts with thiourea to give a 2-amino-thiazole of formula 16. The reaction may be conveniently carried out by treating the aryl-bromomethyl ketone of formula 15 with thiourea in an inert solvent, such as an alcohol (for example ethanol or isopropyl alcohol) or tetrahydrofuran, at the reflux temperature. Suitable reaction conditions for this reaction may be found in the literature, for example in J. B. Dickey et al. *J. Org. Chem.* 1959, 24, 187-196; in E. B. Knott *J. Chem. Soc.* 1947, 1656-1659; in R. L. McKee and J. D. Thayer *J. Org. Chem.* 1952, 17, 1494-1496; in J. Breinholt et al. *J. Heterocycl. Chem.* 2001, 38, 569-578; in M. Okhubo et al. Chem. Pharm. Bull. 1995; 43, 1497-1504; in Y. Katsura et al. *J. Med. Chem.* 2000, 43, 3315-3321; and in F. Sanchez-Viesca et al. *Heterocycl. Commun.* 2003, 9, 165-170.

The 2-amino-thiazole of formula 16 can then be converted into a 2-amino-5-bromo-thiazole of formula 17 by treatment with a halogenating agent such as bromine, or N-bromosuccinimide. For example, a compound of formula 16 may be treated with N-bromosuccinimide in an inert solvent such as methanol at a temperature between about room temperature and the reflux temperature of the solvent, conveniently at about room temperature. If bromine is used as the halogenating agent, then convenient solvents include dioxane, acetic acid, and methanol, and the reaction may be carried out at a temperature about 70° C. Reaction conditions for this halogenation reaction are well known and detailed conditions may be found in the literature, for example in K. J. Hodgetts and M. T. Kershaw *Org. Lett.* 2002, 4, 1363-1365; in H. Yamamoto et al. *Bioorg. Med. Chem.* 2002, 10, 1535-1545; in J. C. Quada et al. *Bioorg. Med. Chem.* 2001, 9, 2303-2314; in E. Ceulemans et al. *Tetrahedron* 1999, 55, 1977-1988; in C. Bew et al. *J. Chem. Soc. Perkin Trans. I* 1982, 945-948; in L. Forlani and A. Medici *J. Chem. Soc. Perkin Trans. I* 1978, 1169-1171; in H. Tripathy and G. N. Mahapatra *J. Ind. Chem. Soc.* 1975, 52, 766-767; and in M. Bosco et al. *J. Chem. Soc. Perkin Trans. II* 1976, 398-402.

The 2-amino-thiazole of formula 17 can then be converted into a 2,5-dibromo-thiazole of formula 19 using a Sandmeyer-type reaction. This reaction may be carried out either in aqueous solution, using sodium nitrite, or in organic solution using isoamyl nitrite or tert-butyl nitrite. For example, in the case where the reaction is carried out in aqueous solution, the 2-amino-thiazole of formula 17 may be treated with sodium nitrite in the presence of aqueous mineral acid (such as hydrochloric acid or sulfuric acid) to give an intermediate diazonium salt which is not isolated. The diazonium salt may be prepared at a temperature below about 10° C. and preferably below 0° C. The intermediate diazonium salt may then be treated with an alkali metal halide, or more conveniently a copper halide which may be generated in situ. Examples of convenient reagents include copper(I) bromide; copper(II) sulfate/sodium bromide; and potassium bromide. Examples of specific reaction conditions for this transformation may be found in the literature, for example in P. Chen et al. *Bioorg. Med. Chem. Lett.* 2004, 14, 6061-6066; in R. Houssin et al. *J. Med. Chem.* 2002, 45, 533-536; in A. Barton et al. *J. Chem. Soc. Perkin Trans. I* 1982, 159-164; and in T. R. Kelly and F. Lang *J. Org. Chem.* 1996, 61, 4623-4633. In the case where the reaction is carried out in organic solvent, the 2-amino-thiazole of formula 17 may be treated with an alkyl nitrite (preferably isoamyl nitrite or especially tert-butyl nitrite) and a copper bromide salt. The reaction may be carried out using acetonitrile as solvent, and may be carried out initially at room temperature, with the temperature raised to about 65° C. if this is required to drive the reaction toward completion. Examples of specific reaction conditions for this transformation may be found in the literature, for example in D. E. Podhorez et al. U.S. Pat. No. 6,096,898; in R. N. Misra et al. *Bioorg. Med. Chem. Lett.* 2004, 14, 2973-2977; in K. J. Hodgetts and M. T. Kershaw *Org. Lett.* 2002, 4, 1363-1365; and in A. T. Ung and S. G. Pyne *Tetrahedron: Asymm.* 1998, 9, 1395-1407.

The dibromo-thiazole of formula 19 may be conveniently converted into the benzimidazole derivative 23 by displacement of the bromine at the 2-position using reactions analogous to those described above for the preparation of a compound of formula 7.

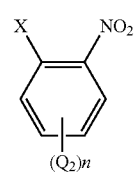

41

Alternatively, the benzimidazole of formula 23 may be prepared in two steps from the aminothiazole derivative of formula 17. In the first step, the amino-thiazole of formula 17 may be converted to the nitro-aniline derivative of formula 20. This reaction may be carried out by any conventional means. For example, the amino-thiazole of formula 17 may be treated with a nitrobenzene derivative of formula 41 where X represents a leaving group such as fluorine or chlorine, in the presence of a base such as potassium carbonate in an inert solvent such as N,N-dimethylacetamide or acetonitrile at a temperature around 80° C. Examples of conditions appropriate for such a reaction may be found in the literature, for example in T. Obata et al. JP 06056808 Chemical Abstracts CAN 121:76161; in J. Das et al. US 20040054186; and in B. S. Jensen et al. U.S. Pat. No. 6,380,180. The nitrobenzene intermediate of formula 20 can then be converted to the benzimidazole of formula 23 using one of a number of procedures that are well known to one of average skill in the art of organic synthesis. For example, the reaction may be effected by reducing the nitro group to an $NH_2$ group using one of several possible reduction procedures (e.g., treatment with tin(II) chloride in an inert solvent such as N,N-dimethylformamide at room temperature, or by hydrogenation in the presence of a noble metal catalyst such as palladium-on-carbon in an alcoholic solvent, such as ethanol). The resulting phenylenediamine derivative can then be treated with formamidine acetate or formic acid in methanol or ethanol or 2-methoxyethanol at reflux to give the benzimidazole. Examples of exact conditions may be found in the literature, for example in N. J. Tom et al. WO 2004113322; in B. M. O'Neill et al. *J. Org. Chem.* 2002, 67, 5869-5875; in H. A. Burch and R. M. Herbst *J. Heterocycl. Chem.* 1966, 3, 198-201; and in B. D. Palmer et al. *J. Med. Chem.* 1999, 42, 2373-2382. The conversion of a nitrobenzene intermediate of formula 20 to a benzimidazole of formula 23 can also be effected in a single step by treating a compound of formula 20 with formic acid and tin(II) chloride dihydrate in a microwave oven, according to the procedure described in D. S. VanVliet et al. *Tetrahedron Lett.* 2005, 46, 6741-6743.

A benzimidazole of formula 23 may be converted to a compound of the invention of formula 1 where R2 represents an aryl group, and R1 represents a heterocycle (that is, a compound of formula 24), using a palladium-catalyzed coupling with an organometallic reagent of formula R1-M, following the well-known reaction conditions of Suzuki, Stille, or Negishi, where M represents boronic acid, boronate ester, trimethyltin, tri-n-butyl-tin, or ZnBr. Further information on the Suzuki reaction may be found in an article by A. Suzuki in *Modern Arene Chemistry*, D. Astruc, Ed.; Wiley-VCH Verlag, Weinheim, 2002, pages 53-106. Further information on the Stille reaction may be found in an article by M. Kosugi and K. Fugami in *Handbook of Organopalladium Chemistry for Organic Synthesis*; E.-I. Negishi, Ed.; John Wiley & Sons, Inc., Hoboken, N.J., 2002, pages 263-283. For example, the reaction may be conveniently carried out by reacting a compound of formula 23 with a compound of formula R1-M where M represents $B(OH)_2$, in a convenient inert solvent such as a polar aprotic solvent (e.g., N,N-dimethylformamide) or an ether (e.g., dioxane) or water, in the presence of a catalytic amount of a palladium(0) complex (e.g., tetrakis(triphenylphos-phine)palladium(0)) or a compound which may be reduced in situ to give palladium(0) (for example, palladium(II) acetate or bis(triphenylphosphine)palladium (II) chloride), in the optional additional presence of a catalytic amount of a phosphine ligand, for example tri-o-tolylphosphine or tri-tert-butylphosphine, or alternatively in the presence of a preformed complex of palladium(0) with a phosphine ligand such as bis(tri-cyclohexylphosphine)palladium, and also in the presence of an inorganic base, for example, an alkali metal carbonate, bicarbonate or phosphate (e.g., potassium phosphate or sodium carbonate) at a temperature between about room temperature and about 100 degrees, and preferably at between about room temperature and about 50 degrees. It is also possible to use an alkali metal hydroxide such as sodium hydroxide or potassium hydroxide as the base in this reaction. Alternatively, the reaction may be carried out by reacting a compound of formula 23 with a compound of formula R1-M where M represents $SnMe_3$ or $SnBu_3$, in a convenient inert solvent such as dioxane, in the presence of a catalytic amount of a palladium(0) complex (e.g., tetrakis (triphenylphosphine)palladium(0)) or a compound which may be reduced in situ to give palladium(0) (for example, palladium(II) acetate or bis(triphenylphosphine)palladium (II)chloride), in the presence of a catalytic amount of a phosphine ligand, for example tri-o-tolylphosphine, at a temperature about 100° C. Another alternative is to carry out the reaction by reacting a compound of formula 23 with an organozinc reagent of formula R1-ZnBr in a convenient inert solvent such as tetrahydrofuran, in the presence of a catalytic amount of a palladium(0) complex (e.g., tetrakis(triphenylphosphine)palladium(0)) or $Cl_2Pd(dppf)\text{-}CH_2Cl_2$), at a temperature about 65° C. Suitable reaction conditions may be found in the literature, for example in J. A. Miller and R. P Farrell *Tetrahedron Lett.* 1998, 39, 6441-6444; and in K. J. Hodgetts and M. T. Kershaw *Org. Lett.* 2002, 4, 1363-1365.

A compound of formula 23 may be converted to a compound of the invention of formula 1 where R1 represents COOH (that is, a compound of formula 27) by lithium-halogen exchange followed by carboxylation. The reaction may be conveniently carried out by treating a cooled solution of a compound of formula 23 in an inert solvent such as tetrahydrofuran with butyllithium at low temperature, for example around −78° C. The resulting solution may then be poured onto dry ice, or else dry carbon dioxide gas may be bubbled through the solution to give a compound of formula 1 where R1 represents COOH.

A number of methods to synthesize 5-formyl-thiazoles of formula 39 will be obvious to one of average skill in the art. For example, a compound of formula 39 may be prepared in three steps from a compound of formula 16. The first reaction may be the conversion of a compound of formula 16 to the nitro-aniline derivative 18 using a reaction analogous to that described above for the preparation of a compound of formula 20 and then a compound of formula 18 may be converted to a compound of formula 21 using a reaction analogous to that described above for the preparation of a compound of formula 23 from a compound of formula 20. Finally, a thiazole of formula 21 may be subjected to the conditions of the Vilesmeier-Haack formylation reaction. For example, the thiazole of formula 21 may be treated with a reagent generated from N,N-dimethylformamide and phosphorus oxychloride in N,N-dimethylformamide as solvent, conveniently at about room temperature to give the 5-formyl-thiazole. Suitable reaction conditions for the Vilsmeier reaction may be found in the literature, for example in H. Meier and R. Petermann *Helv. Chim. Acta* 2004, 87, 1109-1118; in D. W. Gillon et al. *J. Chem. Soc. Perkin Trans. I* 1983, 341-347; and in C. Hahnemann and H. Hartmann *Helv. Chim. Acta* 2003, 86, 1949-1965. Other approaches for the preparation of a compound of formula 39 include (1) palladium-catalyzed carbonylation of the bromo-thiazole of formula 23; (2) treatment of the 5-lithio-thiazole derived from 21 by treatment with strong base, or from 23 by lithium-halogen exchange, with N,N-dimethylformamide, or a similar reagent which is known to transfer a carbonyl group to an organolithium reagent; (3) Raney nickel reduction of the nitrile of formula 30; and (4) conversion of the carboxylic acid of formula 27 to the Weinreb amide of formula 54, and then treating this with lithium aluminum hydride. The palladium-catalyzed carbonylation reaction may be carried out by treating the bromo-thiazole of formula 23 with carbon monoxide gas in the presence of a palladium(0) or palladium(II) catalyst such as tetrakis(triphenylphosphine)palladium(0) or bis(triphenylphosphine)palladium(II) chloride), in the presence of a reducing agent such as tri-butyltin hydride or formic acid, in an inert solvent such as toluene or dimethyl formamide at a temperature about 50-60° C. Suitable conditions may be found in the literature, for example in V. P. Baillargeon and J. K. Stille *J. Am. Chem. Soc.* 1983, 105, 7175-7176; in I. Carelli et al. *Eur. J. Org. Chem.* 1999, 1471-1473; A. Scoenberg and R. F. Heck *J. Am. Chem. Soc.* 1974, 96, 7761-7764; and in I. Pri-Bar and O. Buchman *J. Org. Chem.* 1984, 49, 4009-4011. An alternative is to treat a compound of formula 23 with n-butyl lithium at low temperature (such as −78° C.) in inert solvent such as tetrahydrofuran in order to effect lithium-halogen exchange. The resulting anion may then be treated with N-formyl-morpholine, N-formyl-piperidine, or N,N-dimethylformamide to give the 5-formylthiazole. Conditions for this reaction may be found in the literature, for example in P. Stanetty et al. *J. Org. Chem.* 2005, 70, 567-574; in P. J. Gilligan et al. *Heterocycles* 2003, 60, 1329-1337; in L. N. Lucas et al. *Eur. J. Org. Chem.* 2003, 155-166; and in I. C. Choo et al. *J. Med. Chem.* 2002, 45, 5005-5022. A nitrile of formula 30 may be reduced by hydrogenation in the presence of Raney nickel. The reaction may be conveniently carried out by treating the nitrile with Raney nickel in aqueous formic acid at a temperature about 100° C. For conditions, see C. D. Selassie et al. *J. Med. Chem.* 1998, 41, 4261-4272; Y.-A. Kim *Tetrahedron Lett.* 2003, 44, 2557-2560; and B. Cao et al. *J. Am. Chem. Soc.* 2002, 124, 520-521. The reduction reaction may be carried out using diisobutylaluminum hydride in place of hydrogen/Raney nickel. This reaction may be conveniently carried out by treating the nitrile with diisobutylaluminum hydride in a halogenated hydrocarbon (e.g., dichloromethane) or aromatic hydrocarbon (e.g., toluene or chlorobenzene) at a temperature about 0° C. For details, see C. A. Dvorak et al. *J. Med. Chem* 2005, 48, 2229-2238; X.-Z. Wang et al. *Synlett* 2004, 469-472; or T. Kline et al. *Bioorg. Med. Chem.* 2000, 8, 73-94. As a final but not limiting option, the carboxylic acid of formula 27 may be converted to the N-methoxy-N-methyl amide (the so-called Weinreb amide) of formula 54 by treating the acid with N,O-dimethyl-hydroxylamine hydrochloride in the presence of a base, such as diisopropylethylamine, a coupling agent such as O-(benzotriazol-1-yl)-1,1,3,3-tetramethyluronium hexafluorophosphate, and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about 0 degrees and about room temperature, preferably at about room temperature. The resulting amide can then be converted to the aldehyde by treatment with diisobutylaluminum hydride or lithium aluminum hydride in an inert solvent, such as tetrahydrofuran or dichloromethane, at about 0° C. For appropriate conditions, see S. Nahm and S. M. Weinreb *Tetrahedron Lett.* 1981, 22, 3815-3818 and J. J. Hale et al. *Bioorg. Med. Chem. Lett.* 2004, 14, 3495-3500.

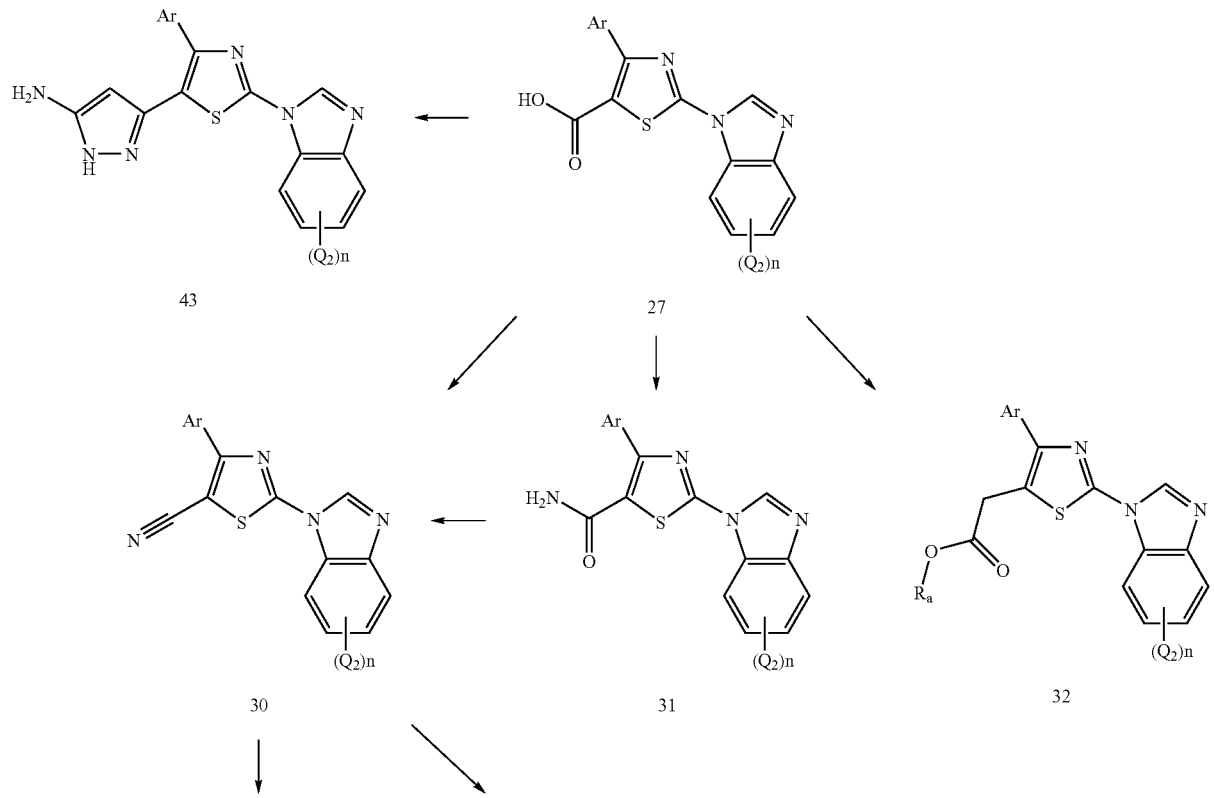

Scheme 8a

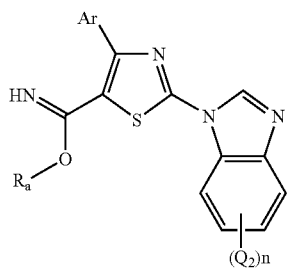

34

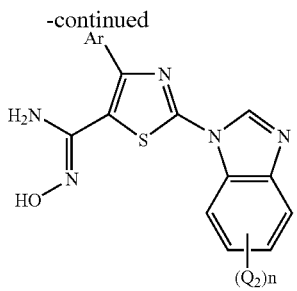

35

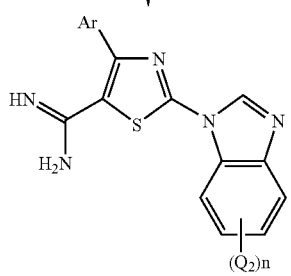

38

A compound of formula 32 where $R_a$ represents hydrogen may be prepared in one step from the acid chloride derived from the carboxylic acid of formula 27 in an Arndt-Eistert reaction (see F. Arndt and B. Eister *Ber. dtsch. Chem. Ges.* 1935, 68, 200-208. According to this process, the carboxylic acid may be converted to the acid chloride by treatment with a chlorinating agent such as thionyl chloride or oxalyl chloride, either neat, or in an inert solvent such as benzene, and the reaction may be conveniently carried out at about room temperature. In the second step of the Arndt-Eistert synthesis, the acid chloride may be treated with diazomethane to give the diazo-ketone, which may be then treated with mercury(I) oxide and silver(I) oxide to give the desired carboxylic acid of formula 32 where $R_a$ represents hydrogen. The acid of formula 32 where $R_a$ represents hydrogen may be conveniently converted to the methyl ester of formula 32 where $R_a$ represents methyl by treating an ethereal solution of the acid with diazomethane. Suitable conditions fro the Arndt-Eistert reaction may be found for example in A. Gaucher, et al. *Tetrahedron Asymmetry* 2005, 16, 857-864; in T. Aoyama et al. *Chem. Pharm. Bull.* 1981, 29, 3249-3255; and in M. N. Samimi et al. *Heterocycles* 1976, 5, 73-75.

A compound of formula 43 may be prepared by any conventional means. For example, it may be prepared from the carboxylic acid of formula 27 by treating the acid with aminoguanidine sulfate and then heating the mixture at about 210° C. to give the triazole of formula 43. Conditions for this reaction may be found in C. A. Lipinski *J. Med. Chem.* 1983, 26, 1-6.

The amide of formula 31 may be conveniently prepared from the carboxylic acid of formula 27 as a particular case of the general reaction described above for the preparation of a compound of formula 10. In this case, R6 and R7 both represent hydrogen.

The nitrile of formula 30 may be prepared from the amide of formula 31 by a dehydration reaction or from a compound of formula 23 by a cyanation reaction. The dehydration reaction may be effected under a variety of conditions that are well known in the art. For example, the amide may be treated with a mixture of oxalyl chloride and dimethylsulfoxide in dichloromethane at low temperature (e.g., −78° C.), followed by the addition of triethylamine. Other dehydration reaction conditions include the following: treatment with pivaloyl chloride and pyridine in dichloromethane at room temperature; treatment with phosphorus oxychloride in pyridine at about 5° C.; and treatment with benzotriazol-1-yl-oxytripyrrolidinophosphonium hexafluorophosphate (PyBOP) and diisopropylethylamine in dichloromethane at about 40° C. Reaction conditions may be found in C. M. Pedersen and M. Bols *Tetrahedron* 2005, 61, 115-122; N. Nakajima et al. *Tetrahedron* 2002, 58, 3561-3578; A. Narsaiah et al. *Adv. Synth. Catal.* 2004, 346, 1271-1274; R. Delaby et al. *Bull. Soc. Chim. France* 1958; 409-414; D. S. Bose et al. *Synthesis* 2001, 373-375; and R. Kusurkar et al. *Indian J. Chem. Sect. B.* 2003, 42, 3148-3151. As a further example, the cyanation reaction may be effected by treating a compound of formula 23 with zinc cyanide in the presence of catalytic tetrakis (triphenylphosphine)palladium(0) in N,N-dimethylformamide under microwave irradiation. For conditions for this reaction, see M. Alterman et al. *J. Org. Chem.* 2000, 65, 7984-7989. A similar palladium-catalyzed cyanation reaction may be run without using microwave irradiation. For examples of conditions, see R. Chidambaram *Tetrahedron Lett.* 2004, 45, 1441-1444; P. E. Maligres et al. *Tetrahedron Lett.* 1999, 40, 8193-8196; D. M. Tschaen et al. *J. Org. Chem.* 1995, 60, 4324-4330; and M.-J. Wu et al. *Tetrahedron* 1999, 55, 13193-13200.

The nitrile of formula 30 may be conveniently converted to the imidate of formula 34 where $R_a$ represents lower alkyl, using a reaction called the Pinner reaction that is well known in the field of organic synthesis. The reaction may be carried out by treating a mixture of the nitrile of formula 30 with a lower alcohol of formula $R_aOH$ with dry hydrogen chloride at about room temperature. Conditions suitable for this reaction may be found in the literature, for example in J. B. Chaires et al. *J. Med. Chem.* 2004, 47, 5729-5742; in J. D. Williams et al. *J. Med. Chem.* 2004, 47, 5766-5772; and in M. Acemoglyu et al. *Tetrahedron* 2004, 60, 11571-11586.

The imidate of formula 34 may be conveniently converted to the amidine of formula 38 by treatment with ammonia. The reaction may be carried out in an alcoholic solvent (e.g., ethanol) and at about room temperature. Conditions suitable for this reaction may be found in the literature, for example in J. B. Chaires et al. *J. Med. Chem.* 2004, 47, 5729-5742; in S. Komoriya et al. *Tetrahedron* 2004, 12, 2099-2114; and in A. Nicolaides et al. *J. Am. Chem. Soc.* 2001, 123, 2628-2636.

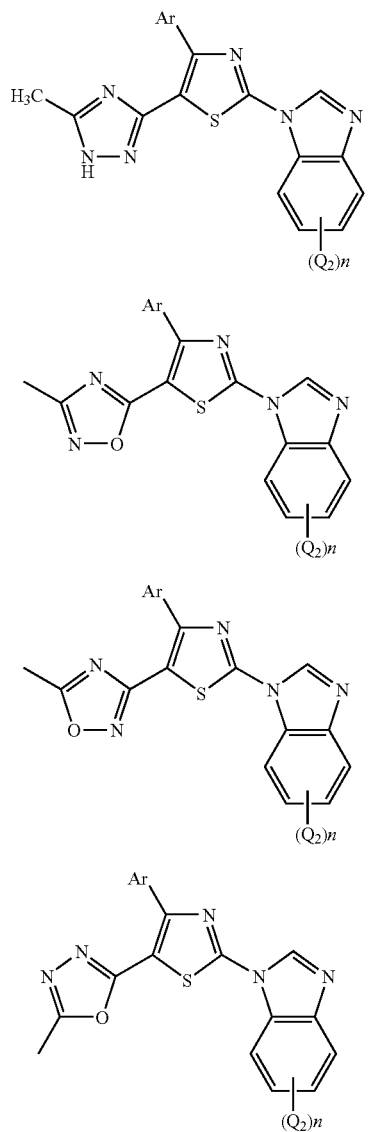

The imidate of formula 34 may be treated with acetic acid hydrazide at reflux in methanol to give the 5-methyl-1,2,4-triazole of formula 44. Conditions for this reaction may be found in the literature, in C. A. Lipinski et al. *J. Med. Chem.* 1985, 28, 1628-1636. The same compound of formula 44 may be prepared starting from the acid of formula 27. Following this procedure, the acid may be activated by reaction with carbonyl diimidazole in tetrahydrofuran at reflux and the resulting acyl imidazolide intermediate may be treated with acetic acid amidrazone, again in tetrahydrofuran at reflux. Conditions for this reaction may be found in the literature, for example in P. H. Olesen et al. *J. Med. Chem.* 2003, 46, 3333-3341.

The nitrile of formula 30 may be converted to the hydroxyamidine of formula 35 by treatment with hydroxylamine hydrochloride in the presence of a base (such as triethylamine) in ethanol or methanol at about 50° C. Alternatively, potassium tert-butoxide may be used as the base, and in this situation, anhydrous DMSO is a convenient solvent and the reaction may be carried out at room temperature. Conditions suitable for this reaction may be found in the literature, for example in P. S. Anderlu et al. *J. Med. Chem.* 2005, 48, 3110-3113; in J. H. Ansede et al. *J. Med. Chem.* 2004, 47, 4335-4338; and in M. A. Ismail et al. *J. Med. Chem.* 2003, 46, 4761-4769.

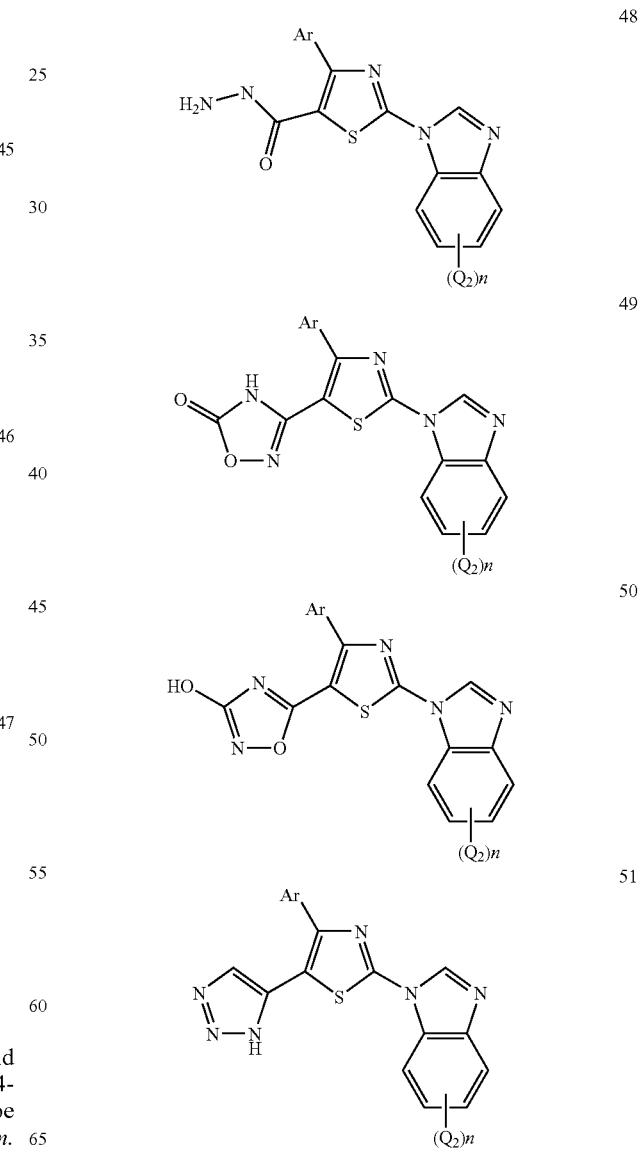

Compounds of the invention of formula 1 where R1 represents an optionally substituted oxadiazole ring may be prepared by reactions that are well known in the field of organic chemistry, several of which are outlined in a publication by B. S. Orlek et al. *J. Med. Chem.* 1991, 34, 2726-2735. For example, for the preparation of the compound of the invention of formula 1 where R1 represents 3-methyl-1,2,4-oxadiazol-5-yl, a compound of formula 31 may be treated with N,N-dimethylacetamide dimethyl acetal at about 120° C. and the resulting acylamidine reacts with hydroxylamine in a mixture of dioxane and acetic acid at about 90° C. to give the desired product. In the case of the compound of the invention of formula 1 where R1 represents 5-methyl-1,2,4-oxadiazol-3-yl, the hydroxyamidine of formula 35 may be treated with acetic anhydride at about 120° C. to give the desired oxadiazole. In the case of the compound of the invention of formula 1 where R1 represents 5-methyl-1,3,4-oxadiazol-2-yl, the hydrazide of formula 48 may be treated with triethyl orthoacetate at about 120° C. to give the desired oxadiazole. The hydrazide of formula 48 may be prepared by treating a solution of the acid of formula 27 in ether with diazomethane to give the methyl ester, and then treating this ester with hydrazine hydrate in ethanol at reflux.

To prepare the compound of the invention of formula 49, the hydroxyamidine of formula 35 may be reacted with a phosgene-equivalent to give the desired 4H-[1,2,4]oxadiazol-5-one. Several examples of suitable phosgene equivalents are well known in the art, including diethyl carbonate (where the reaction may be carried out by treating the hydroxyamidine with the reagent in the presence of sodium hydroxide in ethanol at reflux); 1,1'-carbonyl-diimidazole (where the reaction may be carried out by treating the hydroxyamidine with the reagent in the presence of the base 1,8-diazabicyclo[5.4.0]undec-7-ene in dioxane at reflux); methyl chloroformate or ethyl chloroformate (where the reaction may be carried out by treating the hydroxyamidine with the reagent in pyridine or in the presence of potassium carbonate in acetone and heating at about 125° C. Examples of suitable conditions may be found in the literature in S. Kitamura et al. *J. Med. Chem.* 2001, 44, 2438-2450; in M. H. Gezginci et al. *J. Med. Chem.* 2001, 44, 1560-1563; and in G. D. Diana et al. *J. Med. Chem.* 1994, 37, 2421-2436.

The compound of the invention of formula 50 may be prepared in two steps from a compound of formula 23. The first step involves a palladium-catalyzed coupling reaction known as a Sonogashira reaction to give the acetylene of formula 28 where $R_a$ represents $C(=O)OCH_3$. According to this process a compound of formula 23 may be treated with propargylic acid methyl ester in the presence of a palladium (0) catalyst (or a precursor of palladium(0)) such as tetrakis(triphenylphosphine)palladium(0) or palladium(II) acetate or bis(triphenylphosphine)palladium(II) chloride, in the presence of a catalytic amount of a phosphine ligand, for example tri-o-tolylphosphine, in the presence of an organic base (e.g., triethylamine or diethylamine or diisopropylethylamine) or an inorganic base (for example, an alkali metal carbonate or bicarbonate such as sodium carbonate) and also in the presence of a catalytic amount of copper iodide in a solvent such as tetrahydrofuran at a temperature between about room temperature and about 50° C. Examples of suitable conditions may be found in the literature, for example in R. P. Hsung et al. *Tetrahedron Lett.* 1995, 36, 4525-4528; in K.-L. Yu et al. *Bioorg. Med. Chem. Lett.* 1996, 6, 2859-2864; in T. Eckert and J. Ipaktschi *Synth. Commun.* 1998, 28, 327-336; and in M. de Kort et al. *Eur. J. Org. Chem.* 2000, 3085-3092. The resulting intermediate of formula 28 where $R_a$ represents $C(=O)OCH_3$ may then be treated with hydroxylamine hydrochloride in the presence of base (such as sodium hydroxide) in a solvent such as ethanol/tetrahydrofuran at a temperature about room temperature to give the compound of the invention of formula 50. Examples of suitable conditions may be found in the literature, for example in C. Liljebris et al. *J. Med. Chem* 2002, 45, 1785-1798; in I. Iwai and N. Nakamura *Chem. Pharm. Bull.* 1966, 14, 1277-1286; and in R. G. Micetich and C. G. Chin *Can. J. Chem.* 1970, 48, 1371-1376.

The compound of the invention of formula 51 may be prepared in two steps from the halo-thiazole of formula 23. The first step involves a palladium-catalyzed coupling reaction known as a Sonogashira reaction, similar to the reaction described above. According to this process a compound of formula 23 may be treated with an acetylene derivative that bears one protective group (preferably a 2-hydroxy-propyl or trimethylsilyl group, most preferably a trimethylsilyl group) in the presence of a palladium(0) catalyst (or a precursor of palladium(0) such as tetrakis(triphenylphosphine)palladium(0) or palladium(II) acetate or bis(triphenylphosphine)palladium(II) chloride), in the presence of a catalytic amount of a phosphine ligand, for example tri-o-tolylphosphine, in the presence of an organic (e.g., triethylamine or diethylamine or diisopropylethylamine) or an inorganic base (for example, an alkali metal carbonate or bicarbonate such as sodium carbonate) and also in the presence of a catalytic amount of copper iodide in a solvent such as tetrahydrofuran or diethylamine at a temperature between about room temperature and about 50° C. Examples of suitable conditions may be found in the literature, for example in S. Takahashi et al. *Synthesis* 1980, 627-630; in T. Nussbaumer and R. Neidlein *Heterocycles* 2000, 52, 349-364; in M. S. Khan et al. *J. Chem. Soc. Dalton Trans.* 2002, 2441-2448; and in T. H. M. Jonckers et al. *J. Med. Chem.* 2002, 45, 3497-3508. The acetylene protective group may then be removed to give the intermediate of formula 28 where $R_a$ represents hydrogen. In the case where the protective group is trimethylsilyl, this may be conveniently accomplished by treating the protected acetylene with potassium carbonate in methanol at room temperature. In the case where the protective group is 2-hydroxy-propyl, the deprotection may be achieved by treating the intermediate with sodium hydride in toluene at reflux. The resulting intermediate of formula 28 where $R_a$ represents hydrogen may then be treated with trimethylsilyl-azide either with or without copper catalysis. In the non-catalytic method, the reaction may be carried out in the absence of solvent at a temperature about 170° C. In the catalytic version, the reaction may be carried out in the presence of a copper catalyst (such as copper(II) bromide, copper powder, or preferably copper(I) iodide) in a mixture of N,N-dimethylformamide and methanol at a temperature of about 100° C. Examples of suitable conditions may be found in the literature, for example in T. Jin et al. *Eur. J. Org. Chem* 2004, 3789-3791; and in T. Balle et al. *J. Med. Chem.* 2003, 46, 265-285.

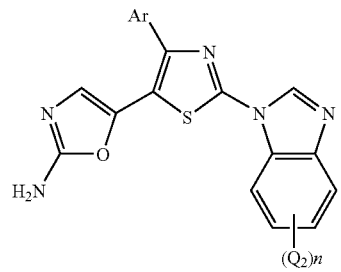

52

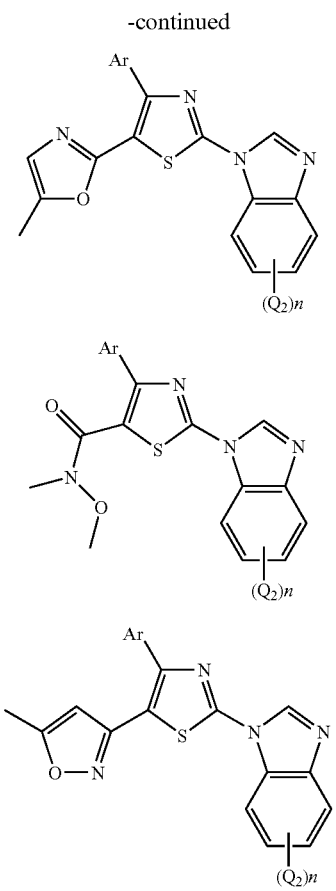

The compound of the invention of formula 52 may be prepared from the aldehyde of formula 39 according to the process of A. M. van Leusen et al. (*J. Org. Chem.* 1981, 46, 2069-2072). The 5-formyl-thiazole of formula 39 may then be treated using van Leusen's conditions with N-(tosylmethyl)-N'-(triphenylmethyl)-carbodiimide in the presence of the phase-transfer catalyst tetra-n-butylammonium bromide in a two-phase mixture of water and dichloromethane at room temperature to give the trityl-protected oxazole. The protective group may be conveniently removed by treatment with concentrated hydrochloric acid in methanol at about 50° C. to give the compound of the invention of formula 52.

A compound of formula 53 may be prepared in two steps from the carboxylic acid of formula 27. In the first step, the carboxylic acid may be converted to the propargyl amide. A large number of reaction conditions are well known to one of skill in the art, and many of these may be used in the current situation. For example, the transformation may be carried out by reaction of carboxylic acid of formula 27 with propargyl amine in the presence of a coupling agent, many examples of which are well known per se in peptide chemistry. The reaction may be conveniently carried out by treating the carboxylic acid of formula 27 with propargyl amine in the presence of a base, such as diisopropylethylamine, a coupling agent such as O-(benzotriazol-1-yl)-1,1,3,3-tetramethyluronium hexafluorophosphate, and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about 0 degrees and about room temperature, preferably at about room temperature. The resulting amide can then be converted to the oxazole using the procedure of A. S. K. Hashmi et al. (*Org. Lett.* 2004, 6, 4391-4394). The reaction may be conveniently carried out by treating the propargyl amide with gold(III) chloride in dichloromethane at about room temperature to give the compound of the invention of formula 53. An alternative approach to the same compound starts with the carboxamide of formula 31. This material may be combined with chloroacetone in toluene and the mixture heated at about 110° C. to give the same product. Conditions for this reaction may be found in A. Hassner and B. Fischer *Tetrahedron* 1989, 45, 6249-6262.

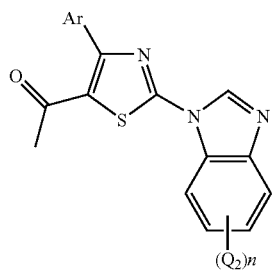

The ketone of formula 26 may be conveniently prepared from the Weinreb amide of formula 54 by treatment with methyl-lithium or methyl-magnesium bromide in an inert solvent such as ether or tetrahydrofuran at about 0° C. Conditions for this reaction may be found in the literature, for example in E. Verner et al. *J. Med. Chem.* 2001, 44, 2753-2771; in L. B. Schenkel and J. A. Ellman *Org. Lett.* 2003, 5, 545-548; and in S. Nahm and S. M. Weinreb *Tetrahedron Lett.* 1981, 22, 3815-3818.

The compound of the invention of formula 55 may be prepared in three steps from the ketone of formula 26. The ketone may be treated with cyclohexylamine in a suitable solvent such as a hydrocarbon (e.g., heptane) at reflux with removal of water in a Dean-Stark trap to give the imine. The imine may then be deprotonated using lithium diisopropylamide at low temperature (for example, −10° C. to about 0° C.) and the resulting anion may be treated with ethyl acetate to give a crude keto-enamine. The keto-enamine reacts with hydroxylamine in a solvent such as water or methanol to give the desired isoxazole. Conditions for such a reaction may be found in the literature, for example in W. H. Bunnelle et al. *Synthesis* 1997, 439-442.

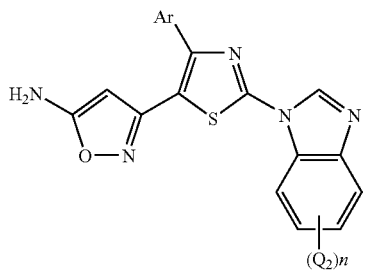

-continued

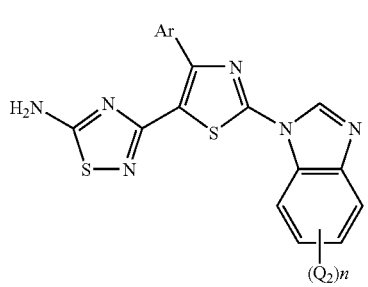

57

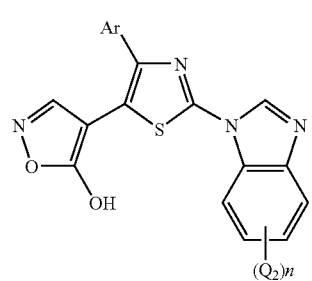

58

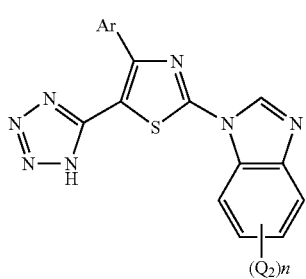

59

The compound of the invention of formula 56 may be prepared in three steps from the carboxylic acid of formula 27. In the first step, the acid may be converted to the methyl ester by treatment with diazomethane, as described above. In the second step, the ester may be treated with acetonitrile in the presence of a strong base such as sodium hydride, in an inert solvent such as tetrahydrofuran at reflux, to give an acyl acetonitrile. Finally, this intermediate may be treated with hydroxylamine hydrochloride in the presence of a base such as sodium acetate in a solvent such as an alcohol (e.g., ethanol) at reflux to give the 5-amino-isoxazole. Conditions for such a reaction may be found in the literature, for example in K. W. Burow U.S. Pat. No. 4,322,429.

The compound of the invention of formula 57 may be prepared in two steps from the amidine of formula 38. The amidine may be treated first with sodium hypobromite in water at 0-5° C. to give the N-bromo-amidine which may be subsequently treated with potassium thiocyanate in refluxing ethanol to give the 5-amino-1,2,4-thiadiazole. Reaction conditions for this reaction may be found in J. Goerdeler et al. Chemische Ber. 1960, 93, 397-405.

The compound of the invention of formula 58 may be prepared in two steps from the methyl ester of formula 32 where $R_a$ represents methyl. According to this process, a compound of formula 32 where $R_a$ represents methyl may be dissolved in ethyl formate and then treated with sodium hydride. The resulting dicarbonyl compound may be dissolved in methanol/water, treated with hydroxylamine hydrochloride, and heated at reflux to give the 5(2H)-isoxazolone.

The compound of the invention of formula 59 may be prepared in one step from the nitrile of formula 30. According to this process, a compound of formula 30 may be treated with sodium azide, and an amine salt (e.g., triethylamine hydrochloride, diethylamine hydrochloride, isoprolyamine hydrochloride, or the like) in an aromatic solvent (e.g., toluene, benzene, xylene, nitrobenzene, or the like) at a temperature about 100° C. to give the tetrazole product. Conditions suitable for this reaction may be found in the literature, for example in K. Koguro et al. Synthesis 1998, 910-914; in M. B. Young et al. J. Med. Chem. 2004, 47, 2995-3008; and in A. Zhang et al. J. Med. Chem. 2004, 47, 165-174. The reaction can also be conducted under microwave irradiation (see M. Alterman et al. J. Org. Chem. 2000, 65, 7984-7989). Alternatively, the reaction may be carried out using trimethylsilyl azide in place of sodium azide. In this case, the reaction may be executed in the absence of solvent but in the presence of a catalytic amount of tetrabutylammonium fluoride. The reaction may be conveniently carried out at a temperature of approximately 85° C. Conditions suitable for this reaction may be found in the literature, for example in D. Amantini et al. J. Org. Chem 2004, 69, 2896-2898; in A. B. Pinkerton et al. Bioorg. Med. Chem. Lett. 2004, 14, 5329-5332; and in M. J. Schulz et al. Org. Lett. 2004, 6, 3265-3268.

Scheme 12

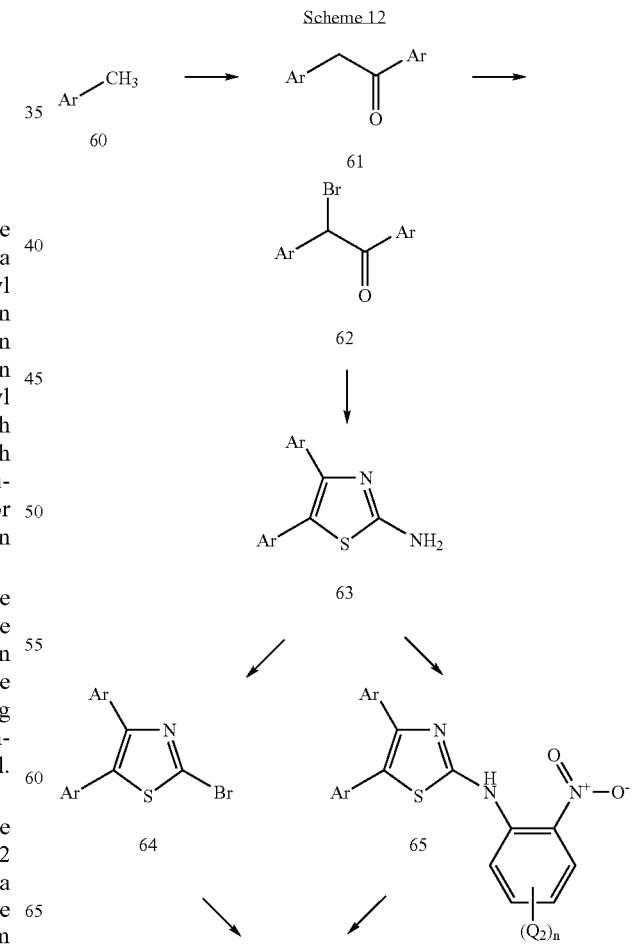

-continued

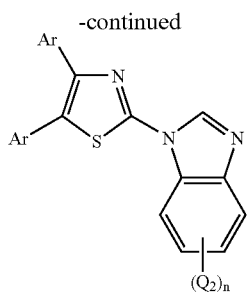

24

An alternative approach to the synthesis of compounds of formula 24 is shown in Scheme 12. According to this approach, a methyl-substituted heterocycle of formula 60 may be acylated to give the ketone of formula 61. This reaction may be carried out using any conventional means. For example, a compound of formula 60 may be conveniently treated with a base, such as sodium amide or potassium amide or lithium diisopropylamide. When sodium amide or potassium amide is used, the base may be conveniently prepared using conventional procedures in ammonia and then the ammonia may be replaced as a solvent by ether. When lithium diisopropylamide is used as a base, a convenient solvent is tetrahydrofuran. Once formed, and without isolation, the base formed from the methyl-substituted heterocycle may be treated with an acylating agent such as an ester of formula ArC(=O)OR$_l$ where R$_l$ represents a lower alkyl group, preferably methyl, or alternatively with an acid anhydride of formula ArC(=O)OC(=O)Ar. The reaction is carried out at a temperature between about room temperature and about 40° C. Suitable conditions for this reaction may be found in the literature, for example in D. R. Howton and D. R. V. Golding *J. Org. Chem.* 1950, 15, 1-7; in A. Ohsawa et al. *Chem. Pharm. Bull.* 1978, 26, 3633-3640; in Jahangir et al. *Can. J. Chem.* 1990, 68, 587-591; and in F. Gellibert et al. *J. Med. Chem.* 2004, 47, 4494-4506. Alternatively, a compound of formula 60 may be treated with ethyl benzoate and potassium ethoxide in ethanol at reflux to give a compound of formula 61. Suitable conditions for this reaction may be found in the literature, for example in A. Dornow and K. Bruncken *Chem. Ber.* 1950, 83, 189-193. As another alternative, a compound of formula 60 may be treated with methyl benzoate and sodium hydride in dimethoxyethane at reflux to give a compound of formula 61. Suitable conditions for this reaction may be found in the literature, for example in J. F. Wolfe et al. *J. Org. Chem.* 1974, 39, 2006-2010.

The ketone of formula 61 may be conveniently converted to a bromo-ketone of formula 62 using one of a number of brominating reactions that are well known in the art. For example, a compound of formula 51 may be treated with pyridinium bromide perbromide in an inert solvent such as tetrahydrofuran at room temperature. Examples of suitable conditions may be seen, for example, in F. Gellibert et al. *J. Med. Chem.* 2004, 47, 4494-4506. or by treatment with bromine and in the optional additional presence of a catalyst such as hydrobromic acid or aluminum chloride in an inert solvent. When aluminum chloride is present, ether may be a convenient solvent; otherwise acetic acid may be a convenient solvent. The reaction may be conveniently carried out at room temperature. Examples of suitable conditions may be seen, for example, in K. C. Rupert et al. *Bioorg. Med. Chem. Lett.* 2003, 13, 347-350; in B. Eister and E. Endres *Liebigs Ann. Chem.* 1970, 734, 56-69; in J. M. Smith, Jr. et al. *J. Am. Chem. Soc.* 1948, 70, 3997-4000.

The bromo-ketone of formula 62 can then be converted to the compound of the invention of formula 24 using reactions that are analogous to reactions described above. For example, the bromo-ketone of formula 62 may be converted to the thiazole of formula 63 using reactions analogous to those described for the preparation of a compound of formula 16. The thiazole of formula 63 may be converted to the bromo-thiazole of formula 64 using reactions analogous to those described for the preparation of a compound of formula 19, and the resulting bromo-thiazole of formula 64 may be converted to the desired thiazole of formula 24 using reactions analogous to those described for the preparation of a compound of formula 23 from the bromo-thiazole of formula 19. Alternatively, the thiazole of formula 63 may be converted to the aniline derivative of formula 65 by reactions analogous to those described for the preparation of compounds of formula 20, and a compound of formula 65 can then be converted to the thiazole of formula 24 using reactions analogous to those described for the preparation of a compound of formula 23 from the aniline derivative of formula 20.

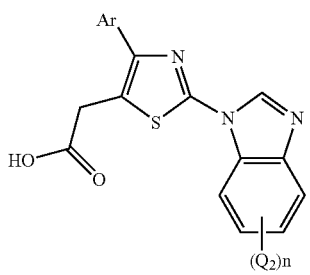

71

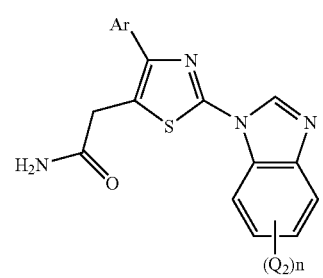

72

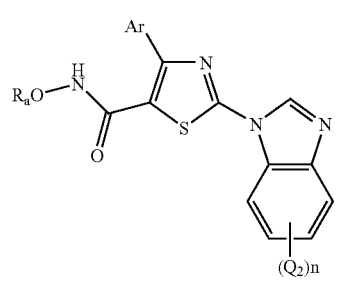

73

The carboxylic acid of formula 71 may be conveniently prepared from the ester of formula 32 by hydrolysis. This reaction is well known in the art and a selection may be made from a variety of conditions to carry it out. For example, the ester of formula 32 may be treated with an alkali metal hydroxide such as sodium hydroxide or lithium hydroxide in aqueous solution, or preferably in a mixture of water and tetrahydrofuran. The reaction may be carried out between about 0° C. and the reflux temperature, conveniently at about room temperature.

The amide of formula 72 may be conveniently prepared from the carboxylic acid of formula 71 by treatment with ammonia or an acid addition salt of ammonia such as ammonium chloride in the presence of a coupling reagent, many of which are well know in the art of chemistry, and especially in the art of peptide chemistry. For example, the carboxylic acid of formula 71 may be treated with ammonia or ammonium chloride in the presence of an appropriate base, such as diisopropylethylamine, in the presence of a coupling agent such as O-(benzotriazol-1-yl)-1,1,3,3-tetramethyluronium hexafluorophosphate, and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about 0 degrees and about room temperature, preferably at about room temperature The hydroxamic acid derivative of formula 73 where $R_a$ represents hydrogen or lower-alkyl may be conveniently prepared from the carboxylic acid of formula 27. The carboxylic acid may be treated with hydroxylamine hydrochloride (to prepare a compound of formula 73 where $R_a$ represents hydrogen) or a lower-alkoxy-amine hydrochloride (to prepare a compound of formula 73 where $R_a$ represents lower-alkyl) in the presence of an appropriate base, such as diisopropylethylamine, and in the presence of a coupling agent such as O-(benzotriazol-1-yl)-1,1,3,3-tetramethyluronium hexafluorophosphate, and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about 0 degrees and about room temperature, preferably at about room temperature The cyano-amide derivative of formula 74 may be conveniently prepared in two steps from the carboxylic acid of formula 27. In the first step, the carboxylic acid of formula 27 may be converted to an activated derivative such as an acid chloride, or an anhydride, or an acid fluoride. This may be done by reacting a compound of formula 27 with a reagent that is commonly used for the conversion of carboxylic acids to acid chlorides such as thionyl chloride or oxalyl chloride in the presence or absence of an inert solvent such as an aromatic hydrocarbon (e.g., benzene) or dichloromethane. In the case where thionyl chloride is used, the reaction may be carried out at a temperature of about 80 degrees. In the case where oxalyl chloride is used, the reaction may be conveniently carried out at a temperature about room temperature. The acid chloride (or other activated acid derivative) may then be treated with cyanamide in the presence of a base such as sodium hydroxide in aqueous solution. Conditions suitable for this reaction may be found in the literature, for example in C. T. Supuran et al. *J. Enz. Inhib.* 1999, 14, 289-306; and in J. Dannheim et al. EP 601416.

The trifluoroethyl alcohol of formula 76 may be conveniently prepared from the bromo-thiazole of formula 23. According to this process, the bromo-thiazole of formula 23 may be converted to the corresponding organolithium reagent by reaction with butyl-lithium in tetrahydrofuran at room temperature, followed by treatment with ethyl trifluoroacetate to give the trifluoromethyl ketone. This ketone may be then reduced by treatment with sodium borohydride in methanol at room temperature to give the trifluoroethyl alcohol of formula 76. It will be obvious to one of skill in the art that there are alternative reagents that could be used to effect the reduction of the ketone, including but not limited to lithium aluminum hydride and Red-Al. Conditions appropriate for this transformation may be found in the literature, for example in A. Gossauer et al. *J. Am. Chem. Soc.* 2004, 126, 1772-1780. Alternatively, the trifluoroethyl alcohol of formula 76 may be conveniently prepared from the thiazole-carboxaldehyde of formula 39 by treatment with a trifluoromethylating agent such as trimethyl(trifluoromethyl)silane in an inert solvent such as N,N-dimethylformamide at about room temperature. Conditions appropriate for this reaction may be found in G. K. Surya Prakash et al. *J. Am. Chem. Soc.* 1989, 111, 393

Preparation of Mono-Substituted Isomers of Benzimidazole Analogs

In this method, ester compounds of general structure 88 and 89 may be synthesized according to Scheme 14. In this method, an isomeric mixture of 2-(5-Methoxy-benzoimidazol-1-yl)-4-R2-thiazole-5-carboxylic acid ethyl ester or other ester and 2-(6-methoxy-benzoimidazol-1-yl)-4-R2-thiazole-5-carboxylic acid ethyl ester or other ester may be separated by re-crystallization or by chromatographic means such as with the application of super critical fluid chromatography. The resultant, separate isomers are treated with a de-methylating agent such as boron tribromide and then subsequently with an alkylating agent Ra—X where X is a leaving group. It is then possible to saponify the ester derivatives to obtain the acids which may also be further derivatized to, e.g., amides such as described above.

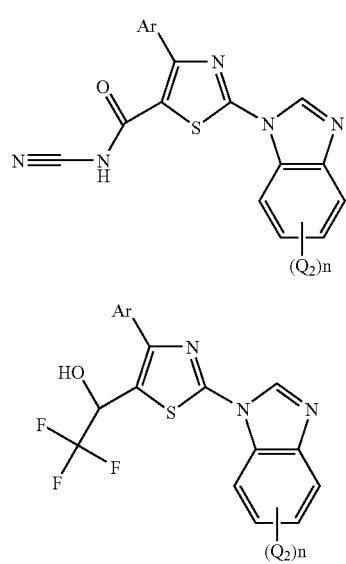

Scheme 14

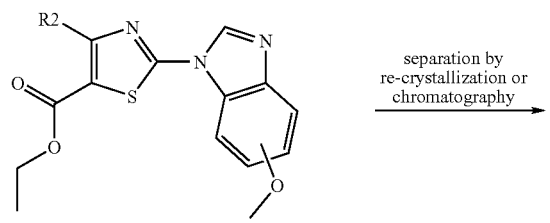
83

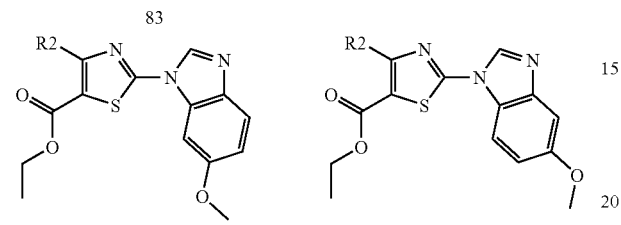
84    85

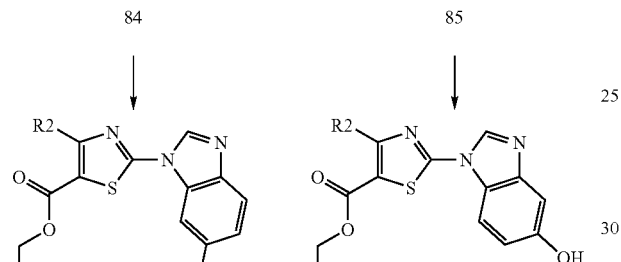
86    87

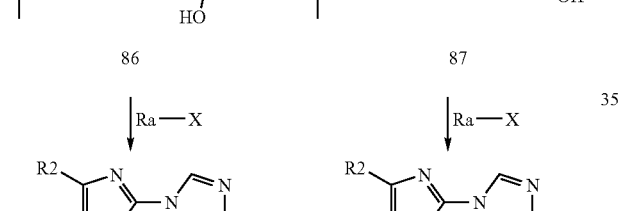

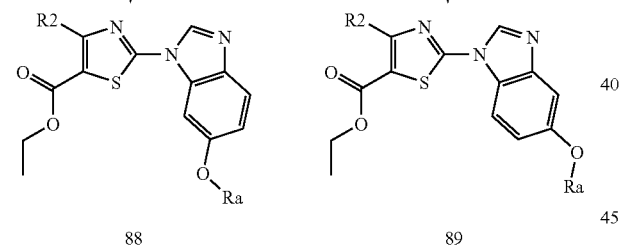
88    89

Description of Preparation of 5-,6-Di-Substituted Isomers of Benzimidazole Analogs In this method, an ester compound of general structure 95 may be synthesized according to Scheme 15. In this method, 2-(5,6-dimethoxy-benzoimidazol-1-yl)-4-phenyl-thiazole-5-carboxylic acid ethyl ester or other ester may be treated with a de-methylating agent such as boron tribromide and then subsequently with pivaloyl chloride or similar pivaloyl reagent to effect the formation of a pivaloate ester 92. Compound 92 may then be treated with an alkylating agent Ra—X where X is a leaving group, generating compound 93. Compound 93 may be then treated with ester cleavage conditions such as with sodium ethoxide in ethanol to generate Compound 94. Compound 94 may be then treated under alkylation conditions to introduce Rb and give Compound 95. It is then possible to saponify the ester derivatives to obtain the acids which may also be further derivatized for example amides as described above.

Scheme 15

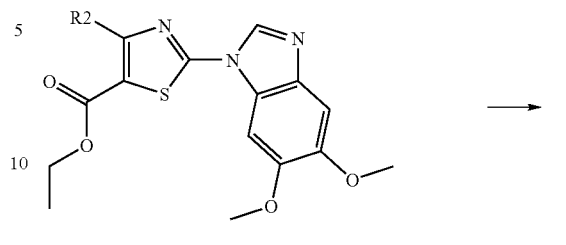
90

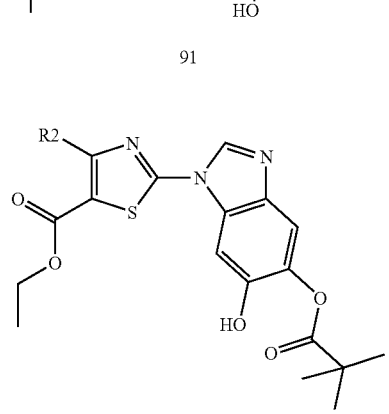
91

92

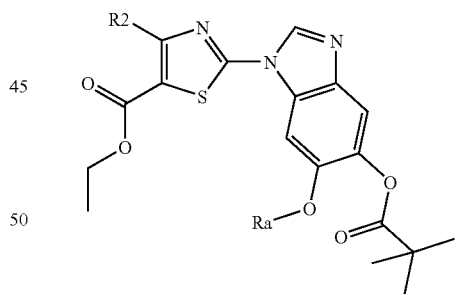
93

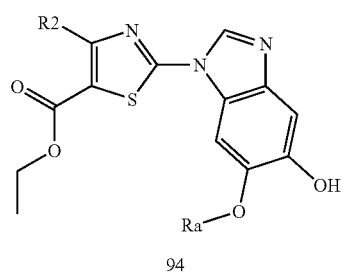
94

-continued

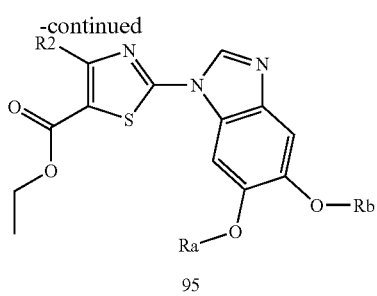

95

The following Examples serve to illustrate the present invention in more detail. They are, however, not intended to limit its scope in any manner.

Experimental Protocols and Examples

Biochemical Characterization Assay: Materials and Methods

Full-length, active GST-Plk1 was purified from Sf9 insect cells, and full-length GST-p53 was purified in *E. coli*. Anti-phospho p53 antibody was purchased from Cell Signaling Technology. Europium-conjugated anti-rabbit antibody was purchased from PerkinElmer Life and Analytical Sciences. APC-conjugated anti-GST antibody was purchased from Prozyme.

To two microliters of compound (0.6 nM-4 mM) in DMSO or plain DMSO for control wells, 38 microliters of 20 mM HEPES pH 7, 50 mM NaCl, 10 mM $MgCl_2$, 0.5 mM TCEP, 0.1 mM sodium orthovanadate, 0.1 mg/ml BSA, and 0.05% Triton X-100 (Kinase Assay Buffer) were added. Eight microliters of the compound solution were added to a 384-well black microtiter plate, followed by six microliters of GST-p53 (17 ug/ml) and ATP (333 uM) in Kinase Assay Buffer. Six microliters of GST-Plk1 (3 ug/ml) in Kinase Assay Buffer were then added and the solution incubated at 37° C. for 35 minutes. Six microliters of solution containing 43 mM EDTA to stop the reaction and a 1:600 dilution of anti-phospho-p53 antibody in 20 mM HEPES pH 7, 50 mM NaCl, and 0.5 mg/ml BSA (Antibody Binding Buffer) were added and the solution incubated at 37° C. for 30 minutes. Six microliters of solution containing 9 nM europium-conjugated anti-rabbit antibody and 120 nM APC-conjugated anti-GST antibody in Antibody Binding Buffer were then added and the mixture incubated at room temperature for 1.5 hours. The HTRF signal was read on the Envision reader (PerkinElmer Life and Analytical Sciences).

Results of Biochemical Assays:

| Example # | Structure | Systematic Name | IC50 (µM) |
|---|---|---|---|
| Example 1 | 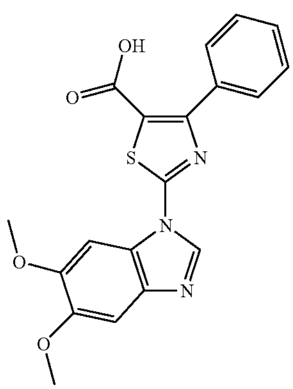 | 2-(5,6-Dimethoxy-benzoimidazol-1-yl)-4-phenyl-thiazole-5-carboxylic acid | IC50 = 0.107 |
| Example 2 | 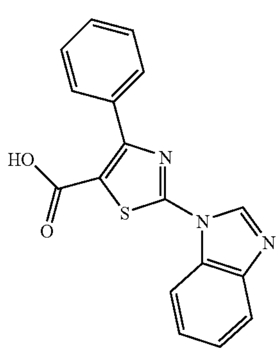 | 2-Benzoimidazol-1-yl-4-phenyl-thiazole-5-carboxylic acid | IC50 = 0.772 |

-continued

| Example # | Structure | Systematic Name | IC50 (μM) |
|---|---|---|---|
| Example 3 | 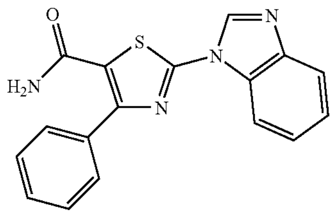 | 2-Benzoimidazol-1-yl-4-phenyl-thiazole-5-carboxylic acid amide | IC50 = 7.362 |
| Example 4 | | 2-(5-Methyl-benzoimidazol-1-yl)-4-phenyl-thiazole-5-carboxylic acid | IC50 = 1.554 |
| Example 5 | 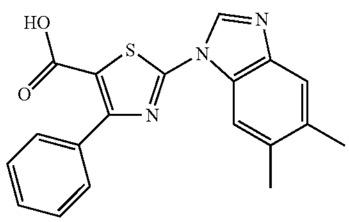 | 2-(5,6-Dimethyl-benzoimidazol-1-yl)-4-phenyl-thiazole-5-carboxylic acid | IC50 = 2.487 |
| Example 6 | 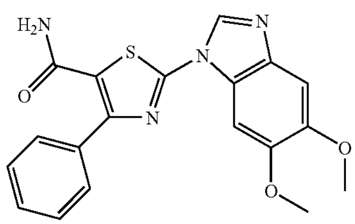 | 2-(5,6-Dimethoxy-benzoimidazol-1-yl)-4-phenyl-thiazole-5-carboxylic acid amide | IC50 = 1.384 |
| Example 7 | | 2-(4-Hydroxy-benzoimidazol-1-yl)-4-phenyl-thiazole-5-carboxylic acid | IC50 = 7.473 |
| Example 8 | | 1-(5-Carboxy-4-phenyl-thiazol-2-yl)-1H-benzoimidazole-4-carboxylic acid | IC50 = 6.423 |
| Example 9 | | 2-(8H-5,7-Dioxa-1,3-diaza-cyclopenta[b]naphthalen-3-yl)-4-phenyl-thiazole-5-carboxylic acid | IC50 = 2.617 |

| Example # | Structure | Systematic Name | IC50 (μM) |
|---|---|---|---|
| Example 10 | 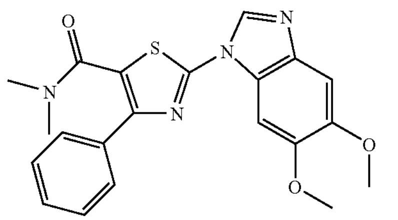 | 2-(5,6-Dimethoxy-benzoimidazol-1-yl)-4-phenyl-thiazole-5-carboxylic acid dimethylamide | IC50 = 1.385 |
| Example 11 | 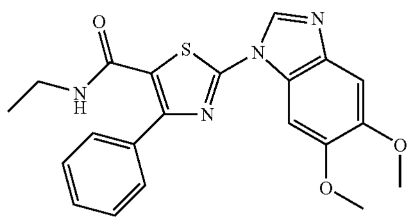 | 2-(5,6-Dimethoxy-benzoimidazol-1-yl)-4-phenyl-thiazole-5-carboxylic acid ethylamide | IC50 = 0.916 |
| Example 12 | 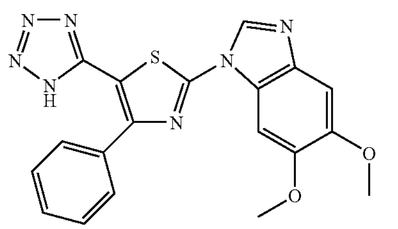 | 5,6-Dimethoxy-1-[4-phenyl-5-(1H-tetrazol-5-yl)-thiazol-2-yl]-1H-benzoimidazole | IC50 = 1.099 |
| Example 13 | 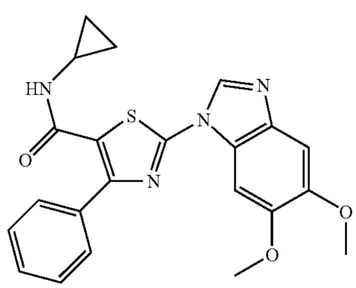 | 2-(5,6-Dimethoxy-benzoimidazol-1-yl)-4-phenyl-thiazole-5-carboxylic acid cyclopropylamide | IC50 = 3.313 |
| Example 14 | | 2-(5-Chloro-benzoimidazol-1-yl)-4-phenyl-thiazole-5-carboxylic acid; compound with 2-(6-chloro-benzoimidazol-1-yl)-4-phenyl-thiazole-5-carboxylic acid | IC50 = 0.72 |
| Example 15 | | 2-(5-Methoxy-benzoimidazol-1-yl)-4-phenyl-thiazole-5-carboxylic acid; compound with 2-(6-methoxy-benzoimidazol-1-yl)-4-phenyl-thiazole-5-carboxylic acid | IC50 = 0.226 |

-continued

| Example # | Structure | Systematic Name | IC50 (μM) |
|---|---|---|---|
| Example 16 | | 2-(5-Chloro-6-methyl-benzoimidazol-1-yl)-4-phenyl-thiazole-5-carboxylic acid; compound with 2-(6-chloro-5-methyl-benzoimidazol-1-yl)-4-phenyl-thiazole-5-carboxylic acid | IC50 = 1.171 |
| Example 17 | 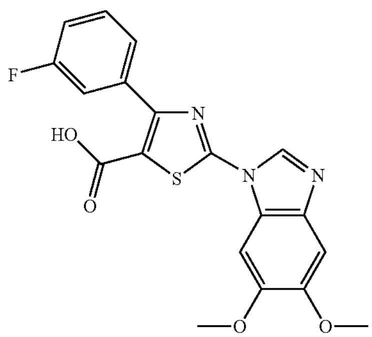 | 2-(5,6-Dimethoxy-benzoimidazol-1-yl)-4-(3-fluoro-phenyl)-thiazole-5-carboxylic acid | IC50 = 0.069 |
| Example 18 | 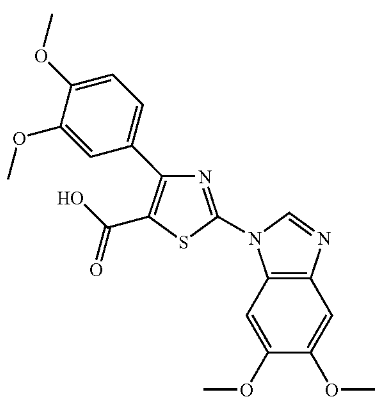 | 2-(5,6-Dimethoxy-benzoimidazol-1-yl)-4-(3,4-dimethoxy-phenyl)-thiazole-5-carboxylic acid | IC50 = 2.389 |
| Example 19 | 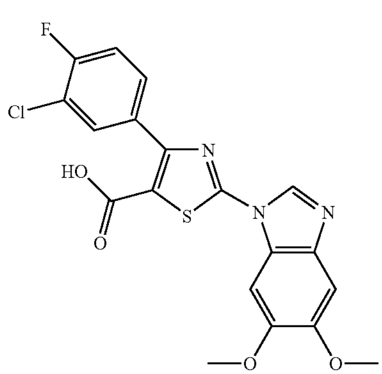 | 4-(3-Chloro-4-fluoro-phenyl)-2-(5,6-dimethoxy-benzo-imidazol-1-yl)-thiazole-5-carboxylic acid | IC50 = 0.087 |

-continued

| Example # | Structure | Systematic Name | IC50 (μM) |
|---|---|---|---|
| Example 20 | 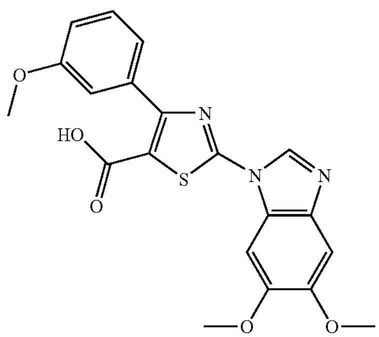 | 2-(5,6-Dimethoxy-benzoimidazol-1-yl)-4-(3-methoxy-phenyl)-thiazole-5-carboxylic acid | IC50 = 0.127 |
| Example 21 | 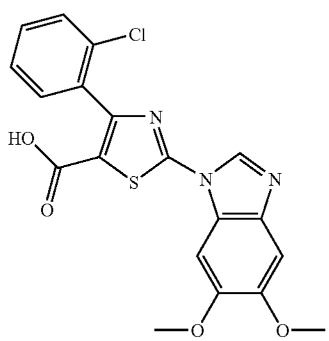 | 4-(2-Chloro-phenyl)-2-(5,6-dimethoxy-benzoimidazol-1-yl)-thiazole-5-carboxylic acid | IC50 = 3.601 |
| Example 22 | 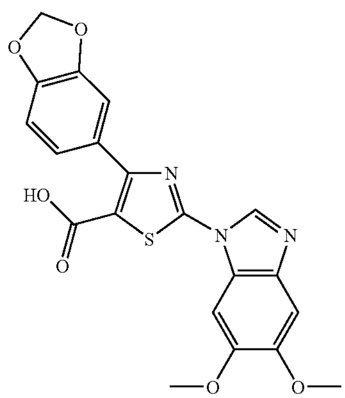 | 4-Benzo[1,3]dioxol-5-yl-2-(5,6-dimethoxy-benzoimidazol-1-yl)-thiazole-5-carboxylic acid | IC50 = 0.125 |
| Example 23 | 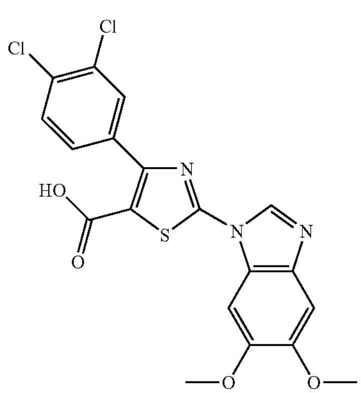 | 4-(3,4-Dichloro-phenyl)-2-(5,6-dimethoxy-benzoimidazol-1-yl)-thiazole-5-carboxylic acid | IC50 = 0.216 |

-continued

| Example # | Structure | Systematic Name | IC50 (μM) |
|---|---|---|---|
| Example 24 | 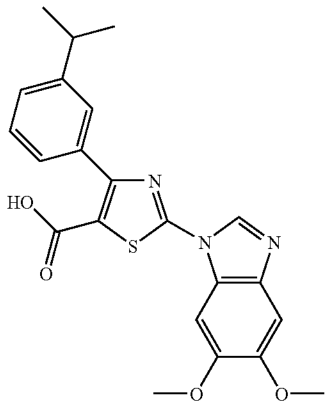 | 2-(5,6-Dimethoxy-benzoimidazol-1-yl)-4-(3-isopropyl-phenyl)-thiazole-5-carboxylic acid | IC50 = 0.068 |
| Example 25 | 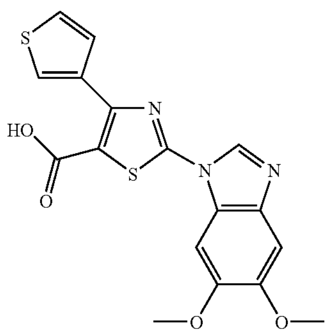 | 2-(5,6-Dimethoxy-benzoimidazol-1-yl)-4-thiophen-3-yl-thiazole-5-carboxylic acid | IC50 = 0.781 |
| Example 26 | 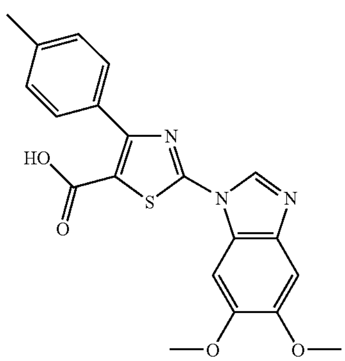 | 2-(5,6-Dimethoxy-benzoimidazol-1-yl)-4-p-tolyl-thiazole-5-carboxylic acid | IC50 = 0.657 |
| Example 27 | 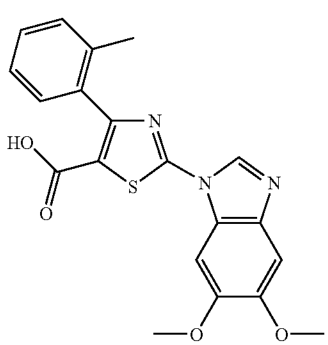 | 2-(5,6-Dimethoxy-benzoimidazol-1-yl)-4-o-tolyl-thiazole-5-carboxylic acid | IC50 = 1.618 |

-continued

| Example # | Structure | Systematic Name | IC50 (μM) |
|---|---|---|---|
| Example 28 | 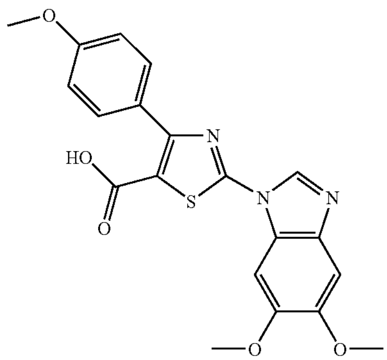 | 2-(5,6-Dimethoxy-benzoimidazol-1-yl)-4-(4-methoxy-phenyl)-thiazole-5-carboxylic acid | IC50 = 0.856 |
| Example 29 | 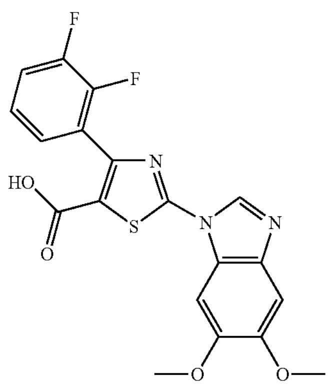 | 4-(2,3-Difluoro-phenyl)-2-(5,6-dimethoxy-benzoimidazol-1-yl)-thiazole-5-carboxylic acid | IC50 = 0.538 |
| Example 30 | 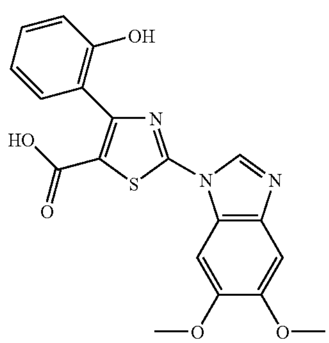 | 2-(5,6-Dimethoxy-benzoimidazol-1-yl)-4-(2-hydroxy-phenyl)-thiazole-5-carboxylic acid | IC50 = 0.275 |
| Example 31 | 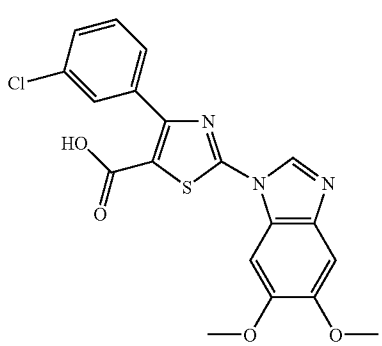 | 4-(3-Chloro-phenyl)-2-(5,6-dimethoxy-benzoimidazol-1-yl)-thiazole-5-carboxylic acid | IC50 = 0.025 |

-continued

| Example # | Structure | Systematic Name | IC50 (μM) |
|---|---|---|---|
| Example 32 | 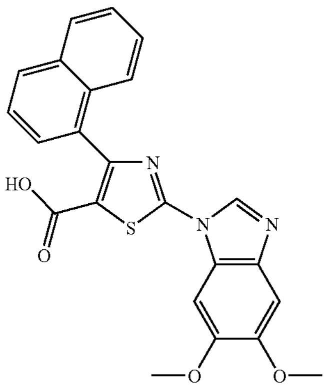 | 2-(5,6-Dimethoxy-benzoimidazol-1-yl)-4-naphthalen-1-yl-thiazole-5-carboxylic acid | IC50 = 3.177 |
| Example 33 | 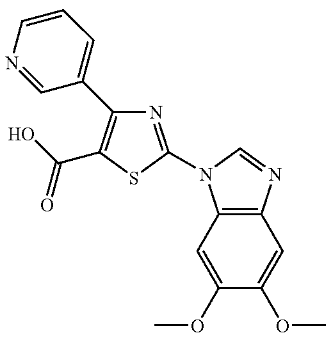 | 2-(5,6-Dimethoxy-benzoimidazol-1-yl)-4-pyridin-3-yl-thiazole-5-carboxylic acid | IC50 = 4.405 |
| Example 34 | 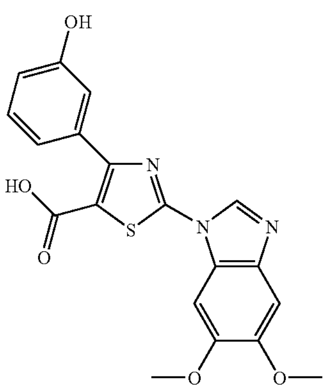 | 2-(5,6-Dimethoxy-benzoimidazol-1-yl)-4-(3-hydroxy-phenyl)-thiazole-5-carboxylic acid | IC50 = 0.211 |
| Example 35 | | 2-(5-Chloro-6-fluoro-benzoimidazol-1-yl)-4-phenyl-thiazole-5-carboxylic acid; compound with 2-(6-chloro-5-fluoro-benzoimidazol-1-yl)-4-phenyl-thiazole-5-carboxylic acid | IC50 = 1.287 |

-continued

| Example # | Structure | Systematic Name | IC50 (μM) |
|---|---|---|---|
| Example 36 | 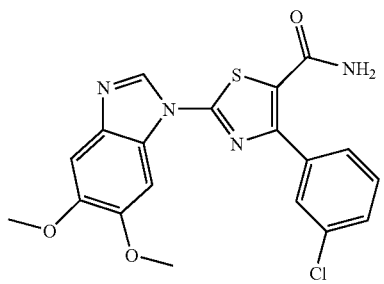 | 4-(3-Chloro-phenyl)-2-(5,6-di-methoxy-benzoimidazol-1-yl)-thiazole-5-carboxylic acid amide | IC50 = 0.431 |
| Example 38 | 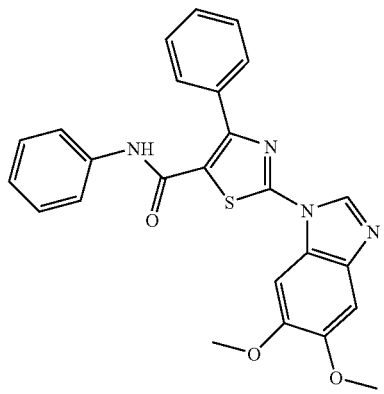 | 2-(5,6-Dimethoxy-benzoimidazol-1-yl)-4-phenyl-thiazole-5-carboxylic acid phenylamide | IC50 = 0.606 |
| Example 39 | 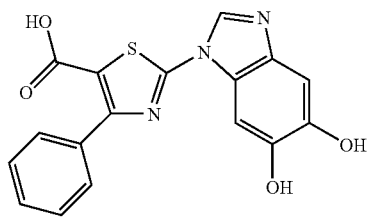 | 2-(5,6-Dihydroxy-benzoimidazol-1-yl)-4-phenyl-thiazole-5-carboxylic acid | IC50 = 2.015 |
| Example 40 | 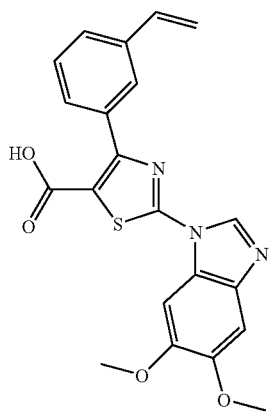 | 2-(5,6-Dimethoxy-benzoimidazol-1-yl)-4-(3-vinyl-phenyl)-thiazole-5-carboxylic acid | IC50 = 0.102 |

| Example # | Structure | Systematic Name | IC50 (μM) |
|---|---|---|---|
| Example 41 | 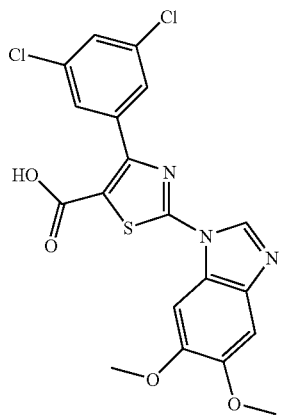 | 4-(3,5-Dichloro-phenyl)-2-(5,6-dimethoxy-benzoimidazol-1-yl)-thiazole-5-carboxylic acid | IC50 = 0.066 |
| Example 42 | 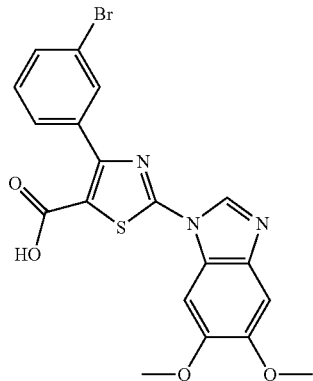 | 4-(3-Bromo-phenyl)-2-(5,6-dimethoxy-benzoimidazol-1-yl)-thiazole-5-carboxylic acid | IC50 = 0.04 |
| Example 43 | 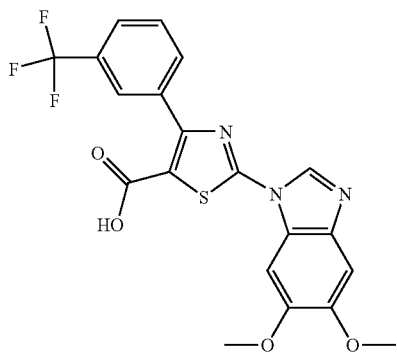 | 2-(5,6-Dimethoxy-benzoimidazol-1-yl)-4-(3-trifluoromethyl-phenyl)-thiazole-5-carboxylic acid | IC50 = 0.157 |

-continued

| Example # | Structure | Systematic Name | IC50 (μM) |
|---|---|---|---|
| Example 45 | 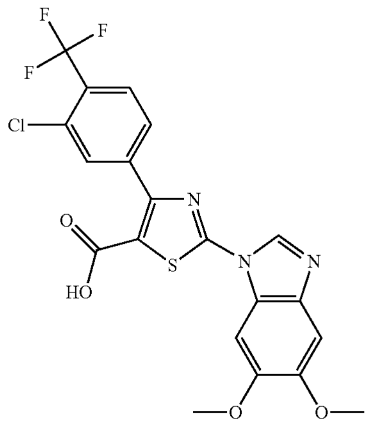 | 4-(3-Chloro-4-trifluoromethyl-phenyl)-2-(5,6-dimethoxy-benzoimidazol-1-yl)-thiazole-5-carboxylic acid | IC50 = 0.354 |
| Example 46 | 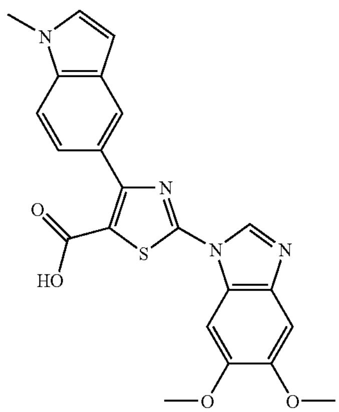 | 2-(5,6-Dimethoxy-benzoimidazol-1-yl)-4-(1-methyl-1H-indol-5-yl)-thiazole-5-carboxylic acid | IC50 = 0.368 |
| Example 47 | 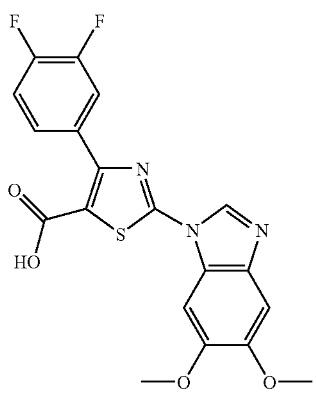 | 4-(3,4-Difluoro-phenyl)-2-(5,6-dimethoxy-benzoimidazol-1-yl)-thiazole-5-carboxylic acid | IC50 = 0.542 |
| Example 48 | 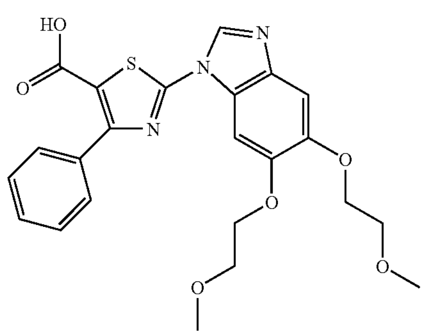 | 2-[5,6-Bis-(2-methoxy-ethoxy)-benzoimidazol-1-yl]-4-phenyl-thiazole-5-carboxylic acid | IC50 = 0.819 |

| Example # | Structure | Systematic Name | IC50 (μM) |
|---|---|---|---|
| Example 49 | 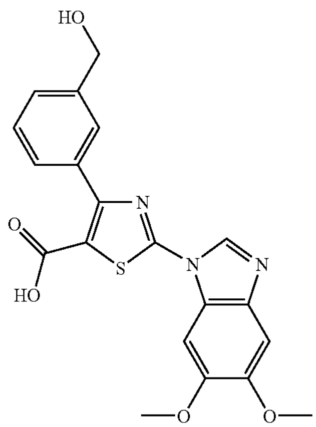 | 2-(5,6-Dimethoxy-benzoimidazol-1-yl)-4-(3-hydroxymethyl-phenyl)-thiazole-5-carboxylic acid | IC50 = 1.08 |
| Example 50 | 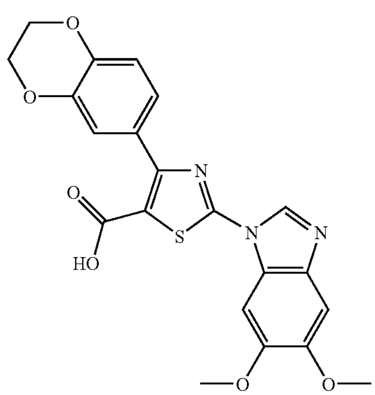 | 4-(2,3-Dihydro-benzo[1,4]dioxin-6-yl)-2-(5,6-dimethoxy-benzoimidazol-1-yl)-thiazole-5-carboxylic acid | IC50 = 2.34 |
| Example 51 | 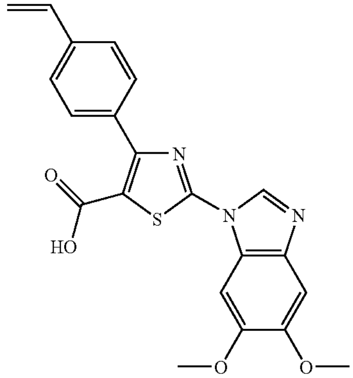 | 2-(5,6-Dimethoxy-benzoimidazol-1-yl)-4-(4-vinyl-phenyl)-thiazole-5-carboxylic acid | IC50 = 2.674 |

-continued

| Example # | Structure | Systematic Name | IC50 (μM) |
|---|---|---|---|
| Example 52 | 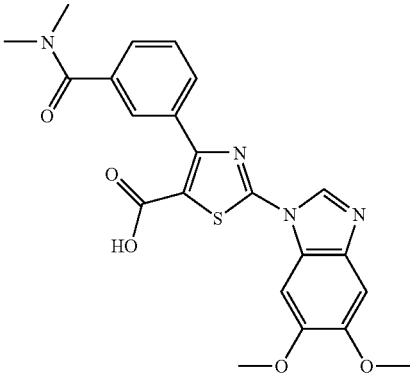 | 2-(5,6-Dimethoxy-benzoimidazol-1-yl)-4-(3-dimethylcarbamoyl-phenyl)-thiazole-5-carboxylic acid | IC50 = 8.87 |
| Example 53 | 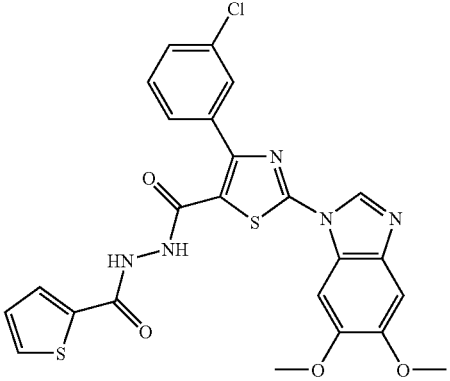 | Thiophene-2-carboxylic acid N'-[4-(3-chloro-phenyl)-2-(5,6-dimethoxy-benzoimidazol-1-yl)-thiazole-5-carbonyl]-hydrazide | IC50 = 0.018 |
| Example 54 | 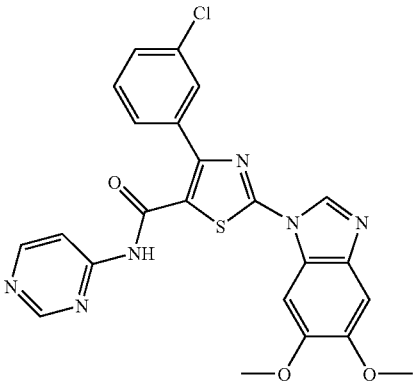 | 4-(3-Chloro-phenyl)-2-(5,6-dimethoxy-benzoimidazol-1-yl)-thiazole-5-carboxylic acid pyrimidin-4-ylamide | IC50 = 0.047 |
| Example 55 | 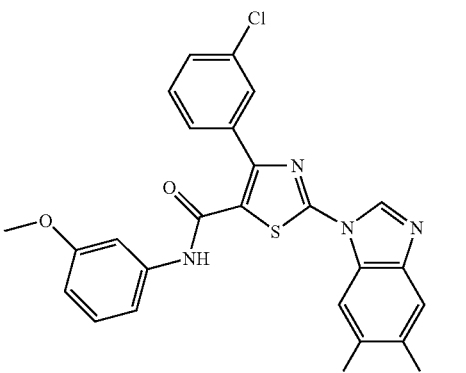 | 4-(3-Chloro-phenyl)-2-(5,6-dimethoxy-benzoimidazol-1-yl)-thiazole-5-carboxylic acid (3-methoxy-phenyl)-amide | IC50 = 0.250 |

-continued

| Example # | Structure | Systematic Name | IC50 (μM) |
|---|---|---|---|
| Example 56 | 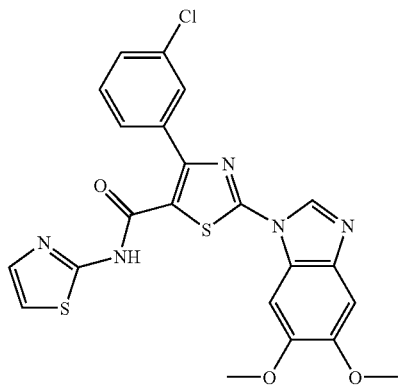 | 4-(3-Chloro-phenyl)-2-(5,6-di-methoxy-benzoimidazol-1-yl)-thiazole-5-carboxylic acid thiazol-2-ylamide | IC50 = 0.252 |
| Example 57 | 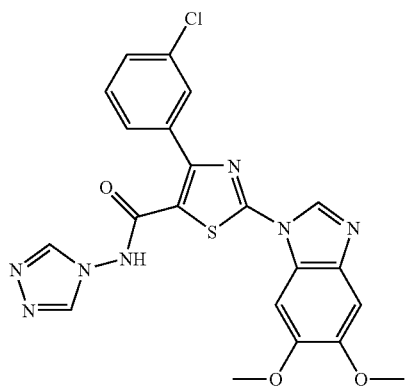 | 4-(3-Chloro-phenyl)-2-(5,6-di-methoxy-benzoimidazol-1-yl)-thiazole-5-carboxylic acid [1,2,4]triazol-4-ylamide | IC50 = 0.344 |
| Example 58 | 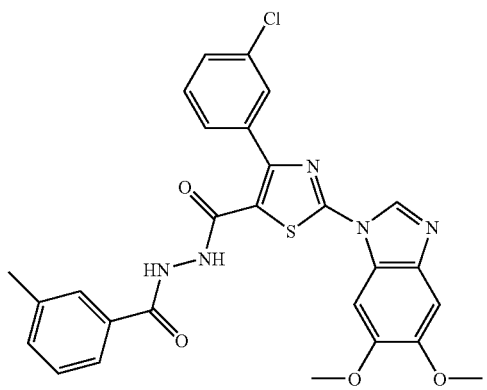 | 3-Methyl-benzoic acid N'-[4-(3-chloro-phenyl)-2-(5,6-di-methoxy-benzoimidazol-1-yl)-thiazole-5-carbonyl]-hydrazide | IC50 = 0.586 |
| Example 59 | 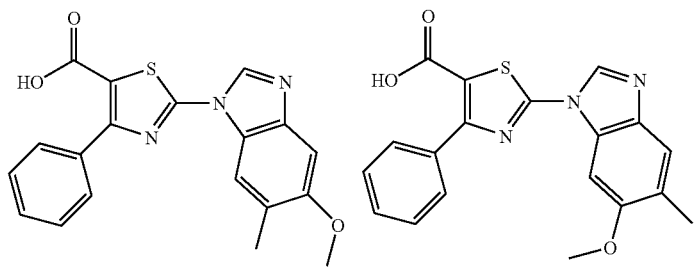 | 2-(5-Methoxy-6-methyl-benzoimidazol-1-yl)-4-phenyl-thiazole-5-carboxylic acid; compound with 2-(6-methoxy-5-methyl-benzoimidazol-1-yl)-4-phenyl-thiazole-5-carboxylic acid | IC50 = 0.826 |

-continued

| Example # | Structure | Systematic Name | IC50 (μM) |
|---|---|---|---|
| Example 60 | 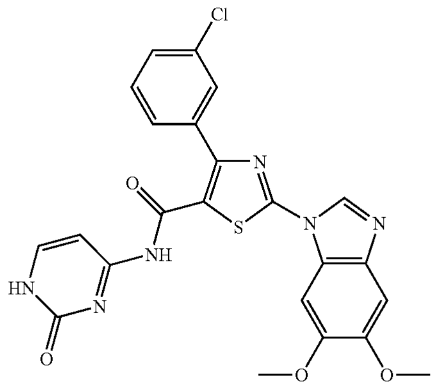 | 4-(3-Chloro-phenyl)-2-(5,6-dimethoxy-benzoimidazol-1-yl)-thiazole-5-carboxylic acid (2-oxo-1,2-dihydro-pyrimidin-4-yl)-amide | IC50 = 4.430 |
| Example 61 | 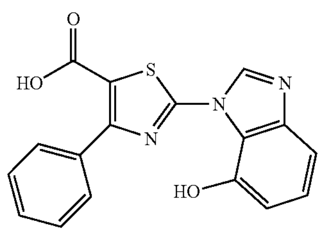 | 2-(7-Hydroxy-benzoimidazol-1-yl)-4-phenyl-thiazole-5-carboxylic acid | IC50 = 4.681 |
| Example 62 | 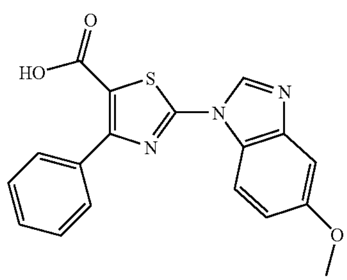 | 2-(5-Methoxy-benzoimidazol-1-yl)-4-phenyl-thiazole-5-carboxylic acid | IC50 = 0.261 |
| Example 63 | 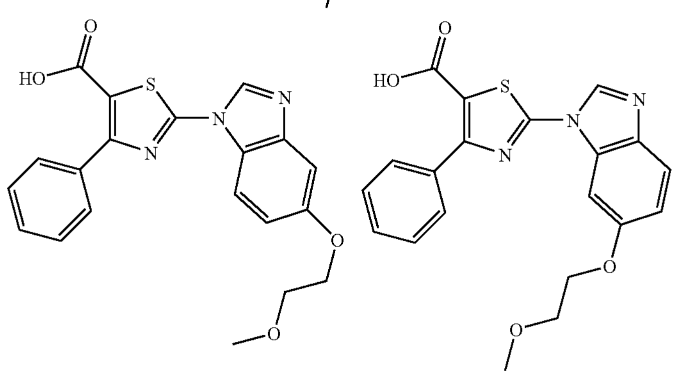 | 2-[5-(2-Methoxy-ethoxy)-benzoimidazol-1-yl]-4-phenyl-thiazole-5-carboxylic acid; compound with 2-[6-(2-methoxy-ethoxy)-benzoimidazol-1-yl]-4-phenyl-thiazole-5-carboxylic acid | IC50 = 0.526 |
| Example 64 | 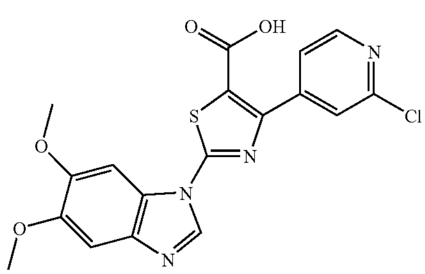 | 4-(2-Chloro-pyridin-4-yl)-2-(5,6-dimethoxy-benzoimidazol-1-yl)-thiazole-5-carboxylic acid | IC50 = 0.075 |

| Example # | Structure | Systematic Name | IC50 (μM) |
|---|---|---|---|
| Example 65 | | 2-(5-Hydroxy-benzoimidazol-1-yl)-4-phenyl-thiazole-5-carboxylic acid; compound with 2-(6-hydroxy-benzoimidazol-1-yl)-4-phenyl-thiazole-5-carboxylic acid | IC50 = 0.388 |

Chemical Synthesis Protocols

The following examples illustrate preferred methods for synthesizing the compounds and formulations of the present inventions. In addition, there may exist other ways to synthesize these molecules.

Reagents were purchased from Aldrich, Sigma, Maybridge, Advanced ChemTech, and Lancaster or other suppliers as indicated below and used without further purification.

The purity of the exemplified compounds was determined by analytical HPLC. Where the purity of the compound did not exceed 85 percent as judged by UV absorption at 214 nm, the compound was purified by preparative HPLC. The conditions for analytical and preparative HPLC are given below.

Analytical HPLC

Analytical HPLC was carried out with a Waters 600 LC pump and Supelco Discovery C18 column (5 μm, 50 mm×4.6 mm). Mobile phases A (0.1% formic acid in water) and B (0.1% formic acid in acetonitrile) were used in a gradient of 5% B rising to 98% B after 5 mins, held for 4 min at a flow rate of 2 mL/min. Photo-diode array (PDA) detection was by a Waters 996 Photodiode Array Detector, range 210-400 nm UV and ELS detection with a Polymer Laboratories PL-ELS 1000 (Nitrogen flow rate 1.3 L/min. Nebulizer temp. 80° C., Evap. temp. 110° C.). The Mass spectrometer was a Micromass ZQ operating in electrospray ionization mode.

Preparative HPLC

Compounds were purified by HPLC Method A unless otherwise indicated.

Method A:

Samples that required purification were purified with a Waters mass-directed purification system utilizing a Waters 600 LC pump, Waters Xterra C18 column (5 μm, 19 mm×50 mm) and Micromass ZQ mass spectrometer, operating in positive ion electrospray ionization mode. Mobile phases A (0.1% formic acid in water) and B (0.1% formic acid in acetonitrile) were used in a gradient; 5% B to 30% B over 7 mins, held for 1 min, at a flow rate of 20 mL/min. Gradients in which formic acid was substituted with trifluoroacetic acid are also possible; gradients without use of acid modifiers are also possible.

Method B:

Purification was also carried out using a Gilson 215 liquid handler, Gilson 819 inject module, Gilson 322 pumps and Gilson UV/VIS-155 detector system with a YMC-Pack ODS-A AA-12S11-L530WT SH-36605-10P 75×30 I.D. S-10 μm, 12 mm column. The mobile phase used was acetonitrile and pure water.

Preparation of Intermediates

Intermediates Prepared for Example 1, 2 and Subsequent Examples

2-Chloro-4-phenylthiazole-5-carboxylic acid ethyl ester

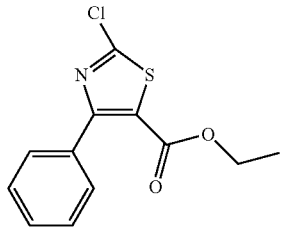

2-Chloro-4-phenylthiazole-5-carboxylic acid ethyl ester (12,71 g, yield 78%) was prepared from 2-amino-4-phenylthiazole-5-carboxylic acid ethyl ester (15.21 g, 61.25 mmol.) (Lancaster) by reaction with 1.1 equivalents of $CuCl_2$ and 1.1. eq. of tert-butyl nitrite in 80 mL of acetonitrile stirred at reflux for 20 min. At this time, the acetonitrile was removed; the residue was diluted with ~100 mL of ethyl acetate and washed with 30 mL of 3N aqueous hydrochloric acid followed by a water wash. The ethyl acetate layer was dried over $MgSO_4$, filtered and then concentrated in vacuo. The crude product was purified on an ISCO silica gel flash column eluting with 5 to 30% EtOAc in hexane to yield the product in 78% yield. $^1$H-NMR (300 MHz, $CDCl_3$) 7.77(m, 2H); 7.41(m, 3H); 4.26(q, J=Hz, 2H); 1.23(t, J=Hz, 3H). MS M/z 268(M+1)

Intermediates Prepared for Example 1, 2 and subsequent examples 2-(5,6-Dimethoxybenzoimidazol-1-yl)-4-phenylthiazole-5-carboxylic acid ethyl ester

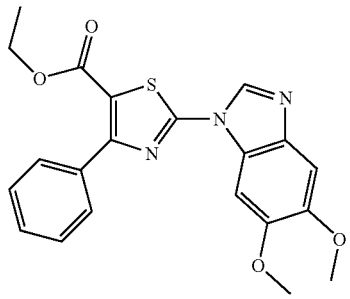

5,6-Dimethoxybenzimidazole (470 mg, 2.64 mmol) was added to a suspension of NaH (60% in mineral oil, 112 mg, 2.8 mmol) in NMP (5 ml) at <5° C. The mixture was stirred for 20 min, then a solution of 2-chloro-4-phenylthiazole-5-carboxylic acid ethyl ester (589 mg, 2.2 mmol) in NMP (1.5 ml) was added over 2-3 min. The mixture was stirred 2.5 hrs at RT. Water (15 ml) was added and stirred for 20 min. Solid was collected by filtration to provide the product 2-(5,6-dimethoxy-benzoimidazol-1-yl)-4-phenylthiazole-5-carboxylic acid ethyl ester (753 mg. Yield 84%). $^1$H-NMR (300 MHz, CDCl3) 8.44(s, 1H); 7.87-7.90(m, 2H); 7.72(2, 1H); 7.44-7.49(m, 3H); 7.30(s, 1H); 4.32(q, J=Hz, 2H); 3.98(s, 3H); 3.97(s, 3H); 1.33(t, J=Hz, 3H). MS M/z 410(M+1).

Intermediate Prepared for Example 2

2-(Benzoimidazol-1-yl)-4-phenylthiazole-5-carboxylic acid ethyl ester

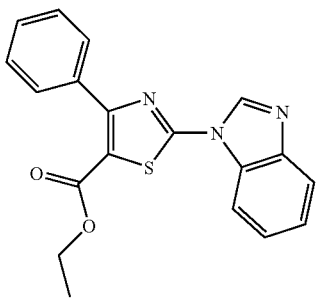

A mixture of 2-chloro-4-phenylthiazole-5-carboxylic acid ethyl ester (134 mg, 0.5 mmol), benzimidazole (Aldrich) (73.8 mg, 0.625 mmol) and LiN(TMS)$_2$ (1N tetrahydrofuran solution, 0.63 ml) in tetrahydrofuran (2 ml) was heated in a micro-wave oven at 120° C. for 30 min. Water (3 ml) was added and the mixture was filtered, washed with water and ethyl acetate, dried in air flow to give 2-(benzoimidazol-1-yl)-4-phenylthiazole-5-carboxylic acid ethyl ester (108 mg, 61%). The aqueous solution was concentrated to remove tetrahydrofuran and then extracted with ethyl acetate to recover an additional amount of the product (100 mg, 75% pure). 1H-NMR (CDCl3) 8.84 (s, 1H); 8.16 (d, 1H); 7.81-7.90 (m, 3H); 7.39-7.58 (m, 5H); 4.37 (q, 2H); 1.27 (t, 3H). MS M/z 350 (M+1).

General methods for the preparation of substituted benzimidazoles useful for synthesizing compounds of the invention may be found in J. Med. Chem. 2000, 43, 4084-4097; Synthetic Comm. 1998, 28, 4137-4142; J. Med. Chem. 1987, 30, 2216-2221; and J. Org. Chem. 1985, 50, 2205-2210.

General Procedure for Benzimidazoles:

Diaminobenzenes were either commercially available or were prepared from o-dinitrobenzenes or o-nitro-anilines by catalytic hydrogenation with 5% palladium on carbon in methanol or ethyl acetate under atmospheric pressure of hydrogen gas at room temperature. The reaction was monitored for completion which usually requires several hours to overnight reaction. Upon completion, the reaction mixture is filtered and washed through Celite. The filtrate is concentrated in vacuo to give the o-diaminobenzene. The ortho-diaminobenzene was then stirred at reflux in formic acid for 1-2 hrs. After removal of formic acid in vacuo, the residue was diluted with water and neutralized with 15% NaOH to approximately pH=8. The solid was filtered and washed with water and dried in air.

5,6-Dimethoxy-1H-benzoimidazole

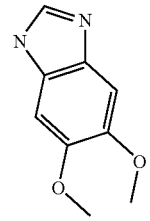

5,6-Dimethoxy-1H-benzoimidazole (2.57 g, 14.9 mmol, yield 60%) was prepared from 4,5-dimethoxy-1,2-dinitrobenzene (5.68 g, 24.9 mmol) according to the general procedure for benzimidazoles above. 1H-NMR (CDCl3) 10.41 (s, 1H); 7.95 (s, 1H); 7.06 (s, 2H); 3.90 (s, 6H). MS M/z 179 (M+1).

5,6-Dichloro-1H-benzoimidazole

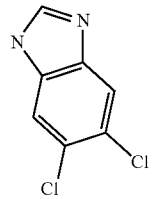

5,6-Dichloro-1H-benzoimidazole (6.06 g, 0.324 mol, yield 100%) from 1,2-diamino-4,5-dichlorobenzene (5.73 g, 0.324 mol) according to the general procedure for benzimidazoles above. 1H-NMR (DMSO-D6) 8.30 (s, 1H); 7.83 (s, 2H). MS M/z 188. (M+1).

5-Methoxy-1H-benzoimidazole

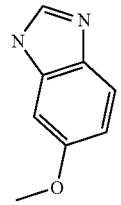

5-Methoxy-1H-benzoimidazole (7.5 g, 50.4 mmol, yield 95%) was prepared from 1,2-diamino-4-methoxybenzene dihydrochloride (11.2 g, 53,3 mmol) according to the general procedure for benzimidazoles above. 1H-NMR (DMSO-D6) 8.14 (s, 1H); 7.46 (d, 1H); 7.08 (s, 1H); 6.82 (d, 1H); 3.79 (s, 3H). MS M/z 149. (M+1).

3H-Imidazo[4,5-f]quinoline

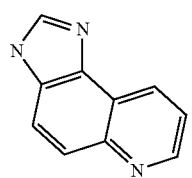

3H-Imidazo[4,5-f]quinoline was prepared from quinoline-5,6-diamine according to the general procedure for benzimidazoles above. 1H-NMR (CDCl3) 8.87-9.30 (m, 2H); 8.19 (s, 1H); 7.94 (s, 2H); 7.50 (q, 1H). MS M/z 170 (M+1).

4-Hydroxy-1H-benzoimidazole

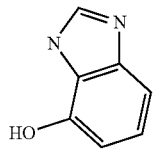

4-Hydroxy-1H-benzoimidazole was prepared from 2,3-dinitrophenol according to the general procedure for benzimidazoles above. MS M/z 135 (M+1).

6-Chloro-5-methyl-1H-benzoimidazole

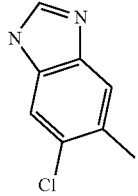

6-Chloro-5-methyl-1H-benzoimidazole was prepared from 5-chloro-4-methyl-2-nitroaniline according to the general procedure for benzimidazoles above. 1H-NMR(CDCl3) 8.23 (s, 1H); 7.64 (s, 1H0; 7.56 (s, 1H); 4.40 (s, 3H). MS M/z 167 (M+1).

1H-Benzoimidazole-4-carboxylic acid methyl ester

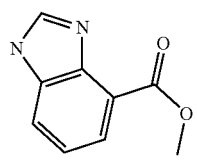

1H-Benzoimidazole-4-carboxylic acid methyl ester was prepared from 2-amino-3-nitrobenzoic acid methyl ester according to the general procedure for benzimidazoles above. M/z 177 (M+1).

1,8-Dihydro-5,7-dioxa-1,3-diaza-cyclopenta[b]naphthalene

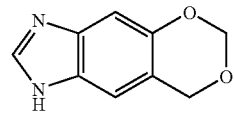

1,8-Dihydro-5,7-dioxa-1,3-diaza-cyclopenta[b]naphthalene was prepared by nitration of the commercially available 4,5-dihydro-1,3-benzodioxine-6-amine followed by treatment with reaction conditions described in the general procedure for benzimidazoles above.

General procedure used for the formation of amides from 2-benzoimidazol-1-yl-4-phenyl-thiazole-5-carboxylic acids esters 2-(Benzoimidazol-1-yl)-4-phenylthiazole-5-carboxylic acid ethyl esters in alcohol or water solution of an amine was heated in a sealed tube at 85-130° C. for 2-5 hrs. The product was precipitated by adding water to the mixture and dried in air, or purified by preparative HPLC if the reaction contains numerous side products.

Preparation of Intermediates for Example 26 and Related Analogs
2,4-Dibromo-thiazole-5-carbaldehyde

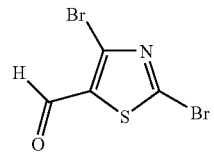

To a mixture of 2,4-thiazolidinedione (technical grade, 90%; 19.1 g, 147 mmol) and POBr$_3$ (210 g, 734 mmol) at 0° C. was added dropwise dimethylformamide (12.5 ml, 161.5 mmol). The resulting solid was heated to 105° C. for 8 hrs. The dark oil solidified upon cooling. A large amount of ice was added to quench the excess POBr$_3$. The precipitate was filtered and the filtrate was extracted with 3×200 ml CH$_2$Cl$_2$. The combined organics were washed with 50 ml saturated NaHCO$_3$ and 100 ml brine, dried with MgSO$_4$ and concentrated in vacuo to afford a brown solid. The crude was purified by flash chromatography with 0 to 5% ethyl acetate/Hexanes to afford 2,4-dibromo-thiazole-5-carbaldehyde (14.8 g, 37%) as a yellow solid. $^1$H NMR (300 MHz, CDCl$_3$) 9.89 (s, 1H).

2,4-Dibromo-thiazole-5-carboxylic acid

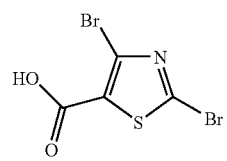

Solid potassium permanganate (2.19 g, 13.85 mmol) was added portionwise to a hot suspension of 2,4-dibromo-thiazole-5-carbaldehyde (2.5 g, 9.23 mmol) in water (20 ml). The progress of the reaction was monitored by HPLC. More potassium permanganate was added until all of the aldehyde was consumed. The dark suspension was filtered while hot. The filtrate was cooled and acidified with conc. hydrochloric acid to pH=2 to 3. The resulting precipitate was filtered off to afford a white solid as the desired product. The filtrate was lyophilized and methanol was added to dissolve the remaining acid product. The suspension was filtered and the filtrate was concentrated in vacuo. Two crops were combined to give 2,4-dibromo-thiazole-5-carboxylic acid 1.8 g (68%). $^1$H NMR (300 MHz, DMSO-d$_6$) δ 11.87 (s, 1H).

2,4-Dibromo-thiazole-5-carboxylic acid methyl ester

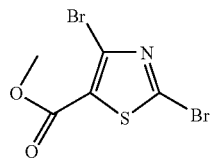

A solution of 2,4-dibromo-thiazole-5-carboxylic acid (1.7 g, 5.92 mmol) in methanol (20 ml) was treated with N-(3-dimethylaminopropyl)-N'-ethylcarbodiimide (920 mg, 5.92 mmol). The mixture was stirred at ambient temperature overnight. The solvent was evaporated and water (30 ml) was added. The mixture was then extracted with 3×30 ml of EtOAc. The combined organics were washed with brine, dried with MgSO$_4$ and concentrated in vacuo. The crude was purified by flash chromatography (0 to 5% EtOAc/Hexanes) to afford 2,4-Dibromo-thiazole-5-carboxylic acid methyl ester (1.4 g, 78%) as a white solid. $^1$H NMR (300 MHz, CDCl$_3$) δ 3.91 (s, 3H).

4-Bromo-2-(5,6-dimethoxy-benzoimidazol-1-yl)-thiazole-5-carboxylic acid methyl ester

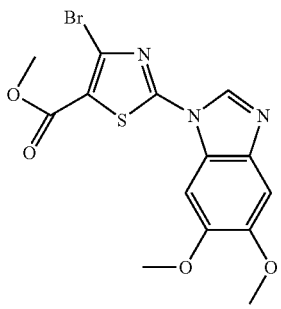

To a solution of 5,6-Dimethoxy-1H-benzimidazole (1.0 g, 5.65 mmol) in 1-methyl-2-pyrrolidinone (10 ml) at 0° C. was added NaH (60% dispersion; 339 mg, 8.475 mmol). After gas evolution had stopped, 2,4-Dibromo-thiazole-5-carboxylic acid methyl ester (1.7 g, 5.65 mmol) was added. The resulting solution was stirred at ambient temperature for 1 hr. 50 ml water was added. The suspension was stirred for 10 min and filtered to afford 4-bromo-2-(5,6-dimethoxy-benzoimidazol-1-yl)-thiazole-5-carboxylic acid methyl ester (1.6 g, 73%) as a light brown solid. $^1$H NMR (300 MHz, CDCl$_3$) δ 3.96 (s, 3H), 3.98 (s, 3H), 4.03 (s, 3H), 7.32 (s, 1H), 7.58 (s, 1H), 8.39 (s, 1H).

EXAMPLES

Example 1

2-(5,6-Dimethoxybenzoimidazol-1-yl)-4-phenylthiazole-5-carboxylic acid

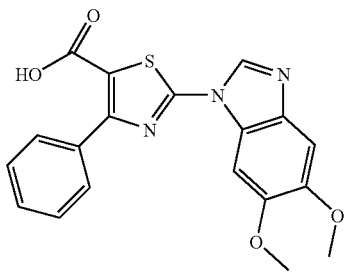

2-(5,6-Dimethoxybenzoimidazol-1-yl)-4-phenylthiazole-5-carboxylic acid ethyl ester (180 mg, 0.44 mmol) was suspended in THF (4 ml), NaOH (15%, 1.5 ml) and water (2 ml) and the mixture was stirred at 40-50° C. for 3 hrs. After THF was removed, the residue was extracted with ethyl acetate (2×2 mL). The aqueous was then neutralized with 3N HCl to pH=3. The solid was collected by filtration and was washed with water, dried in airflow to give 2-(5,6-Dimethoxybenzoimidazol-1-yl)-4-phenylthiazole-5-carboxylic acid (147 mg, 0.38 mmol, 88%). 1H-NMR (DMSO-D6) 8.74 (s, 1H); 7.80 (s, 1H); 7.57-7.63 (m, 2H); 7.40-7.56 (m, 3H); 7.38 (s, 1H); 3.83 (d, 6H). MS M/z 382 (M+1).

Example 2

2-(Benzoimidazol-1-yl)-4-phenylthiazole-5-carboxylic acid

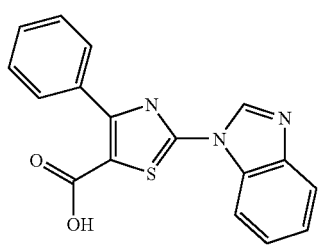

2-(Benzoimidazol-1-yl)-4-pheny-lthiazole-5-carboxylic acid ethyl ester was hydrolyzed in a similar manner as Example 1 to produce 2-(benzoimidazol-1-yl)-4-phenylthiazole-5-carboxylic acid. MS M/z 322 (M+1).

Example 3

2-Benzoimidazol-1-yl-4-phenyl-thiazole-5-carboxylic acid amide

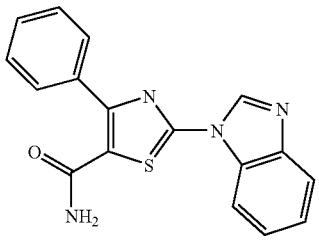

2-Benzoimidazol-1-yl-4-phenyl-thiazole-5-carboxylic acid amide was prepared from 2-Benzoimidazol-1-yl-4-phenyl-thiazole-5-carboxylic acid ethyl ester (75 mg, 0.21 mmol) and ammonium hydroxide as described above in the general amide formation procedure. Preparative HPLC with trifluoroacetic acid, 9.1 mg, 13% yield. MS M/z 321 (M+1).

Example 4

2-(5-Methylbenzoimidazol-1-yl)-4-phenylthiazole-5-carboxylic acid and 2-(6-Methylbenzoimidazol-1-yl)-4-phenylthiazole-5-carboxylic acid

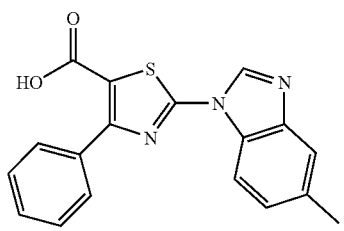

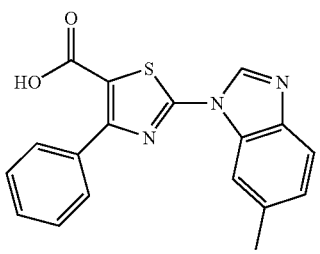

2-(5-Methylbenzoimidazol-1-yl)-4-phenylthiazole-5-carboxylic acid and 2-(6-Methylbenzoimidazol-1-yl)-4-phenylthiazole-5-carboxylic acid was prepared in a similar manner as that for Example 1 starting with the reaction of 5-methylbenzoimidazole (Aldrich) and 2-Chloro-4-phenylthiazole-5-carboxylic acid ethyl ester. 1H-NMR (DMSO-D6) 8.90 (d, 1H); 8.18-8.24 (m, 2H); 8.12 (d, ½H); 8.00 (s, ½H); 7.69 (d, ½H); 7.60 (s, ½H); 7.31-7.43 (m, 3H); 7.18-7.26 (m, 1H); 2.46 (d, 3H). MS M/z 336 (M+1).

Example 5

2-(5,6-Dimethylbenzoimidazol-1-yl)-4-phenylthiazole-5-carboxylic acid

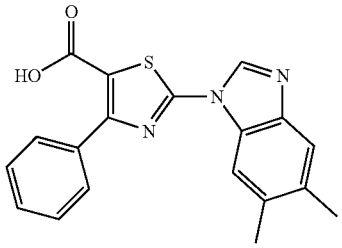

2-(5,6-Dimethylbenzoimidazol-1-yl)-4-phenylthiazole-5-carboxylic acid was prepared in a similar manner as that for Example 1 starting with the reaction of 5,6-dimethylbenzoimidazole and 2-Chloro-4-phenylthiazole-5-carboxylic acid ethyl ester. 1H-NMR(DMSO-D6) 8.82 (s, 1H); 7.98 (s, 1H); 7.82-7.92 (m, 2H); 7.58 (s, 1H); 7.42-7.52 (m, 3H); 2.39 (s, 3H); 2.38 (s, 3H). MS M/z 350 (M+1).

Example 6

2-(5,6-Dimethoxy-benzoimidazol-1-yl)-4-phenyl-thiazole-5-carboxylic acid amide

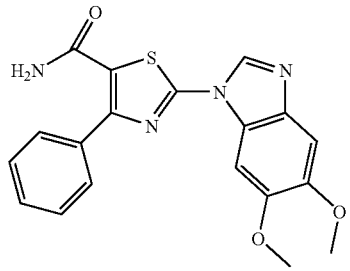

2-(5,6-Dimethoxy-benzoimidazol-1-yl)-4-phenyl-thiazole-5-carboxylic acid amide was prepared from 2-(5,6-Dimethoxy-benzoimidazol-1-yl)-4-phenyl-thiazole-5-carboxylic acid ethyl ester (80 mg, 0.20 mmol) and ammonia in ethanol (29 molar) as described above in the general amide formation procedure. The product was isolated by preparative HPCL: 7.7 mg, 36% yield. 1H-NMR (DMSO-D6) 8.78 (s, 1H); 7.80-7.90 (m, 4H); 7.789s, 1H); 7.40-7.55 (m, 3H); 7.38 (s, 1H); 3.84 (s, 3H); 3.83 (s, 3H). MS M/z 381 (M+1).

Example 7

2-(4-Hydroxy-benzoimidazol-1-yl)-4-phenyl-thiazole-5-carboxylic acid and 2-(7-hydroxy-benzoimidazol-1-yl)-4-phenyl-thiazole-5-carboxylic acid

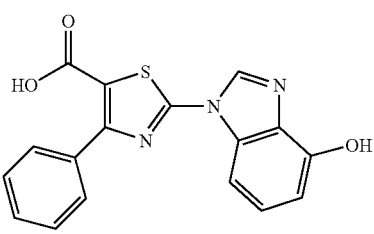

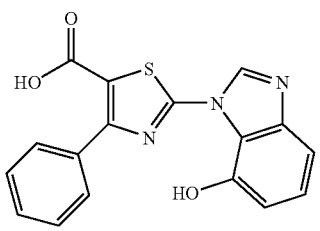

2-(4-Hydroxy-benzoimidazol-1-yl)-4-phenyl-thiazole-5-carboxylic acid and 2-(7-hydroxy-benzoimidazol-1-yl)-4-phenyl-thiazole-5-carboxylic acid were prepared in a similar manner as that for Example 1 starting with the reaction of 4-Hydroxy-benzoimidazole and 2-Chloro-4-phenylthiazole-5-carboxylic acid ethyl ester. 1H-NMR (DMSO-D6) 8.84 (s, 1H); 7.86-7.92 (m, 2H); 7.66 (d, 1H); 7.42-7.52 (m, 3H); 7.27 (t, 1H); 6.80 (d, 1H). MS M/z 338 (M+1).

Example 8

1-(5-Carboxy-4-phenyl-thiazol-2-yl)-1H-benzoimidazole-4-carboxylic acid and 3-(5-carboxy-4-phenyl-thiazol-2-yl)-3H-benzoimidazole-4-carboxylic acid

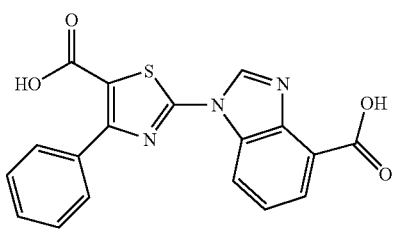

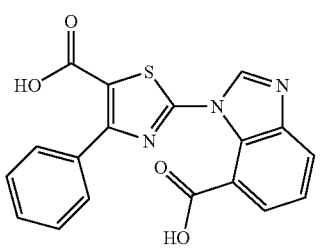

1-(5-Carboxy-4-phenyl-thiazol-2-yl)-1H-benzoimidazole-4-carboxylic acid and 3-(5-carboxy-4-phenyl-thiazol-2-yl)-3H-benzoimidazole-4-carboxylic acid were prepared in a similar manner as that for Example 1 starting with the reaction of 5-Carboxy-4-phenyl-thiazol-2-yl)-1H-benzoimidazole and 2-Chloro-4-phenylthiazole-5-carboxylic acid ethyl ester. 1H-NMR (DMSO-D6) 9.20 (d, 1H); 8.84 (s, ½H); 8.32 (dd, 1½H); 8.60 (dd, 1H); 7.82-7.92 (m, 2H); 7.48-7.55 (m, 3H). MS M/z 366 (M+1).

Example 9

2-(8H-5,7-Dioxa-1,3-diaza-cyclopenta[b]naphthalen-3-yl)-4-phenyl-thiazole-5-carboxylic acid and 2-(8H-5,7-Dioxa-1,3-diaza-cyclopenta[b]naphthalen-1-yl)-4-phenyl-thiazole-5-carboxylic acid

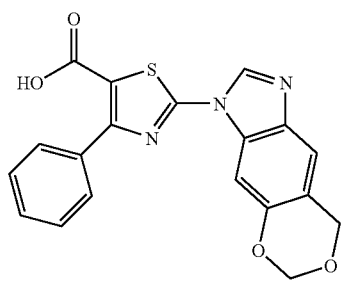

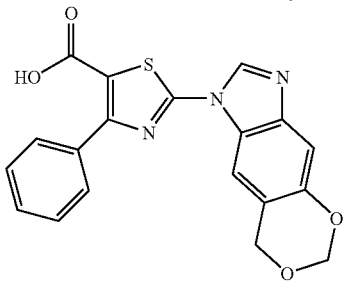

2-(8H-5,7-Dioxa-1,3-diaza-cyclopenta[b]naphthalen-3-yl)-4-phenyl-thiazole-5-carboxylic acid and 2-(8H-5,7-Dioxa-1,3-diaza-cyclopenta[b]naphthalen-1-yl)-4-phenyl-thiazole-5-carboxylic acid were prepared in a similar manner as that for Example 1 starting with the reaction of 8H-5,7-Dioxa-1,3-diaza-cyclopenta[b]naphthalene and 2-Chloro-4-phenylthiazole-5-carboxylic acid ethyl ester. MS M/z 380 (M+1).

Example 10

2-(5,6-Dimethoxy-benzoimidazol-1-yl)-4-phenyl-thiazole-5-carboxylic acid dimethylamide

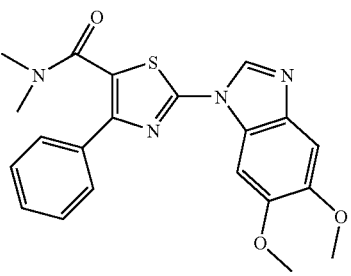

2-(5,6-Dimethoxy-benzoimidazol-1-yl)-4-phenyl-thiazole-5-carboxylic acid dimethylamide was prepared from 2-(5,6-Dimethoxy-benzoimidazol-1-yl)-4-phenyl-thiazole-5-carboxylic acid ethyl ester (48.8 mg, 0.12 mmol) and dimethyl amine in methanol (2 molar) as described above in the general amide formation procedure. Product was isolated by preparative HPLC:15 mg, 30%. 1H NMR (400 MHz, DMSO-$d_6$) δ ppm 8.81 (s, 1 H); 7.84 (s, 1 H); 7.73-7.79 (m, 2H); 7.44-7.59 (m, 3 H); 7.40 (s, 1 H); 3.91 (s, 3 H, NCH$_3$), 3.86 (s, 3 H); 3.01 (s, 3 H); 2.74 (s, 3 H). MS M/z 409 (M+1).

Example 11

2-(5,6-Dimethoxy-benzoimidazol-1-yl)-4-phenyl-thiazole-5-carboxylic acid ethylamide

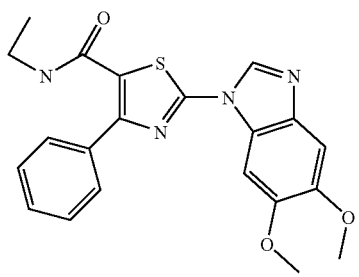

2-(5,6-Dimethoxy-benzoimidazol-1-yl)-4-phenyl-thiazole-5-carboxylic acid ethylamide was prepared from 2-(5,6-Dimethoxy-benzoimidazol-1-yl)-4-phenyl-thiazole-5-carboxylic acid ethyl ester (30 mg, 0.07 mmol) and ethylamine in methanol (2 molar) as described above in the general amide formation procedure. Product was isolated by preparative HPLC: 16 mg, 56%. 1H NMR (400 MHz, DMSO-$d_6$) δ ppm 8.81 (s, 1H); 8.53 (t, 1H); 7.88-7.69 (m, 3H); 7.55-7.44 (m, 3H); 7.40 (s, 1H); 3.88 (s, 3H); 3.85 (s, 3H); 3.25 (q, 2H); 1.08 (t, 3H). MS M/z 409 (M+1).

Example 12

2-Chloro-4-phenyl-thiazole-5-carbonitrile

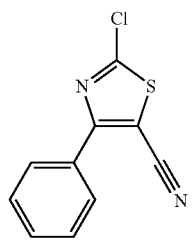

A mixture of 2-Chloro-4-phenyl-thiazole-5-carboxylic acid ethyl ester (1 g, 3.74 mmol) in tetrahydrofuran (10 ml) and NaOH (15%, 4.8 ml) was stirred at room temperature for 2 hr. After removal of tetrahydrofuran, the aqueous was neutralized with aqueous hydrochloric acid (3 N) to ~pH=3. The solid was filtered and washed with water, dried in air to give 2-chloro-4-phenyl-thiazole-5-carboxylic acid (0.83 g). The acid was then dissolved in acetonitrile, and EDC (0.62 g, 4 mmol) was added. The mixture was stirred under an ammonia balloon for 2 hrs. Acetonitrile was removed, the residue was diluted with ethyl acetate and washed with water. Ethyl acetate solution was dried over MgSO4. After removal of MgSO4 and solvent, the residue was diluted with tetrahydrofuran (10 ml), followed by adding triethyl amine (0.5 ml). The mixture was cooled in ice, and trifluoroacetic anhydride (0.85 ml) was added dropwise. After the addition, the reaction mixture was stirred overnight at RT. The mixture was then diluted with ethyl acetate and washed with sat. sodium bicarbonate, dried over MgSO4. After removal of the magnesium sulfate and solvent, the residue was purified on Isco (0-20% gradient ethyl acetate in hexane) to give product (287.9 mg, yield 35% overall). 1H-NMR (CDCl3) 8.07-8.13 (m, 2H); 7.47-7.53 (m, 3H); 4.11 (q, 1H); 1.22 (t, 3H). MS M/z 221 (M+1)

2-(5,6-Dimethoxy-benzoimidazol-1-yl)-4-phenyl-thiazole-5-carbonitrile

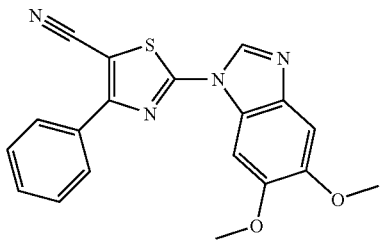

2-(5,6-Dimethoxy-benzoimidazol-1-yl)-4-phenyl-thiazole-5-carbonitrile (48.8 mg, yield 47%) was prepared from 5,6-dimethoxybenzimidazole (76 mg, 0.43 mmol) and 2-chloro-4-phenyl-thiazole-5-carbonitrile as described in Example 1 (63 mg, 0.28 mmol). MS M/z 363 (M+1)

5,6-Dimethoxy-1-[4-phenyl-5-(1H-tetrazol-5-yl)-thiazol-2-yl]-1H-benzoimidazole

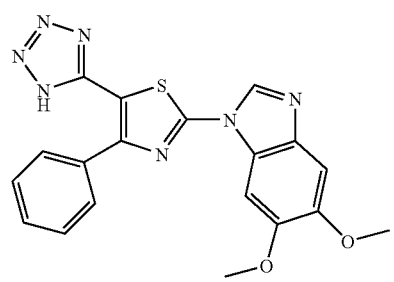

A mixture of 2-(5,6-Dimethoxy-benzoimidazol-1-yl)-4-phenyl-thiazole-5-carbonitrile (261 mg, 0.72 mmol), sodium azide (220 mg) and ammonium chloride (250 mg) in N-methylpyrrolidone (2.5 ml) was stirred at 110° C. for 1 hr. Water was added and the mixture was extracted with methylene chloride. After removal of solvent, the residue was purified by HPLC to yield the product (138.1 mg, yield 47%). 1H-NMR (DMSO-D6) 8.78 (s, 1H); 8.21-8.29 (m, 2H); 7.86 (s, 1H); 7.36-7.50 (m, 3H); 3.90 (s, 3H); 3.88 (s, 3H). MS M/z 406 (M+1).

Example 13

2-(5,6-Dimethoxy-benzoimidazol-1-yl)-4-phenyl-thiazole-5-carboxylic acid cyclopropylamide

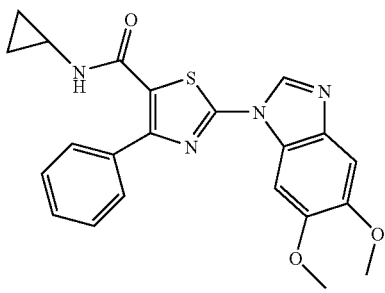

2-(5,6-Dimethoxy-benzoimidazol-1-yl)-4-phenyl-thiazole-5-carboxylic acid cyclopropylamide was prepared from 2-(5,6-Dimethoxy-benzoimidazol-1-yl)-4-phenyl-thiazole-5-carboxylic acid ethyl ester (24 mg, 0.06 mmol) and cyclopropylamine in methanol (4 molar) as described above in the general amide formation procedure. Product was isolated by preparative HPLC: 10 mg, 40%. 1H-NMR (DMSO-D6) 8.8 (s, 1H); 8.54 (t, 1H); 7.80-7.87 (m, 2H); 7.41-7.55 (m, 3H); 7.38 (s, 1H); 3.90 (s, 3H); 3.86 (s, 3H); 3.25 (q, 2H); 1.08 (t, 3H). MS M/z 421 (M+1).

Example 14

2-(5-Chlorobenzoimidazol-1-yl)-4-phenylthiazole-5-carboxylic acid and 2-(6-chlorobenzoimidazol-1-yl)-4-phenylthiazole-5-carboxylic acid

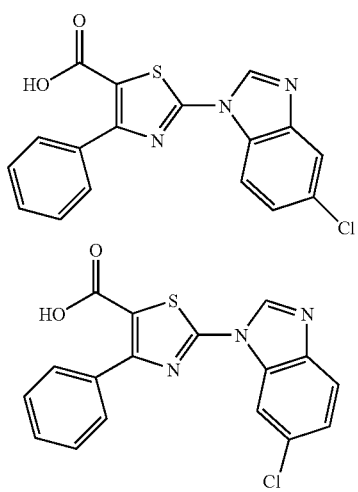

2-(5-Chlorobenzoimidazol-1-yl)-4-phenylthiazole-5-carboxylic acid and 2-(6-chlorobenzoimidazol-1-yl)-4-phenylthiazole-5-carboxylic acid were prepared in a similar manner as that for Example 1 starting with the reaction of 5-chlorobenzoimidazole (Aldrich) and 2-Chloro-4-phenylthiazole-5-carboxylic acid ethyl ester. MS M/z 356 (M+1).

Example 15

2-(5-Methylbenzoimidazol-1-yl)-4-phenylthiazole-5-carboxylic acid and 2-(6-Methylbenzoimidazol-1-yl)-4-phenylthiazole-5-carboxylic acid

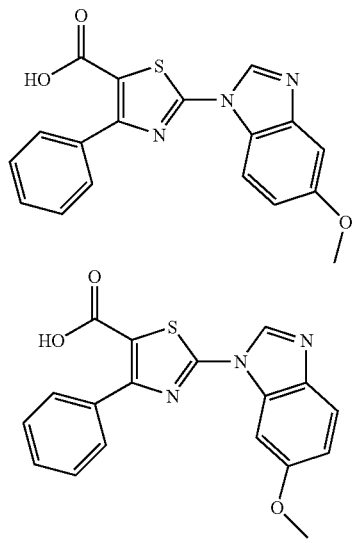

2-(5-Methylbenzoimidazol-1-yl)-4-phenylthiazole-5-carboxylic acid and 2-(6-Methylbenzoimidazol-1-yl)-4-phenylthiazole-5-carboxylic acid were prepared in a similar manner as that for Example 1 starting with the reaction of 5-methoxy-benzoimidazole and 2-Chloro-4-phenylthiazole-5-carboxylic acid ethyl ester. 1H-NMR (DMSO-D6) 8.88 (d, 1H); 8.17 (d, ½H); 7.80 (s, ½H); 7.82-7.92 (m, 2H); 7.71 (d, 1H); 7.41-7.54 (m, 3H); 7.00-7.13 (m, 1H); 3.82 (s, 3H). MS M/z 351 (M+1).

Example 16

2-(5-Chloro-6-methylbenzoimidazol-1-yl)-4-phenylthiazole-5-carboxylic acid and 2-(6-chloro-5-methylbenzoimidazol-1-yl)-4-phenylthiazole-5-carboxylic acid

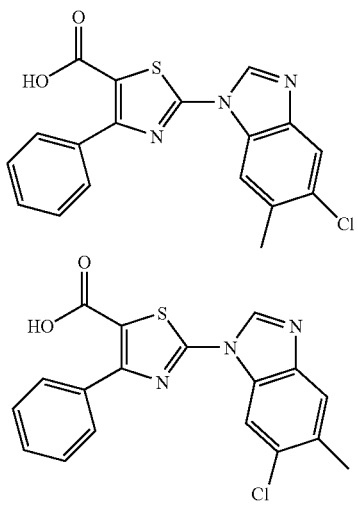

2-(5-Chloro-6-methylbenzoimidazol-1-yl)-4-phenylthiazole-5-carboxylic acid and 2-(6-chloro-5-methylbenzoimidazol-1-yl)-4-phenylthiazole-5-carboxylic acid were prepared in a similar manner as that for Example 1 starting with the reaction of 5-Chloro-6-methylbenzoimidazole and 2-Chloro-4-phenylthiazole-5-carboxylic acid ethyl ester. MS M/z 370 (M+1).

Example 17

2-(5,6-Dimethoxy-benzoimidazol-1-yl)-4-(3-methoxy-phenyl)-thiazole-5-carboxylic acid

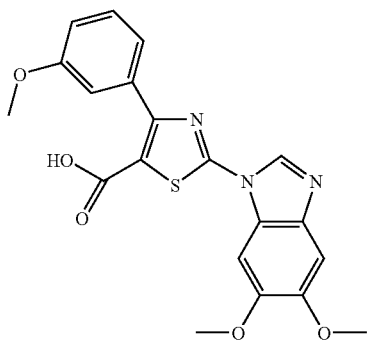

In a similar manner as described for Example 26, 4-bromo-2-(5,6-dimethoxy-benzoimidazol-1-yl)-thiazole-5-carboxylic acid methyl ester (40 mg, 0.1 mmol) and 3-methoxyphenylboronic acid (22.8 mg, 0.15 mmol) gave 2-(5,6-Dimethoxy-benzoimidazol-1-yl)-4-(3-methoxy-phenyl)-thiazole-5-carboxylic acid (17.6 mg, 43%) as a white solid. 1H NMR (400 MHz, DMSO-$d_6$) δ ppm 13.63 (br.s., 1 H); 8.83 (s, 1 H); 7.83 (s, 1 H); 7.49-7.54 (m, 2 H); 7.40 (s, 1 H); 7.41 (t, 1 H); 7.06 (ddd, 1 H); 3.86 (s, 3 H); 3.85(s, 3 H); 3.82 (s, 3 H). MS m/z 412 (M+1).

Example 18

2-(5,6-Dimethoxy-benzoimidazol-1-yl)-4-(3,4-dimethoxy-phenyl)-thiazole-5-carboxylic acid

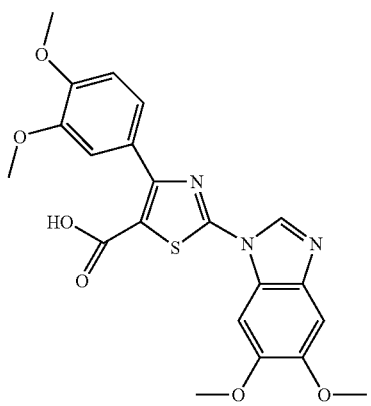

In a similar manner as described for Example 26, 4-bromo-2-(5,6-dimethoxy-benzoimidazol-1-yl)-thiazole-5-carboxylic acid methyl ester (40 mg, 0.1 mmol) and 3,4-dimethoxyphenylboronic acid (27.3 mg, 0.15 mmol) gave 2-(5,6-Dimethoxy-benzoimidazol-1-yl)-4-(3,4-dimethoxy-phenyl)-thiazole-5-carboxylic acid (26.4 mg, 60%) as a white solid. 1H NMR (400 MHz, DMSO-$d_6$) δ ppm 13.45 (br.s., 1 H); 8.83 (s, 1 H); 7.86 (s, 1 H); 7.66 (d, 1 H); 7.60 (dd, 1 H); 7.40 (s, 1 H); 7.08 (d, 1H); 3.87 (s, 3 H); 3.85 (s, 3 H); 3.84 (s, 3 H); 3.82 (s, 3 H). MS m/z 442 (M+1).

Example 19

4-(3-Chloro-4-fluoro-phenyl)-2-(5,6-dimethoxy-benzoimidazol-1-yl)-thiazole-5-carboxylic acid

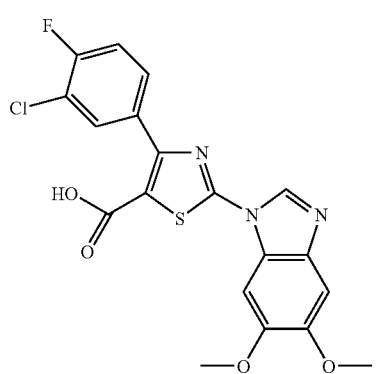

In a similar manner as described for Example 26, 4-bromo-2-(5,6-dimethoxy-benzoimidazol-1-yl)-thiazole-5-carboxylic acid methyl ester (40 mg, 0.1 mmol) and 3-chloro-4-fluorophenylboronic acid (26.2 mg, 0.15 mmol) gave 4-(3-Chloro-4-fluoro-phenyl)-2-(5,6-dimethoxy-benzoimidazol-1-yl)-thiazole-5-carboxylic acid (8.2 mg, 19%) as a white solid. 1H NMR (400 MHz, DMSO-$d_6$) δ ppm 13.79 (br.s., 1H); 8.84 (s, 1 H,); 8.22 (dd, 1 H) 8.01 (ddd, 1 H); 7.81 (s, 1 H); 7.57 (t, 1H); 7.39 (s, 1 H); 3.87 (s, 3 H); 3.85 (s, 3 H). MS m/z 434 (M+1).

Example 20

2-(5,6-Dimethoxy-benzoimidazol-1-yl)-4-(3-fluoro-phenyl)-thiazole-5-carboxylic acid

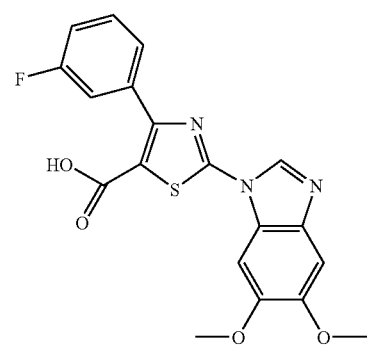

In a similar manner as described for Example 26, 4-bromo-2-(5,6-dimethoxy-benzoimidazol-1-yl)-thiazole-5-carboxylic acid methyl ester (40 mg, 0.1 mmol) and 3-fluorophenylboronic acid (21 mg, 0.15 mmol) gave 2-(5,6-Dimethoxybenzoimidazol-1-yl)-4-(3-fluoro-phenyl)-thiazole-5-carboxylic acid (7.8 mg, 20%) as a white solid. MS 400 m/z (M+1).

Example 21

4-(2-Chloro-phenyl)-2-(5,6-dimethoxy-benzoimidazol-1-yl)-thiazole-5-carboxylic acid

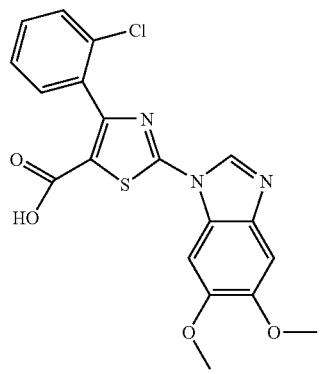

In a similar manner as described for Example 26, 4-bromo-2-(5,6-dimethoxy-benzoimidazol-1-yl)-thiazole-5-carboxylic acid methyl ester (40 mg, 0.1 mmol) and 2-chlorophenylboronic acid (23.5 mg, 0.15 mmol) gave 4-(2-Chloro-phenyl)-2-(5,6-dimethoxy-benzoimidazol-1-yl)-thiazole-5-carboxylic acid (19.2 mg, 46%) as a white solid. 1H NMR (400 MHz, DMSO-$d_6$) δ ppm 13.63 (br.s., 1 H); 8.82 (s, 1 H); 7.73 (s, 1 H); 7.59-7.65 (m, 2 H); 7.51 (td, 1 H); 7.46 (d, 1H); 7.39 (s, 1 H); 3.85 (s, 3 H); 3.81 (s, 3 H). MS m/z 416 (M+1).

Example 22

4-Benzo[1,3]dioxol-5-yl-2-(5,6-dimethoxy-benzoimidazol-1-yl)-thiazole-5-carboxylic acid

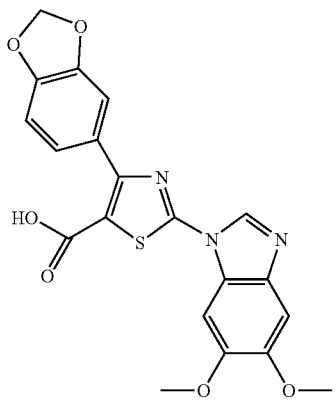

In a similar manner as described for Example 26, 4-bromo-2-(5,6-dimethoxy-benzoimidazol-1-yl)-thiazole-5-carboxylic acid methyl ester (40 mg, 0.1 mmol) and 3,4-methylenedioxybenzeneboronic acid (24.9 mg, 0.15 mmol) gave 4-Benzo[1,3]dioxol-5-yl-2-(5,6-dimethoxy-benzoimidazol-1-yl)-thiazole-5-carboxylic acid (10.5 mg, 25%) as a white solid. MS m/z 426 (M+1).

Example 23

4-(3,4-Dichloro-phenyl)-2-(5,6-dimethoxy-benzoimidazol-1-yl)-thiazole-5-carboxylic acid

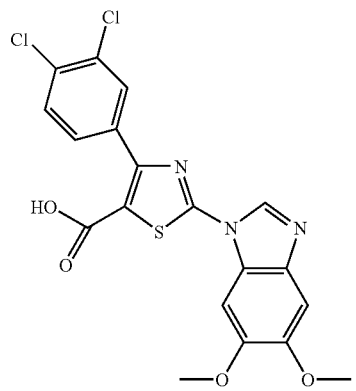

In a similar manner as described for Example 26, 4-bromo-2-(5,6-dimethoxy-benzoimidazol-1-yl)-thiazole-5-carboxylic acid methyl ester (40 mg, 0.1 mmol) and 3,4-dichlorophenylboronic acid (28.6 mg, 0.15 mmol) gave 4-(3,4-Dichloro-phenyl)-2-(5,6-dimethoxy-benzoimidazol-1-yl)-thiazole-5-carboxylic acid (15.9 mg, 35%) as a white solid. 1H NMR (400 MHz, DMSO-$d_6$) δ ppm 13.81 (br.s., 1 H); 8.85 (s, 1 H); 8.25 (d, 1 H); 7.97 (dd, 1 H); 7.81 (s, 1 H); 7.79 (d, 1 H); 7.39 (s, 1 H); 3.85 (s, 3 H); 3.87 (s, 3 H). MS m/z 450 (M+1).

Example 24

2-(5,6-Dimethoxy-benzoimidazol-1-yl)-4-(3-isopropyl-phenyl)-thiazole-5-carboxylic acid

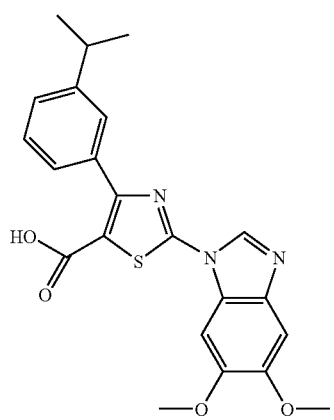

In a similar manner as described for Example 26, 4-bromo-2-(5,6-dimethoxy-benzoimidazol-1-yl)-thiazole-5-carboxylic acid methyl ester (40 mg, 0.1 mmol) and 3-isopropylphenylboronic acid (24.6 mg, 0.15 mmol) gave 2-(5,6-Dimethoxy-benzoimidazol-1-yl)-4-(3-isopropyl-phenyl)-thiazole-5-carboxylic acid (18.6 mg, 44%) as a white solid. 1H NMR (400 MHz, DMSO-$d_6$) δ ppm 13.61 (br.s., 1 H); 8.83 (s, 1 H); 7.88 (s, 1 H); 7.83 (t, 1 H); 7.74 (dt, 1 H); 7.39 (s, 1 H); 7.40 (t, 1 H); 7.36 (dt, 1 H); 3.86 (s, 3 H); 3.85 (s, 3 H); 2.93-3.03 (m, 1 H); 1.26 (d, 6 H). MS m/z 424 (M+1).

Example 25

2-(5,6-Dimethoxy-benzoimidazol-1-yl)-4-thiophen-3-yl-thiazole-5-carboxylic acid

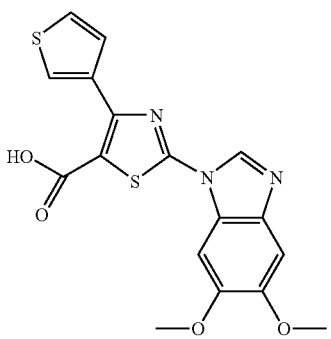

In a similar manner as described for Example 26, 4-bromo-2-(5,6-dimethoxy-benzoimidazol-1-yl)-thiazole-5-carboxylic acid methyl ester (40 mg, 0.1 mmol) and thiophene-3-boronic acid (19.2 mg, 0.15 mmol) gave 2-(5,6-Dimethoxy-benzoimidazol-1-yl)-4-thiophen-3-yl-thiazole-5-carboxylic acid (30.1 mg, 78%) as a white solid. 1H NMR (400 MHz, DMSO-$d_6$) δ ppm 13.74 (br.s., 1 H); 8.84 (s, 1 H); 8.55 (dd, 1 H); 7.91 (dd, 1 H); 7.86 (s, 1 H); 7.66 (dd, 1 H); 7.40 (s, 1 H); 3.891 (s, 3 H); 3.85 (s, 3 H)=. MS m/z 388 (M+1).

Example 26

2-(5,6-Dimethoxy-benzoimidazol-1-yl)-4-p-tolyl-thiazole-5-carboxylic acid methyl

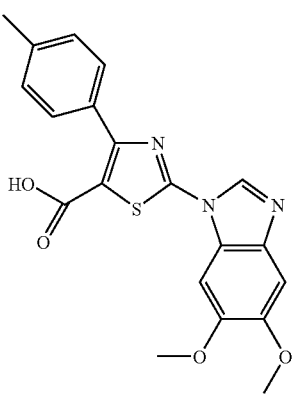

To a solution of 4-bromo-2-(5,6-dimethoxy-benzoimidazol-1-yl)-thiazole-5-carboxylic acid methyl ester (40 mg, 0.1 mmol), 4-methylphenylboronic acid (20.4 mg, 0.15 mmol) in ethylene glycol dimethyl ether (1 ml) was added $Na_2CO_3$ (2M, 100 μL, 0.2 mmol) and [1,1'-bis(diphenylphosphino)-ferrocene]dichloro palladium(II) (4 mg, 0.005 mmol). The mixture was heated to 100° C. for 3 hrs. The solvent was evaporated and 2 ml water was added. It was then extracted with 2×3 ml EtOAc. The combined organics were concentrated in vacuo. To this crude was added THF (0.5 ml), water (0.5 ml), methanol (0.2 ml) and NaOH (20 mg, 0.05 mmol). The mixture was heated to 60° C. for 3 hrs. The solvents were evaporated and the crude was purified by prep-HPLC to afford 2-(5,6-Dimethoxy-benzoimidazol-1-yl)-4-p-tolyl-thiazole-5-carboxylic acid (21.1 mg, 53%) as a white solid. 1H NMR (400 MHz, DMSO-$d_6$) δ ppm 13.57 (br.s., 1H); 8.82 (s, 1 H); 7.83 (m, 3 H); 7.39 (s, 1 H); 7.31 (d, 2 H); 3.86 (s, 3 H); 3.85(s, 3 H), 2.39 (s, 3H). MS m/z 396 (M+1).

Example 27

2-(5,6-Dimethoxy-benzoimidazol-1-yl)-4-o-tolyl-thiazole-5-carboxylic acid

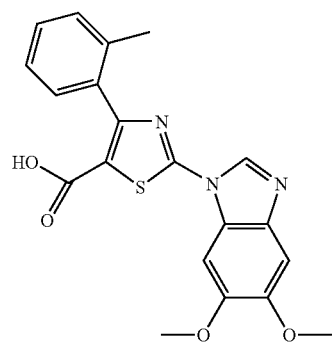

In a similar manner as described for Example 26, 4-bromo-2-(5,6-dimethoxy-benzoimidazol-1-yl)-thiazole-5-carboxylic acid methyl ester (40 mg, 0.1 mmol) and 2-methylphenyl-boronic acid (20.4 mg, 0.15 mmol) gave 2-(5,6-Dimethoxy-benzoimidazol-1-yl)-4-o-tolyl-thiazole-5-carboxylic acid (22.5 mg, 57%) as a white solid. 1H NMR (400 MHz, DMSO-$d_6$) δ ppm 13.43 (br.s., 1 H); 8.82 (s, 1 H); 7.68 (s, 1 H); 7.41 (d, 1 H); 7.40 (s, 1 H); 7.31-7.39 (m, 2 H); 7.27 (td, 1 H); 3.85 (s, 3 H); 3.81 (s, 3 H); 2.29 (s, 3 H). MS m/z 396 (M+1).

Example 28

2-(5,6-Dimethoxy-benzoimidazol-1-yl)-4-(4-methoxy-phenyl)-thiazole-5-carboxylic acid

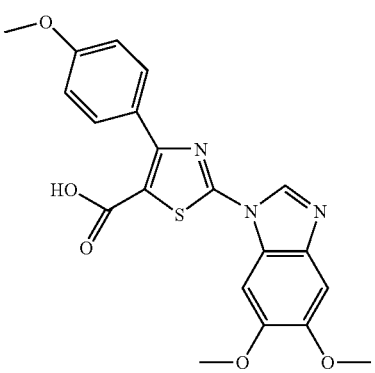

In a similar manner as described for Example 26, 4-bromo-2-(5,6-dimethoxy-benzoimidazol-1-yl)-thiazole-5-carboxylic acid methyl ester (40 mg, 0.1 mmol) and 4-methoxyphenylboronic acid (22.8 mg, 0.15 mmol) gave 2-(5,6-Dimethoxy-benzoimidazol-1-yl)-4-(4-methoxy-phenyl)-thiazole-5-carboxylic acid (20.3 mg, 49%) as a white solid. 1H NMR (400 MHz, DMSO-$d_6$) δ ppm 13.53 (br.s., 1 H);

8.82 (s, 1 H); 7.94 (d, 1 H); 7.83 (s, 1 H); 7.39 (s, 1 H); 7.05 (d, 1 H); 3.87 (s, 3 H); 3.85 (s, 3 H); 3.84 (s, 3 H). MS m/z 412 (M+1).

Example 29

4-(2,3-Difluoro-phenyl)-2-(5,6-dimethoxy-benzoimidazol-1-yl)-thiazole-5-carboxylic acid

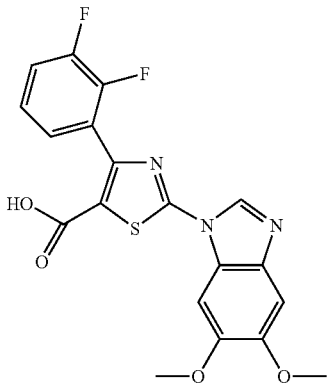

In a similar manner as described for Example 26, 4-bromo-2-(5,6-dimethoxy-benzoimidazol-1-yl)-thiazole-5-carboxylic acid methyl ester (40 mg, 0.1 mmol) and 2,3-difluorophenylboronic acid (23.7 mg, 0.15 mmol) gave 4-(2,3-Difluoro-phenyl)-2-(5,6-dimethoxy-benzoimidazol-1-yl)-thiazole-5-carboxylic acid (16.2 39%) as a white solid. 1H NMR (400 MHz, DMSO-$d_6$) δ ppm 13.81 (br.s., 1 H); 8.83 (s, 1 H); 7.74 (s, 1 H); 7.52-7.64 (m, 2 H); 7.40 (s, 1 H); 7.33-7.39 (m, 1 H); 3.85 (s, 3 H); 3.83 (s, 3 H). MS m/z 418 (M+1).

Example 30

2-(5,6-Dimethoxy-benzoimidazol-1-yl)-4-(2-hydroxy-phenyl)-thiazole-5-carboxylic acid

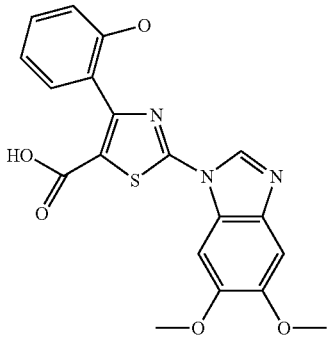

In a similar manner as described for Example 26, 4-bromo-2-(5,6-dimethoxy-benzoimidazol-1-yl)-thiazole-5-carboxylic acid methyl ester (40 mg, 0.1 mmol) and 2-(4,4,5,5-tetramethyl-1,3,2-dioxaborolan-2-yl)phenol (33.0 mg, 0.15 mmol) gave 2-(5,6-Dimethoxy-benzoimidazol-1-yl)-4-(2-hydroxy-phenyl)-thiazole-5-carboxylic acid (3.5 mg, 9%) as a white solid. MS m/z 398 (M+1).

Example 31

4-(3-Chloro-phenyl)-2-(5,6-dimethoxy-benzoimidazol-1-yl)-thiazole-5-carboxylic acid

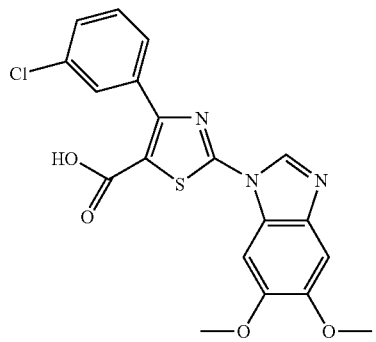

In a similar manner as described for Example 26, 4-bromo-2-(5,6-dimethoxy-benzoimidazol-1-yl)-thiazole-5-carboxylic acid methyl ester (40 mg, 0.1 mmol) and 3-chlorophenylboronic acid (23.5 mg, 0.15 mmol) gave 4-(3-Chloro-phenyl)-2-(5,6-dimethoxy-benzoimidazol-1-yl)-thiazole-5-carboxylic acid (8.6 mg, 21%) as a white solid. MS m/z 416 (M+1).

Example 32

2-(5,6-Dimethoxy-benzoimidazol-1-yl)-4-naphthalen-1-yl-thiazole-5-carboxylic acid

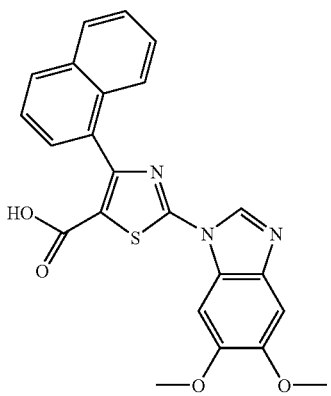

In a similar manner as described for Example 26, 4-bromo-2-(5,6-dimethoxy-benzoimidazol-1-yl)-thiazole-5-carboxylic acid methyl ester (40 mg, 0.1 mmol) and 1-naphthaleneboronic acid (25.8 mg, 0.15 mmol) gave 2-(5,6-Dimethoxy-benzoimidazol-1-yl)-4-naphthalen-1-yl-thiazole-5-carboxylic acid (15.9 mg, 37%) as a white solid. 1H NMR (400 MHz, DMSO-$d_6$) δ ppm 13.41 (br.s., 1 H); 8.85 (s, 1 H); 8.01-8.09 (m, 2H); 7.92 (dd, 1 H); 7.72 (dd, 1 H); 7.69 (s, 1H); 7.50-7.65 (m, 3H); 7.40 (s, 1 H); 3.84 (s, 3 H); 3.68 (s, 3 H). MS m/z 432 (M+1).

Example 33

2-(5,6-Dimethoxy-benzoimidazol-1-yl)-4-pyridin-3-yl-thiazole-5-carboxylic acid

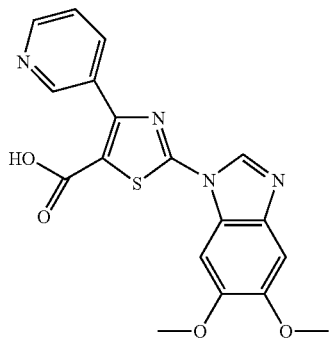

In a similar manner as described for Example 26, 4-bromo-2-(5,6-dimethoxy-benzoimidazol-1-yl)-thiazole-5-carboxylic acid methyl ester (40 mg, 0.1 mmol) and pyridine-3-boronic acid (18.4 mg, 0.15 mmol) gave 2-(5,6-Dimethoxy-benzoimidazol-1-yl)-4-pyridin-3-yl-thiazole-5-carboxylic acid (2.6 mg, 7%) as a white solid. 1H NMR (400 MHz, DMSO-$d_6$) δ ppm 13.68 (br.s., 1 H); 9.07 (d, 1H); 8.85 (s, 1 H); 8.66 (dd, 1 H); 8.31 (dt, 1 H); 7.81 (s, 1 H); 7.55 (ddd, 1 H); 7.40 (s, 1 H); 3.86 (s, 3 H); 3.85 (s, 3 H). MS m/z 383 (M+1).

Example 34

2-(5,6-Dimethoxy-benzoimidazol-1-yl)-4-(3-hydroxy-phenyl)-thiazole-5-carboxylic acid

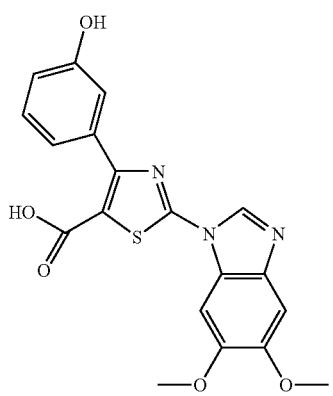

In a similar manner as described for Example 26, 4-bromo-2-(5,6-dimethoxy-benzoimidazol-1-yl)-thiazole-5-carboxylic acid methyl ester (40 mg, 0.1 mmol) and 3-hydroxyphenylboronic acid (20.7 mg, 0.15 mmol) gave 2-(5,6-Dimethoxy-benzoimidazol-1-yl)-4-(3-hydroxy-phenyl)-thiazole-5-carboxylic acid (2.4 mg, 6%) as a white solid. MS m/z 398 (M+1).

Example 35

2-(5-Chloro-6-fluoro-benzoimidazol-1-yl)-4-phenyl-thiazole-5-carboxylic acid and 2-(6-chloro-5-fluoro-benzoimidazol-1-yl)-4-phenyl-thiazole-5-carboxylic acid

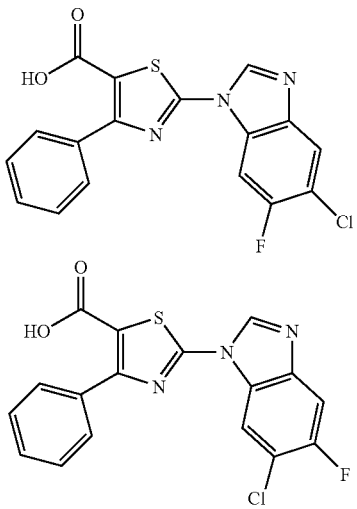

2-(5-Chloro-6-fluoro-benzoimidazol-1-yl)-4-phenyl-thiazole-5-carboxylic acid and 2-(6-chloro-5-fluoro-benzoimidazol-1-yl)-4-phenyl-thiazole-5-carboxylic acid were prepared in a similar manner as that for Example 1 starting with the reaction of 5-chloro-6-fluorobenzoimidazole and 2-Chloro-4-phenylthiazole-5-carboxylic acid ethyl ester. MS M/z 374 (M+1).

Example 36

4-(3-Chloro-phenyl)-2-(5,6-dimethoxy-benzoimidazol-1-yl)-thiazole-5-carboxylic acid amide

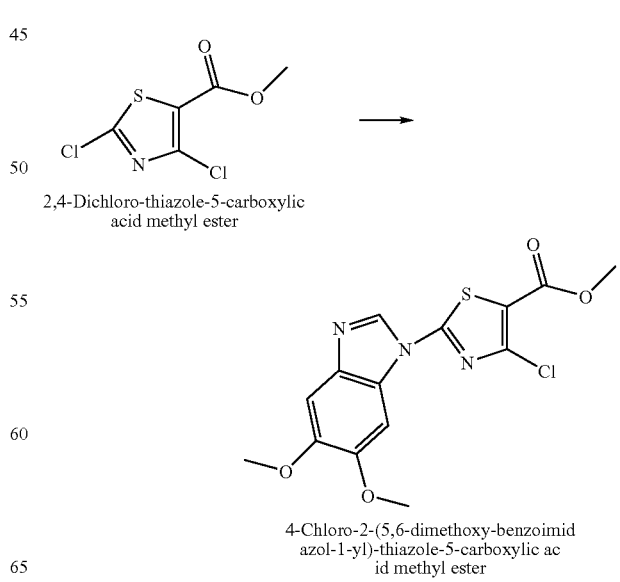

A suspension of sodium hydride (60%, 638 mg, 15.93 mmol) in dry dimethylformamide (30 ml) was cooled to 0° C. (ice bath). 5,6-Dimethoxybenzimidazole (1.42 g, 7.96 mmol) was added in one portion and the mixture was stirred at 0° C. for 15 min. A solution of 2,4-dichloro-thiazole-5-carboxylic acid methyl ester (1.69 g, 7.96 mmol) in dry dimethylformamide (10 ml) was added dropwise at 0° C. and stirring was continued for 15 min. The reaction was quenched at 0° C. with 1N aqueous hydrochloric acid (30 ml). The resulting precipitate was collected by filtration, washed with water and dried in a vacuum oven to give the desired product as a beige solid (2.64 g, 94% yield). LC-MS m/e 340.0 (M+H$^+$)

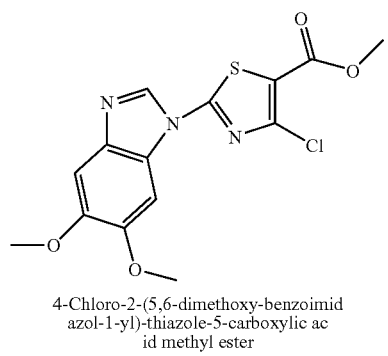

4-Chloro-2-(5,6-dimethoxy-benzoimidazol-1-yl)-thiazole-5-carboxylic acid methyl ester

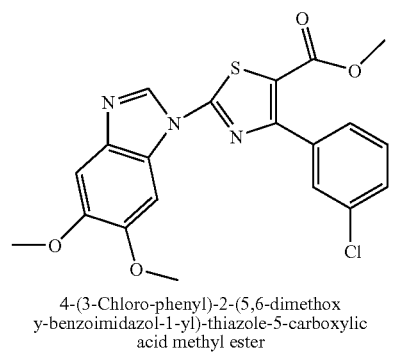

4-(3-Chloro-phenyl)-2-(5,6-dimethoxy-benzoimidazol-1-yl)-thiazole-5-carboxylic acid methyl ester A solution of 4-chloro-2-(5,6-dimethoxy-benzoimidazol-1-yl)-thiazole-5-carboxylic acid methyl ester (1.00 g, 2.83 mmol) in DME (15 ml)/2M Na$_2$CO$_3$ (4.94 ml, 9.9 mmol) was treated with 3-chlorophenylboronic acid (660 mg, 4.24 mmol) and Pd[PPh$_3$]$_4$ (320 mg, 0.285 mmol) for 20 min at 120° C. in a microwave synthesizer. The reaction was quenched with water at rt and the precipitate was collected by suction filtration, washed with water and dried in a vacuum oven. The crude was absorbed on silica and purified on a silica gel column with a 30-100% ethyl acetate/hexanes gradient over 30 min to afford the product as a beige solid (850 mg, 70% yield). LC-MS m/e 430.0 (M+H$^+$)

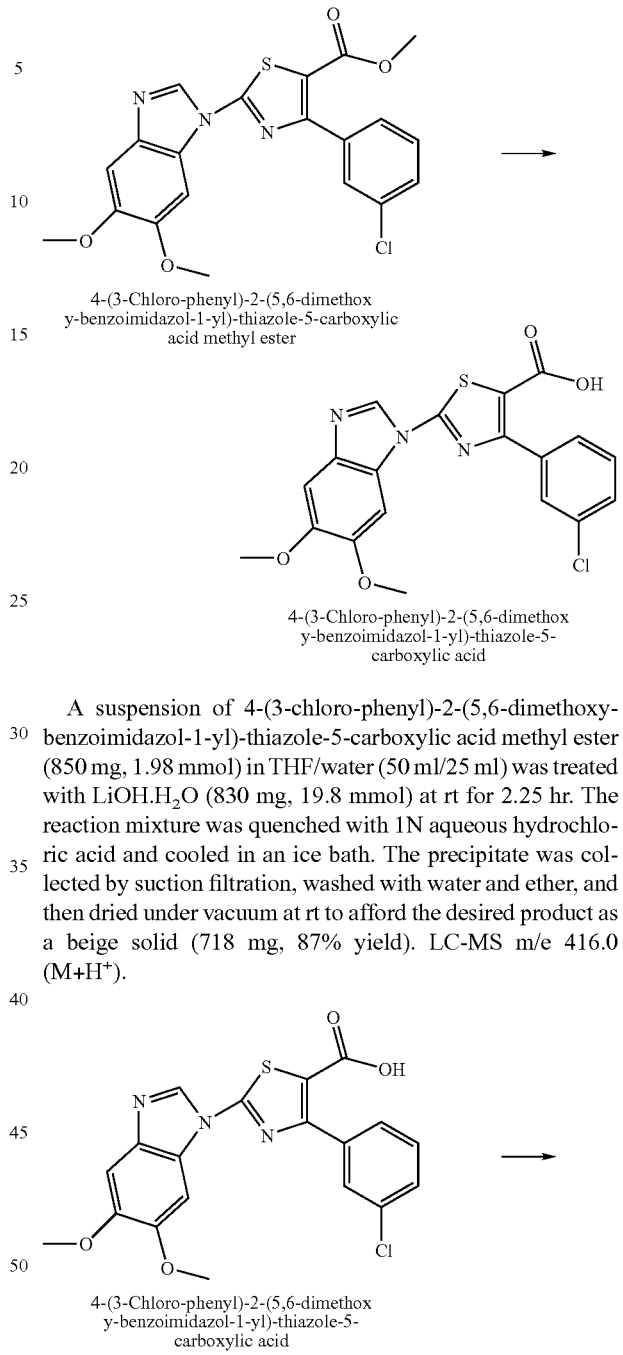

A suspension of 4-(3-chloro-phenyl)-2-(5,6-dimethoxy-benzoimidazol-1-yl)-thiazole-5-carboxylic acid methyl ester (850 mg, 1.98 mmol) in THF/water (50 ml/25 ml) was treated with LiOH.H$_2$O (830 mg, 19.8 mmol) at rt for 2.25 hr. The reaction mixture was quenched with 1N aqueous hydrochloric acid and cooled in an ice bath. The precipitate was collected by suction filtration, washed with water and ether, and then dried under vacuum at rt to afford the desired product as a beige solid (718 mg, 87% yield). LC-MS m/e 416.0 (M+H$^+$).

HBTU (228 mg, 0.60 mol) was added at rt in 2 portions over 90 min to a solution of 4-(3-chloro-phenyl)-2-(5,6-dimethoxy-benzoimidazol-1-yl)-thiazole-5-carboxylic acid (30 mg, 0.07 mmol), ammonium bicarbonate (30 mg, 0.35 mmol) and triethylamine (0.10 ml, 0.70 mmol) in NMP (1 ml). The reaction was quenched with water at rt and the precipitate was collected by suction filtration. This crude product was absorbed on silica and purified on a silica gel column with 100% ethyl acetate to afford the product as a white solid (25 mg, 84% yield). LC-MS m/e 415.0 (M+H+)

Example 37

2-(5,6-Dimethoxy-benzoimidazol-1-yl)-4-phenyl-thiazole-5-carboxylic acid phenylamide

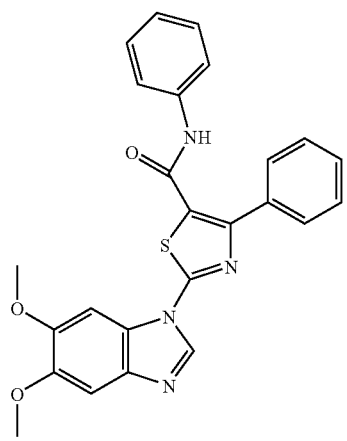

To a solution of 2-(5,6-Dimethoxy-benzoimidazol-1-yl)-4-phenyl-thiazole-5-carboxylic acid (30 mg, 0.075 mmol) in dimethylformamide (1 ml) was added diethylisopropylamine (15.6 μL, 0.09 mmol) and HATU (28.5 mg, 0.075 mmol). The mixture was stirred under ambient temperature for 5 min. Aniline (6.8 μL, 0.075 mmol) was added. The mixture was stirred for 1 hr. Ethyl acetate (5 ml) was added. The mixture was washed with water (2×3 ml), brine, dried with magnesium sulfate and concentrated in vacuo. The crude was purified with flash chromatography (0 to 2% methanol dichloromethane) to afford 2-(5,6-Dimethoxy-benzoimidazol-1-yl)-4-phenyl-thiazole-5-carboxylic acid phenylamide (30 mg, 86.4%) as a yellow solid. MS m/z 457 (M+1).

Example 38

2-(5,6-Dihydroxy-benzoimidazol-1-yl)-4-phenyl-thiazole-5-carboxylic acid ethyl ester

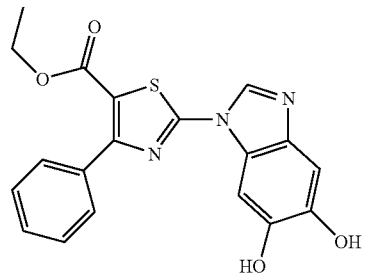

Boron trifluoride dimethylsulfide (4.1 ml, 39 mmol) was added in multiportions over 5 hrs. to a suspension of 2-(5,6-Dimethoxybenzoimidazol-1-yl)-4-phenylthiazole-5-carboxylic acid ethyl ester (2.04 g, 4.99 mmol) in methylene chloride at RT. The mixture was stirred for an additional 40 mins. Ice water was added. Methylene chloride was removed, the residue was filtered, the solid was washed with water and a small amount of methanol, and then dried in air to give the product (1.72 g, yield 90%). 1H-NMR (DMSO-D6) 8.72 (s, 1H); 8.78-8.88 (m, 2H); 7.64 (s, 1H); 7.42-7.51 (m, 3H); 7.08 (s, 1H); 4.22 (q, 2H), 1.22 (t, 3H). MS M/z 382 (M+1)

Example 39

2-(5,6-Dihydroxybenzoimidazol-1-yl)-4-phenyl-thiazole-5-carboxylic acid

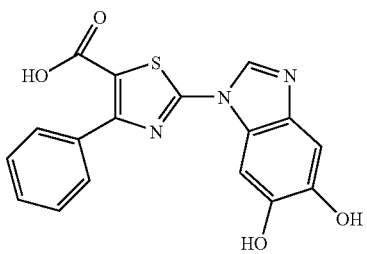

2-(5,6-Dihydroxybenzoimidazol-1-yl)-4-phenylthiazole-5-carboxylic acid was prepared in a similar manner as that for Example 1 by hydrolysis under basic, aqueous conditions with LiOH at room temperature starting with the reaction of 5,6-hydroxybenzoimidazole and 2-Chloro-4-phenylthiazole-5-carboxylic acid ethyl ester. ¹H-NMR (DMSO-D6) 9.47 (s, 1H); 9.07 (s, 1H); 8.67 (s, 1H); 7.84-7.80 (m, 2H); 7,63 (s, 1H); 7.50-7.41 (m, 3H); 7.06 (s, 1H). MS M/z 354 (M+1).

Example 40

2-(5,6-Dimethoxy-benzoimidazol-1-yl)-4-(3-vinyl-phenyl)-thiazole-5-carboxylic acid

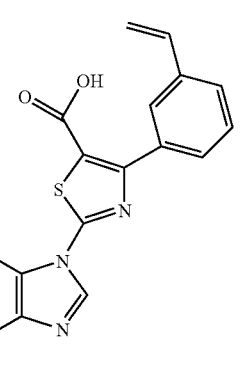

In a similar manner as described for Example 26, 4-bromo-2-(5,6-dimethoxy-benzoimidazol-1-yl)-thiazole-5-carboxylic acid methyl ester (40 mg, 0.1 mmol) and 3-vinylphenylboronic acid (22 mg, 0.15 mmol) gave 2-(5,6-Dimethoxy-benzoimidazol-1-yl)-4-(3-vinyl-phenyl)-thiazole-5-carboxylic acid (26 mg, 64%) as a white solid. 1H NMR (400 MHz, DMSO-$d_6$) δ ppm 8.84 (s, 1 H); 8.04 (t, 1 H); 7.85 (s, 1 H); 7.83 (dt, 1 H); 7.59 (dt, 1 H); 7.48 (t, 1 H); 7.40 (s, 1 H); 6.83 (dd, 1 H); 5.92 (dd, 1 H); 5.33 (dd, 1H); 3.86 (s, 3 H); 3.85 (s, 3 H). MS 408 m/z (M+1).

Example 41

4-(3,5-Dichloro-phenyl)-2-(5,6-dimethoxy-benzoimidazol-1-yl)-thiazole-5-carboxylic acid

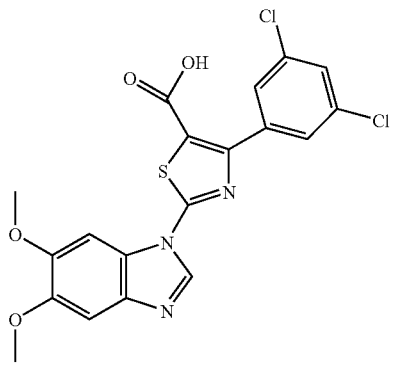

In a similar manner as described for Example 26, 4-bromo-2-(5,6-dimethoxy-benzoimidazol-1-yl)-thiazole-5-carboxylic acid methyl ester (40 mg, 0.1 mmol) and 3,5-dichlorophenylboronic acid (27 mg, 0.15 mmol) gave 4-(3,5-Dichloro-phenyl)-2-(5,6-dimethoxy-benzoimidazol-1-yl)-thiazole-5-carboxylic acid (23 mg, 51%) as a white solid. 1H NMR (400 MHz, DMSO-$d_6$) δ ppm 8.84 (s, 1 H); 8.15 (s, 2 H); 7.83 (s, 1 H); 7.73 (s, 1 H); 7.39 (s, 1 H); 3.89 (s, 3 H); 3.85 (s, 3 H). MS 450 m/z (M+1).

Example 42

4-(3-Bromo-phenyl)-2-(5,6-dimethoxy-benzoimidazol-1-yl)-thiazole-5-carboxylic acid

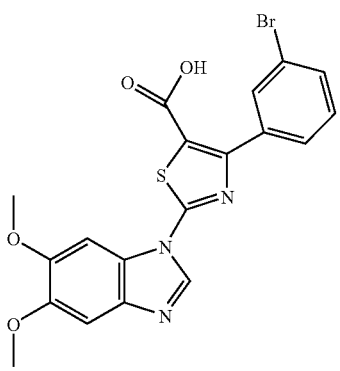

In a similar manner as described for Example 26, 4-bromo-2-(5,6-dimethoxy-benzoimidazol-1-yl)-thiazole-5-carboxylic acid methyl ester (40 mg, 0.1 mmol) and 3-bromophenylboronic acid (30 mg, 0.15 mmol) gave 4-(3-Bromo-phenyl)-2-(5,6-dimethoxy-benzoimidazol-1-yl)-thiazole-5-carboxylic acid (4.0 mg, 9%) as a white solid. MS 460 m/z (M+1).

Example 43

2-(5,6-Dimethoxy-benzoimidazol-1-yl)-4-(3-trifluoromethyl-phenyl)-thiazole-5-carboxylic acid

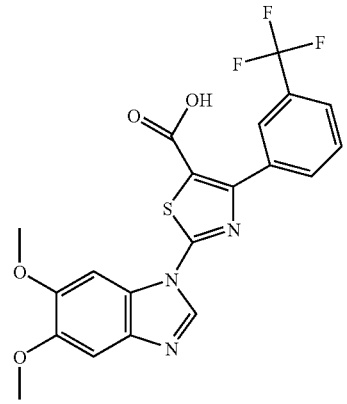

In a similar manner as described for Example 26, 4-bromo-2-(5,6-dimethoxy-benzoimidazol-1-yl)-thiazole-5-carboxylic acid methyl ester (40 mg, 0.1 mmol) and 3-trifluoromethylphenylboronic acid (28.5 mg, 0.15 mmol) gave 2-(5,6-Dimethoxy-benzoimidazol-1-yl)-4-(3-trifluoromethyl-phenyl)-thiazole-5-carboxylic acid (26.1 mg, 58%) as a white solid. 1H NMR (400 MHz, DMSO-$d_6$) δ ppm 13.90 (br.s. 1H); 8.82 (s, 1 H); 8.37-8.47 (m, 2 H); 7.87 (s, 1 H); 7.82 (d, 1 H); 7.72 (t, 1 H); 7.39 (s, 1 H); 3.87 (s, 3 H); 3.85 (s, 3 H). MS 450 m/z (M+1).

Example 45

4-(3-Chloro-4-trifluoromethyl-phenyl)-2-(5,6-dimethoxy-benzoimidazol-1-yl)-thiazole-5-carboxylic acid

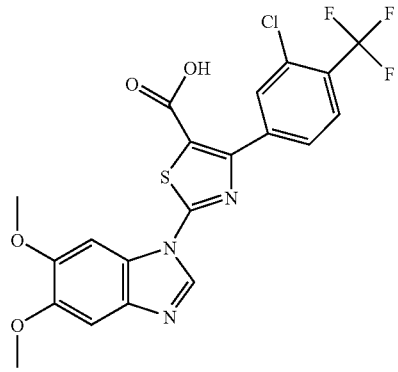

In a similar manner as described for Example 26, 4-bromo-2-(5,6-dimethoxy-benzoimidazol-1-yl)-thiazole-5-carboxylic acid methyl ester (40 mg, 0.1 mmol) and 3-chloro-4- trifluoromethylphenylboronic acid (33.7 mg, 0.15 mmol) gave 4-(3-Chloro-4-trifluoromethyl-phenyl)-2-(5,6-dimethoxy-benzoimidazol-1-yl)-thiazole-5-carboxylic acid (7.7 mg, 16%) as a white solid. 1H NMR (400 MHz, DMSO-d₆) δ ppm 13.91 (br.s., 1 H); 8.85 (s, 1 H); 8.48 (d, 1 H); 8.31 (dd, 1 H); 7.89 (d, 1 H); 7.84 (s, 1 H); 7.39 (s, 1 H); 3.86 (s, 3 H), 3.85 (s, 3H). MS 484 m/z (M+1).

Example 46

2-(5,6-Dimethoxy-benzoimidazol-1-yl)-4-(1-methyl-1H-indol-5-yl)-thiazole-5-carboxylic acid

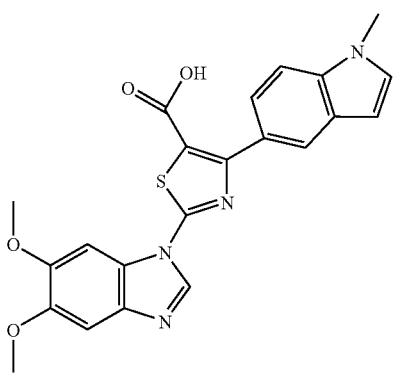

In a similar manner as described for Example 26, 4-bromo-2-(5,6-dimethoxy-benzoimidazol-1-yl)-thiazole-5-carboxylic acid methyl ester (40 mg, 0.1 mmol) and N-methylindole-5-boronic acid (26.2 mg, 0.15 mmol) gave 2-(5,6-Dimethoxy-benzoimidazol-1-yl)-4-(1-methyl-1H-indol-5-yl)-thiazole-5-carboxylic acid (5.1 mg, 12%) as a white solid. MS 435 m/z (M+1).

Example 47

4-(3,4-Difluoro-phenyl)-2-(5,6-dimethoxy-benzoimidazol-1-yl)-thiazole-5-carboxylic acid

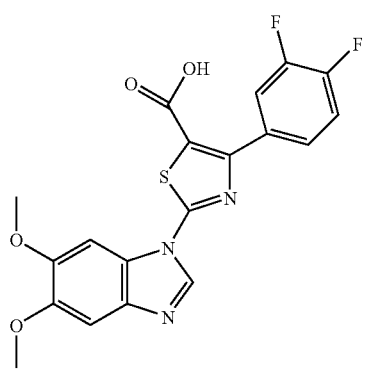

In a similar manner as described for Example 26, 4-bromo-2-(5,6-dimethoxy-benzoimidazol-1-yl)-thiazole-5-carboxylic acid methyl ester (40 mg, 0.1 mmol) and 3,4-difluorophenylboronic acid (23.7 mg, 0.15 mmol) gave 4-(3,4-Difluoro-phenyl)-2-(5,6-dimethoxy-benzoimidazol-1-yl)-thiazole-5-carboxylic acid (8.7 mg, 21%) as a white solid. 1H NMR (400 MHz, DMSO-d₆) δ ppm 8.81 (s, 1 H); 8.22-8.32 (m, 1 H); 7.88-8.00 (m, 1 H); 7.80 (s, 1 H); 7.55 (dt, 1 H); 7.39 (s, 1 H); 3.88 (s, 3 H), 3.85 (s, 3 H). MS 418 m/z (M+1).

Example 48

2-[5,6-Bis-(2-methoxy-ethoxy)-benzoimidazol-1-yl]-4-phenyl-thiazole-5-carboxylic acid

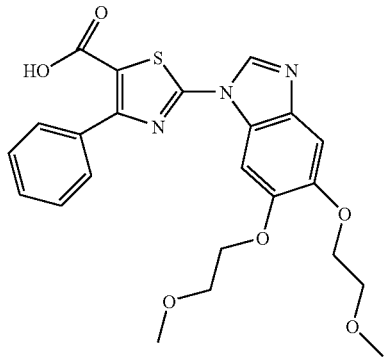

A mixture of 2-(5,6-dihydroxy-benzoimidazol-1-yl)-4-phenyl-thiazole-5-carboxylic acid ethyl ester (118.8 mg, 0.31 mmol, intermediate for Example 39), bromoethyl methyl ether (0.1 ml) and potassium carbonate (200 mg) in N-methylpyrrolidone (2 ml) was stirred at RT overnight and 80° C. for 4 hr. Water was added, and the mixture was extracted with ethyl acetate. After removal of solvent, the residue was diluted with methanol (3 ml) and sodium hydroxide solution (1N, 1.5 ml) was added. The mixture was stirred at RT for 105 min. Methanol was removed, the aqueous was neutralized to pH 3. The precipitate was collected and purified by preparative HPLC to give the desired product (24.6 mg, yield 17%). 1H-NMR (DMSO-D6) 8.71 (s, 1H); 8.20-8.27 (m, 2H); 7.83 (s, 1H); 7.24-7.41 (m, 3H); 4.17-4.22 (m, 4H); 3.66-3.75 (m, 4H); 3.33 (s, 6H). MS M/z 470 (M+1).

Example 49

2-(5,6-Dimethoxy-benzoimidazol-1-yl)-4-(3-hydroxymethyl-phenyl)-thiazole-5-carboxylic acid

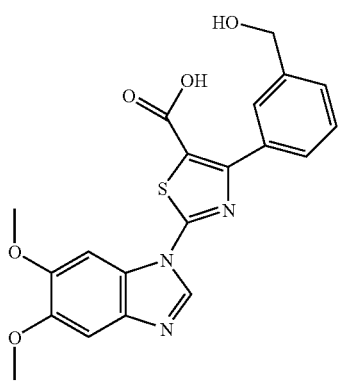

In a similar manner as described for Example 26, 4-bromo-2-(5,6-dimethoxy-benzoimidazol-1-yl)-thiazole-5-carboxylic acid methyl ester (40 mg, 0.1 mmol) and 3-hydroxymethylphenylboronic acid (22.9 mg, 0.15 mmol) gave 2-(5,6-

Dimethoxy-benzoimidazol-1-yl)-4-(3-hydroxymethyl-phenyl)-thiazole-5-carboxylic acid (0.8 mg, 2.0%) as a white solid. MS 412 m/z (M+1).

Example 50

4-(2,3-Dihydro-benzo[1,4]dioxin-6-yl)-2-(5,6-dimethoxy-benzoimidazol-1-yl)-thiazole-5-carboxylic acid

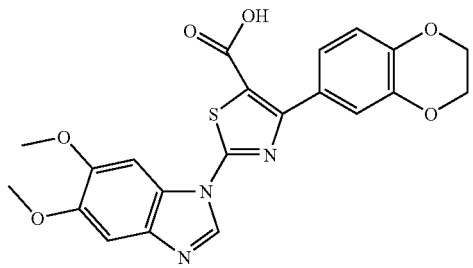

In a similar manner as described for Example 26, 4-bromo-2-(5,6-dimethoxy-benzoimidazol-1-yl)-thiazole-5-carboxylic acid methyl ester (40 mg, 0.1 mmol) and 1,4-benzodioxane-6-boronic acid (27 mg, 0.15 mmol) gave 4-(2,3-Dihydro-benzo[1,4]dioxin-6-yl)-2-(5,6-dimethoxy-benzoimidazol-1-yl)-thiazole-5-carboxylic acid (9.5 mg, 22%) as a white solid. MS 440 m/z (M+1).

Example 51

2-(5,6-Dimethoxy-benzoimidazol-1-yl)-4-(4-vinyl-phenyl)-thiazole-5-carboxylic acid

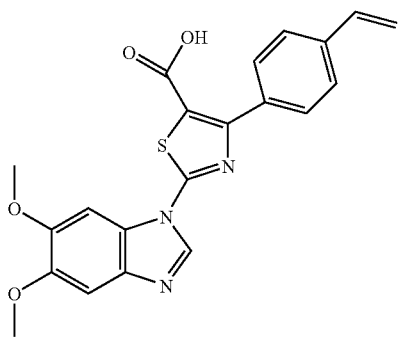

In a similar manner as described for Example 26, 4-bromo-2-(5,6-dimethoxy-benzoimidazol-1-yl)-thiazole-5-carboxylic acid methyl ester (40 mg, 0.1 mmol) and 4-vinylboronic acid (22.2 mg, 0.15 mmol) gave 2-(5,6-Dimethoxy-benzoimidazol-1-yl)-4-(4-vinyl-phenyl)-thiazole-5-carboxylic acid (15.2 mg, 37%) as a white solid. 1H NMR (400 MHz, DMSO-$d_6$) δ ppm 13.69 (br.s., 1 H); 8.82 (s, 1 H); 7.95 (d, 2 H); 7.84 (s, 1 H); 7.60 (d, 2H); 7.39 (s, 1H); 6.82 (dd, 1 H); 5.97 (dd, 1 H); 5.37 (dd, 1 H); 3.86 (s, 3 H); 3.86 (s, 3 H). MS 408 m/z (M+1).

Example 52

2-(5,6-Dimethoxy-benzoimidazol-1-yl)-4-(3-dimethylcarbamoyl-phenyl)-thiazole-5-carboxylic acid

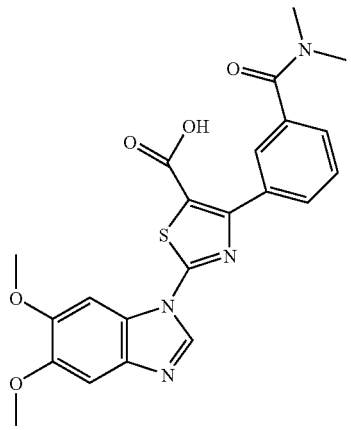

In a similar manner as described for Example 26, 4-bromo-2-(5,6-dimethoxy-benzoimidazol-1-yl)-thiazole-5-carboxylic acid methyl ester (40 mg, 0.1 mmol) and 3-dimethylcarbamoylphenylboronic acid (29 mg, 0.15 mmol) gave 2-(5,6-Dimethoxy-benzoimidazol-1-yl)-4-(3-dimethylcarbamoyl-phenyl)-thiazole-5-carboxylic acid (1.8 mg, 4%) as a white solid. 1H NMR (400 MHz, DMSO-$d_6$) δ ppm 8.81 (s, 1 H); 7.84 (s, 1 H); 7.73-7.79 (m, 2H); 7.44-7.59 (m, 3 H); 7.40 (s, 1 H); 3.91 (s, 3 H, NCH$_3$), 3.86 (s, 3 H); 3.01 (s, 3 H); 2.74 (s, 3 H). MS 453 m/z (M+1).

Example 53

Thiophene-2-carboxylic acid N'-[4-(3-chloro-phenyl)-2-(5,6-dimethoxy benzoimidazol-1-yl)-thiazole-5-carbonyl]-hydrazide

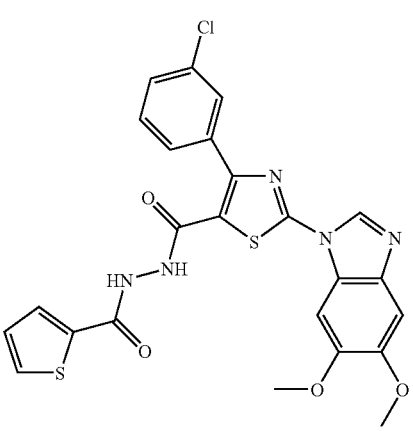

To a solution of 4-(3-Chloro-phenyl)-2-(5,6-dimethoxy-benzoimidazol-1-yl)-thiazole-5-carboxylic acid (41 mg, 0.1 mmol) and thiophene-2-carboxylic acid hydrazide (14.2 mg, 0.1 mmol, Aldrich) in N,N-dimethylformamide (1 ml) was added HATU (38 mg, 0.1 mmol) and diisopropylethylamine (26 µl, 0.15 mmol). The mixture was stirred at ambient temperature overnight. The solvent was reduced in vacuo and water (3 ml) was added. After sonication, the crude was filtered and sent directly for purification with prep-HPLC to afford thiophene-2-carboxylic acid N'-[4-(3-chloro-phenyl)-2-(5,6-dimethoxy benzoimidazol-1-yl)-thiazole-5-carbonyl]-hydrazide (37.9 mg, 70.2%) as a white solid. MS m/z 540 (M+1).

Example 54

4-(3-Chloro-phenyl)-2-(5,6-dimethoxy-benzoimidazol-1-yl)-thiazole-5-carboxylic acid pyrimidin-4-ylamide

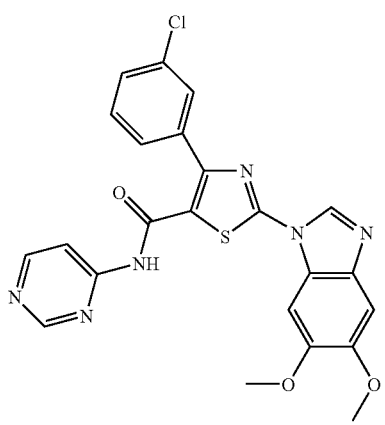

In a similar manner as described for Example 53, 4-(3-Chloro-phenyl)-2-(5,6-dimethoxy-benzoimidazol-1-yl)-thiazole-5-carboxylic acid (41 mg, 0.1 mmol) and 4-aminopyrimidine (9.5 mg, 0.1 mmol, Aldrich) gave 4-(3-Chloro-phenyl)-2-(5,6-dimethoxy-benzoimidazol-1-yl)-thiazole-5-carboxylic acid pyrimidin-4-ylamide (34.3 mg, 69.7%) as a white solid. MS m/z 493 (M+1).

Example 55

4-(3-Chloro-phenyl)-2-(5,6-dimethoxy-benzoimidazol-1-yl)-thiazole-5-carboxylic acid (3-methoxy-phenyl)-amide

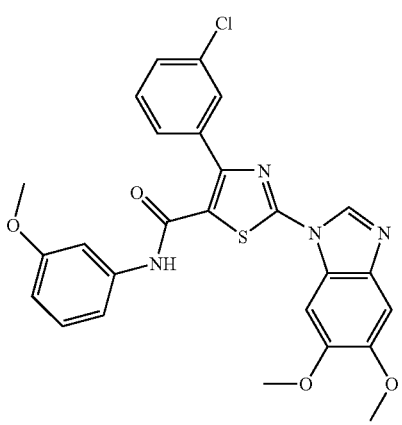

In a similar manner as described for Example 53, 4-(3-Chloro-phenyl)-2-(5,6-dimethoxy-benzoimidazol-1-yl)-thiazole-5-carboxylic acid (41 mg, 0.1 mmol) and 3-anisidine (12.3 mg, 0.1 mmol, Aldrich) gave 4-(3-Chloro-phenyl)-2-(5,6-dimethoxy-benzoimidazol-1-yl)-thiazole-5-carboxylic acid (3-methoxy-phenyl)-amide (45.1 mg, 86.6%) as a white solid. MS m/z 521 (M+1).

Example 56

4-(3-Chloro-phenyl)-2-(5,6-dimethoxy-benzoimidazol-1-yl)-thiazole-5-carboxylic acid thiazol-2-ylamide

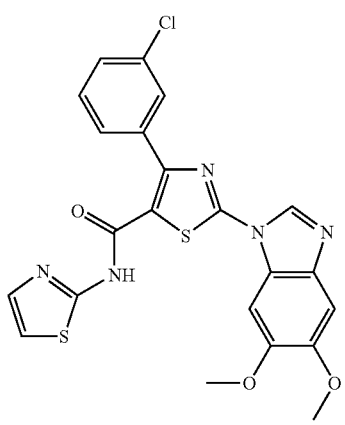

In a similar manner as described for Example 53, 4-(3-Chloro-phenyl)-2-(5,6-dimethoxy-benzoimidazol-1-yl)-thiazole-5-carboxylic acid (41 mg, 0.1 mmol) and 2-aminothiazole (10.0 mg, 0.1 mmol, Aldrich) gave 4-(3-Chloro-phenyl)-2-(5,6-dimethoxy-benzoimidazol-1-yl)-thiazole-5-carboxylic acid thiazol-2-ylamide (39.6 mg, 79.5%) as a white solid. MS m/z 498 (M+1).

Example 57

4-(3-Chloro-phenyl)-2-(5,6-dimethoxy-benzoimidazol-1-yl)-thiazole-5-carboxylic acid [1,2,4]triazol-4-ylamide

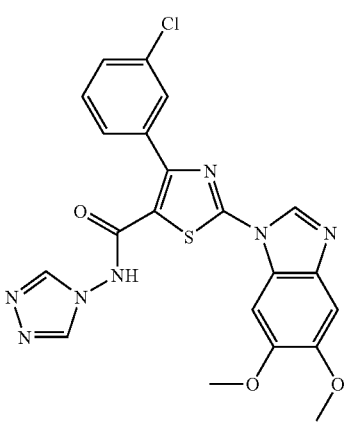

In a similar manner as described for Example 53, 4-(3-Chloro-phenyl)-2-(5,6-dimethoxy-benzoimidazol-1-yl)-thiazole-5-carboxylic acid (41 mg, 0.1 mmol) and 4-amino-

113

1,2,4-triazole (8.4 mg, 0.1 mmol, Aldrich) gave 4-(3-Chlorophenyl)-2-(5,6-dimethoxy-benzoimidazol-1-yl)-thiazole-5-carboxylic acid [1,2,4]triazol-4-ylamide (2.4 mg, 5.0%) as a white solid. MS m/z 482 (M+1).

Example 58

3-Methyl-benzoic acid N'-[4-(3-chloro-phenyl)-2-(5,6-dimethoxy-benzoimidazol-1-yl)-thiazole-5-carbonyl]-hydrazide

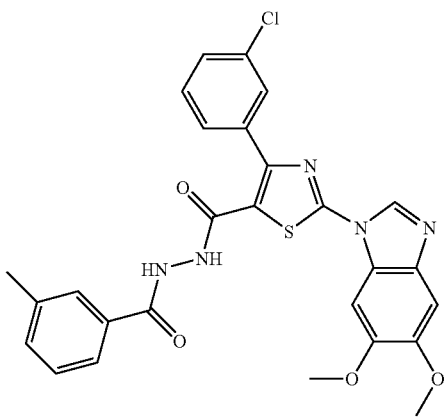

In a similar manner as described for Example 53, 4-(3-Chloro-phenyl)-2-(5,6-dimethoxy-benzoimidazol-1-yl)-thiazole-5-carboxylic acid (41 mg, 0.1 mmol) and m-toluic acid hydrazide (15.0 mg, 0.1 mmol, Lancaster) gave 3-Methyl-benzoic acid N'-[4-(3-chloro-phenyl)-2-(5,6-dimethoxy-benzoimidazol-1-yl)-thiazole-5-carbonyl]-hydrazide (2.1 mg, 3.8%) as a white solid. MS m/z 548 (M+1).

Example 59

5-Methoxy-6methyl-1H-benzoimidazole

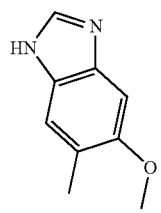

5-Methoxy-6-methyl-1H-benzoimidazole was prepared from 5-methoxy-4-methyl-2-nitrophenol according to the general procedure for benzimidazoles above. MS M/z 163 (M+1).

114

2-(5-Methoxy-6-methylbenzoimidazol-1-yl)-4-phenylthiazole-5-carboxylic acid and 2-(6-methoxy-5-methylbenzoimidazol-1-yl)-4-phenylthiazole-5-carboxylic acid

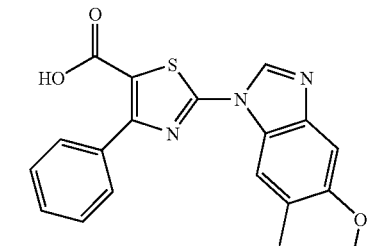

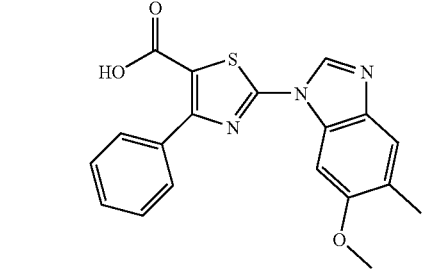

2-(5-Methoxy-6-methylbenzoimidazol-1-yl)-4-phenylthiazole-5-carboxylic acid and 2-(6-methoxy-5-methylbenzoimidazol-1-yl)-4-phenylthiazole-5-carboxylic acid were prepared in a similar manner as that for Example 1 starting with the reaction of 5-methoxy-6-methyl-1H-benzoimidazole and 2-Chloro-4-phenylthiazole-5-carboxylic acid ethyl ester. MS M/z 366 (M+1).

Example 60

4-(3-Chloro-phenyl)-2-(5,6-dimethoxy-benzoimidazol-1-yl)-thiazole-5-carboxylic acid (2-oxo-1,2-dihydro-pyrimidin-4-yl)-amide

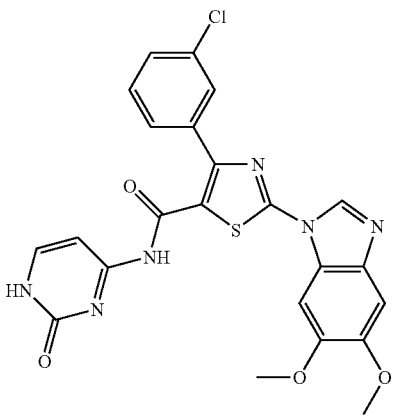

In a similar manner as described for Example 53, 4-(3-Chloro-phenyl)-2-(5,6-dimethoxy-benzoimidazol-1-yl)-thiazole-5-carboxylic acid (41 mg, 0.1 mmol) and cytosine (11.1 mg, 0.1 mmol, Aldrich) gave 4-(Chloro-phenyl)-2-(5,6-dimethoxy-benzoimidazol-1-yl)-thiazole-5-carboxylic acid (2-oxo-1,2-dihydro-pyrimidin-4-yl)-amide (5.6 mg, 11.0%) as a white solid. MS m/z 509 (M+1).

Example 61

2-(7-Hydroxy-benzoimidazol-1-yl)-4-phenyl-thiazole-5-carboxylic acid

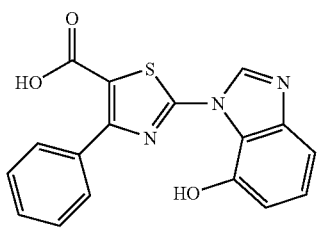

2-(7-Hydroxy-benzoimidazol-1-yl)-4-phenyl-thiazole-5-carboxylic acid was prepared by separating the mixture product of Example 7 on HPLC eluting with water and acetonitrile. MS M/z 338 (M+1).

Example 62

2-(5-Methylbenzoimidazol-1-yl)-4-phenylthiazole-5-carboxylic acid

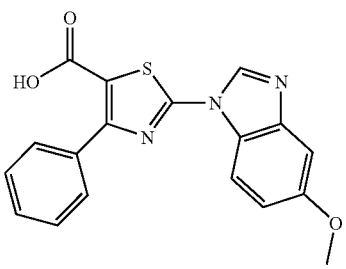

2-(5-Methylbenzoimidazol-1-yl)-4-phenylthiazole-5-carboxylic acid was prepared by separating the mixture product of Example 15 on super critical fluid chromatography with the following conditions: 100 bar, 30° C., 2.0 mL/min eluting a 12 mm AD column with 40% MeOH in super critical fluid $CO_2$. MS M/z 352 (M+1).

Example 63

2-[5-(2-Methoxy-ethoxy)-benzoimidazol-1-yl]-4-phenyl-thiazole-5-carboxylic acid ethyl ester and 2-[6-(2-methoxy-ethoxy)-benzoimidazol-1-yl]-4-phenyl-thiazole-5-carboxylic acid

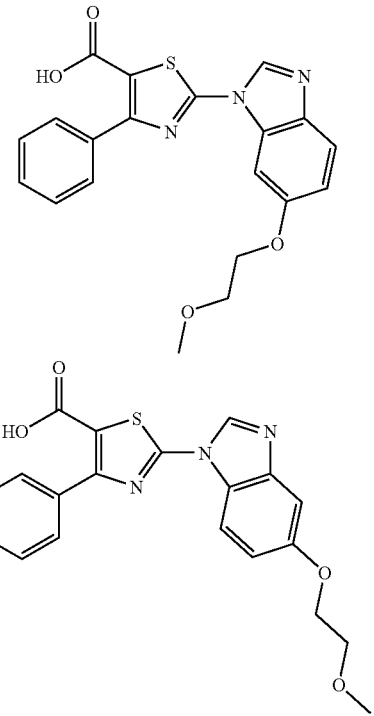

2-[5-(2-Methoxy-ethoxy)-benzoimidazol-1-yl]-4-phenyl-thiazole-5-carboxylic acid ethyl ester and 2-[6-(2-methoxy-ethoxy)-benzoimidazol-1-yl]-4-phenyl-thiazole-5-carboxylic acid (13.6 mg) were prepared using the procedure described for Example 48 from 2-(5-hydroxy-benzoimidazol-1-yl)-4-phenyl-thiazole-5-carboxylic acid ethyl ester and 2-(6-hydroxy-benzoimidazol-1-yl)-4-phenyl-thiazole-5-carboxylic acid ethyl ester. MS M/z 396 (M+1).

Example 64

4-(2-Chloro-pyridin-4-yl)-2-(5,6-dimethoxy-benzoimidazol-1-yl)-thiazole-5-carboxylic acid

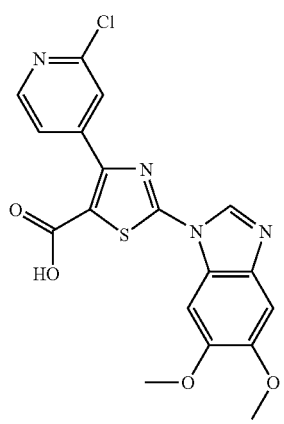

In a similar manner as described for Example 26, 4-bromo-2-(5,6-dimethoxy-benzoimidazol-1-yl)-thiazole-5-carboxylic acid methyl ester (120 mg, 0.3 mmol) and 2-chloropyridine-2-boronic acid (71 mg, 0.45 mmol) gave 4-(2-Chloro-pyridin-4-yl)-2-(5,6-dimethoxy-benzoimidazol-1-yl)-thiazole-5-carboxylic acid (58 mg, 46.4%) as a white solid. MS 417 m/z (M+1).

Example 65

2-(5-Hydroxy-benzoimidazol-1-yl)-4-phenyl-thiazole-5-carboxylic acid ethyl ester and 2-(6-hydroxy-benzoimidazol-1-yl)-4-phenyl-thiazole-5-carboxylic acid ethyl ester

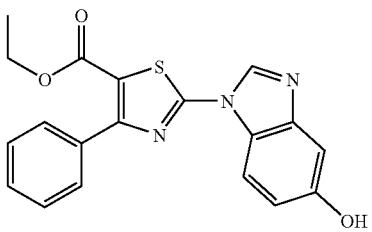

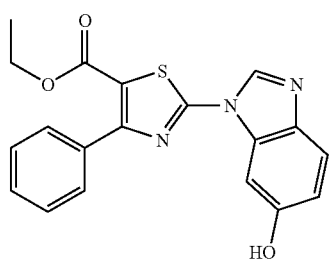

2-(5-Hydroxy-benzoimidazol-1-yl)-4-phenyl-thiazole-5-carboxylic acid ethyl ester and 2-(6-hydroxy-benzoimidazol-1-yl)-4-phenyl-thiazole-5-carboxylic acid ethyl ester (1.91 g, 5.2 mmol 70% pure) were prepared in a same procedure for Example 38 from 2-(5-methoxy-benzoimidazol-1-yl)-4-phenyl-thiazole-5-carboxylic acid ethyl ester and 2-(6-methoxy-benzoimidazol-1-yl)-4-phenyl-thiazole-5-carboxylic acid ethyl ester (2.53 g, 6.67 mmol) and Boron trifluoride dimethylsulfide (1.5 ml, 14 mmol). MS M/z 366 (M+1).

What is claimed is:

1. A compound of formula (1)

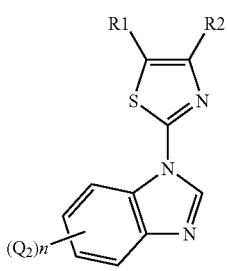

that inhibits the activity of the enzyme PLK1 wherein:
n is 1 or 2;
$Q_2$ is lower alkoxy;
R1 is selected from the group consisting of —C(O)OH and heterocyclyl; and
R2 is aryl optionally substituted with one or more substituents independently selected from the group consisting of halogen, lower alkoxy, lower alkyl, hydroxyl, lower alkenyl, halo-loweralkyl, hydroxy-loweralkyl, and —C(O)NR8R9 wherein R8 and R9 are each independently selected from the group consisting of hydrogen and lower alkyl, wherein two of said optional substituents can, together with the atoms to which they are bound, form a four to six-membered heterocyclic ring containing at least one atom independently selected from the group consisting of oxygen, nitrogen, and sulfur; and pharmaceutically acceptable salts thereof.

2. The compound of claim 1 wherein R2 is substituted aryl.
3. The compound of claim 2 wherein R1 is C(O)OH.
4. The compound of claim 1 wherein R2 is optionally substituted heteroaryl.
5. The compound of claim 3 wherein R2 is substituted phenyl.
6. The compound of claim 5 wherein R2 is phenyl substituted with at least one member selected from the group consisting of hydroxyl and halogen.
7. The compound of claim 6 wherein R2 is phenyl substituted with halogen.
8. The compound of claim 7 wherein R2 is phenyl substituted in the 3-position with halogen.
9. The compound of claim 2 wherein R1 is heterocyclyl.
10. The compound of claim 9, wherein said heterocyclyl group comprises a nitrogen atom.
11. A composition comprising a compound of claim 1 and one or more members selected from the group consisting of pharmaceutically acceptable carriers and adjuvants.

* * * * *